(12) United States Patent
Radjy

(10) Patent No.: US 9,321,398 B2
(45) Date of Patent: Apr. 26, 2016

(54) SYSTEMS, METHODS AND APPARATUS FOR PROVIDING TO A DRIVER OF A VEHICLE CARRYING A MIXTURE REAL-TIME INFORMATION RELATING TO A CHARACTERISTIC OF THE MIXTURE

(71) Applicant: QuipIP, LLC, Pittsburgh, PA (US)

(72) Inventor: Farrokh F. Radjy, Pittsburgh, PA (US)

(73) Assignee: QuipIP, LLC, Pittsburgh, PA (US)

(*) Notice: Subject to any disclaimer, the term of this patent is extended or adjusted under 35 U.S.C. 154(b) by 0 days.

(21) Appl. No.: 14/864,107

(22) Filed: Sep. 24, 2015

(65) Prior Publication Data
US 2016/0009224 A1 Jan. 14, 2016

Related U.S. Application Data

(63) Continuation of application No. 14/194,293, filed on Feb. 28, 2014, now Pat. No. 9,194,855.

(51) Int. Cl.
| | |
|---|---|
| *G01N 31/00* | (2006.01) |
| *B60Q 9/00* | (2006.01) |
| *G01N 33/18* | (2006.01) |
| *G01N 33/38* | (2006.01) |
| *G01N 33/14* | (2006.01) |
| *G06F 11/30* | (2006.01) |

(52) U.S. Cl.
CPC .............. *B60Q 9/00* (2013.01); *G01N 33/143* (2013.01); *G01N 33/18* (2013.01); *G01N 33/38* (2013.01); *G01N 33/383* (2013.01)

(58) Field of Classification Search
CPC ....................................... G01N 33/38
See application file for complete search history.

(56) References Cited

U.S. PATENT DOCUMENTS

| | | | |
|---|---|---|---|
| 2007/0046479 A1* | 3/2007 | Hines ................ | G01N 29/2462 340/584 |
| 2008/0221815 A1* | 9/2008 | Trost .................... | G01N 33/383 702/81 |

* cited by examiner

*Primary Examiner* — Phuong Huynh
(74) *Attorney, Agent, or Firm* — Lucas & Mercanti, LLP; Donald C. Lucas

(57) ABSTRACT

Information relating to a change made to a concrete mixture in a concrete mixer truck is obtained. An expected value of a selected characteristic of the concrete mixture is determined based on the change. A representation of the expected value is displayed on a processing device located in a cab of the concrete mixer truck. In one embodiment, the mixture comprises a concrete mixture. The change may comprise an addition of water to the mixture.

20 Claims, 35 Drawing Sheets

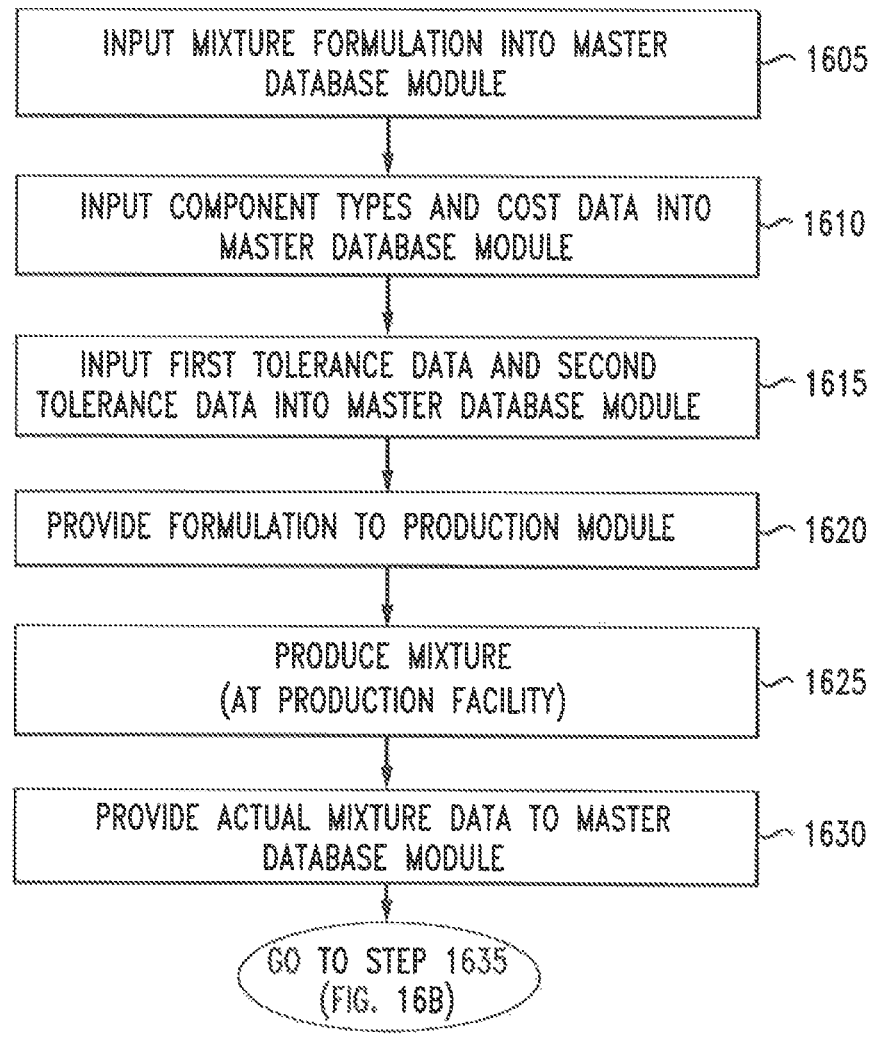

| PRODUCTION FACILITY | SDrCM | SDrW | SDrWCM | SD(ΔS) | POTENTIAL COST SAVING |
|---|---|---|---|---|---|
| PF-1 | sdrcm-1 | Sdrw-1 | Sdrwcm-1 | sd-1 | $0.12/cya |
| PF-2 | sdrcm-2 | Sdrw-2 | Sdrwcm-2 | sd-2 | $0.28/cya |
| PF-3 | sdrcm-3 | Sdrw-3 | Sdrwcm-3 | sd-3 | $1.06/cya |
| PF-4 | sdrcm-4 | Sdrw-4 | Sdrwcm-4 | sd-4 | $0.78/cya |
| ... | ... | ... | ... | ... | ... |

BENCHMARK (SDrCM) = sdrcm-2
BENCHMARK (SDrW) = sdrw-4

FIG. 20

SYSTEMS, METHODS AND APPARATUS FOR PROVIDING TO A DRIVER OF A VEHICLE CARRYING A MIXTURE REAL-TIME INFORMATION RELATING TO A CHARACTERISTIC OF THE MIXTURE

CROSS-REFERENCE TO RELATED APPLICATIONS

This application is a continuation of and claims priority to U.S. application Ser. No. 14/194,293, filed Feb. 28, 2014, which is incorporated herein by reference.

TECHNICAL FIELD

This specification relates generally to real-time systems and methods for managing data, and more particularly to systems and methods for providing to a driver of a vehicle carrying a mixture real-time information relating to a characteristic of the mixture.

BACKGROUND

In many industries, consumers order a product based on a specification, and subsequent to their order, the product is manufactured based on a formulation that specifies a plurality of components and a particular method, procedure, or recipe to be followed. Once the product is made, it is shipped by the producer to the consumer. In such industries where an order is placed prior to manufacturing, orders are based on expected characteristics and costs of the product. When the product is made at a later date, it is important that the product be made and delivered according to the expected characteristics and costs.

In practice, however, changes often occur during the manufacturing and shipping process due to a variety of factors, such as an unavailability of components, a failure to include the correct quantity of a component specified in the recipe, or the addition of a component that is not listed in or is consistent with the formulation. Such changes may occur due to human error, either accidental or deliberate, or due to formulations being maintained in a non-normalized fashion such as in multiple disconnected systems, or due to malfunction of a device involved in the production system, or due to unforeseen events. Furthermore, a component specified in the formulation may be incorrectly batched, or knowingly or unknowingly replaced with assumed equivalent components because the raw materials are not available, or for other reasons. One well known example is the use of either sucrose or high fructose corn syrup in soft drinks. Typically, during production of a soft drink, one of these two sweeteners is selected and used depending upon the cost and availability of the sweetener at the time when the soft drink product is manufactured.

Similar practices are used in the ready mix concrete industry. A given mixture of concrete, defined by a particular formulation (specifying types of components and quantities thereof), may be produced differently at different production facilities and/or at different times, depending on a variety of factors. For example, the types and quantities of cement and Pozzolanic cementitious materials, chemicals, different types of aggregates used often varies between batches, due to human error, or for reasons which may be specific to the time and location of production. Some components may not be available in all parts of the world, a component may be incorrectly batched, components may be replaced deliberately or accidentally, etc. Furthermore, in the ready mix concrete industry, it is common for changes in the mixed composition to occur during transport of the product. For example, water and/or chemicals may be added due to weather, or due to the length of time spent in transit to the site where the ready mix concrete is poured, or due to customer demands. Changes to a mixture may also occur during the batching process. For example, an incorrect amount of a critical component such as water or cementitious may be added. Similarly, an incorrect amount of fly ash or other pozzolans, such as slag, may be used to make the cementitious portion. Furthermore, it is common industry practice to make certain changes to a concrete mixture while the mixture is being transported in a mixer truck. For example, the driver may add water at various stages during transport. Such practices may be prone to human error.

Due to the reasons set forth above, a customer often receives a product which differs from the product ordered. The quality of the product may not meet expectations. Furthermore, any change made to a product may impact the producer's cost and profits.

In addition, in many industries, various activities important to a producer's business, such as sales, purchasing of raw materials, production, and transport, are conducted independently of one another. The disjointed nature of the sales, purchasing of raw materials, production, and transport creates an additional hindrance to the producer's, and the customer's, ability to control the quality and cost of the final product.

Accordingly, there is a need for improved production management systems that provide, to producers and to customers, greater control over various aspects of the production system used to produce a product, and thereby provide greater control over quality and costs.

SUMMARY

In accordance with an embodiment, a method of managing information is provided. Information relating to a change made to a concrete mixture in a concrete mixer truck is obtained. For example, the change may comprise an addition of water to the mixture. An expected value of a selected characteristic of the concrete mixture is determined based on the change. A representation of the expected value is displayed on a processing device located in a cab of the concrete mixer truck. For example, a difference value representing a difference between the expected value and a design value may be displayed in the form of a gauge on a computer, or as an App (referred to herein as an App or App display) on an Android or Apple smart phone or Tablet, used by the driver of the truck.

In various embodiments, the characteristic comprises one of a quantity of water in the mixture, a strength of the mixture, a slump of the mixture, a standard deviation of strength, a standard deviation of slump, a quantity of cementitious in the mixture, and a cost measure associated with the mixture.

In another embodiment, the concrete mixture is produced based on a formulation. A graphical representation of a gauge is displayed, wherein an indicator of the gauge indicates a difference between the expected value and a second value of the characteristic determined based on the formulation.

In accordance with another embodiment, a method of managing information is provided. A change made to a mixture during transport of the mixture in a vehicle is determined, wherein the mixture is associated with a formulation. An expected measure of a characteristic of the mixture is determined based on the change. A desired measure of the characteristic is determined based on the formulation. A difference value representing a difference between the expected measure and the desired measure is determined. The difference value is transmitted to a communication device disposed in the vehicle. The communication device is caused to display the difference value.

In one embodiment, the mixture comprises a concrete mixture, and the vehicle comprises a concrete mixer truck.

In another embodiment, the change comprises one of an addition of water and an addition of a chemical.

In another embodiment, the change comprises a first addition of a first quantity of water to the mixture. Information relating to a second addition of a second quantity of water to the mixture is received. The expected measure of the characteristic of the mixture is determined based on the change and the second addition of water.

In another embodiment, the characteristic comprises one of a quantity of water in the mixture, a strength of the mixture, a slump of the mixture, a standard deviation of strength, a standard deviation of slump, a quantity of cementitious in the mixture, and a cost measure associated with the mixture.

In another embodiment, determining an expected measure of a characteristic of the mixture based on the change comprises examining historical data relating to the effect of the change on the characteristic.

In another embodiment, the communication device is caused to display a graphical representation of a gauge, wherein an indicator of the gauge indicates the difference value.

In another embodiment, the communication device displays a shaded region on the gauge, the shaded region representing a range of difference values within acceptable tolerances.

In accordance with another embodiment, a system includes at least one memory storing computer program instructions. The system also includes at least one processor configured to execute the computer program instructions which, when executed on the at least one processor, cause the at least one processor to perform operations including obtaining, from a device in a vehicle, information relating to a change made to a mixture while the mixture is being transported in the vehicle, determining an expected value of a selected characteristic of the mixture based on the change, and causing a communication device located in the vehicle to display a representation of the expected value.

These and other advantages of the present disclosure will be apparent to those of ordinary skill in the art by reference to the following Detailed Description and the accompanying drawings.

BRIEF DESCRIPTION OF THE DRAWINGS

FIGS. 16A-16B comprise a flowchart of a method of producing and analyzing a mixture in accordance with an embodiment;

FIG. 20 shows a web page containing statistical information for a plurality of production facilities in accordance with an embodiment;

DETAILED DESCRIPTION

Figure 1A:
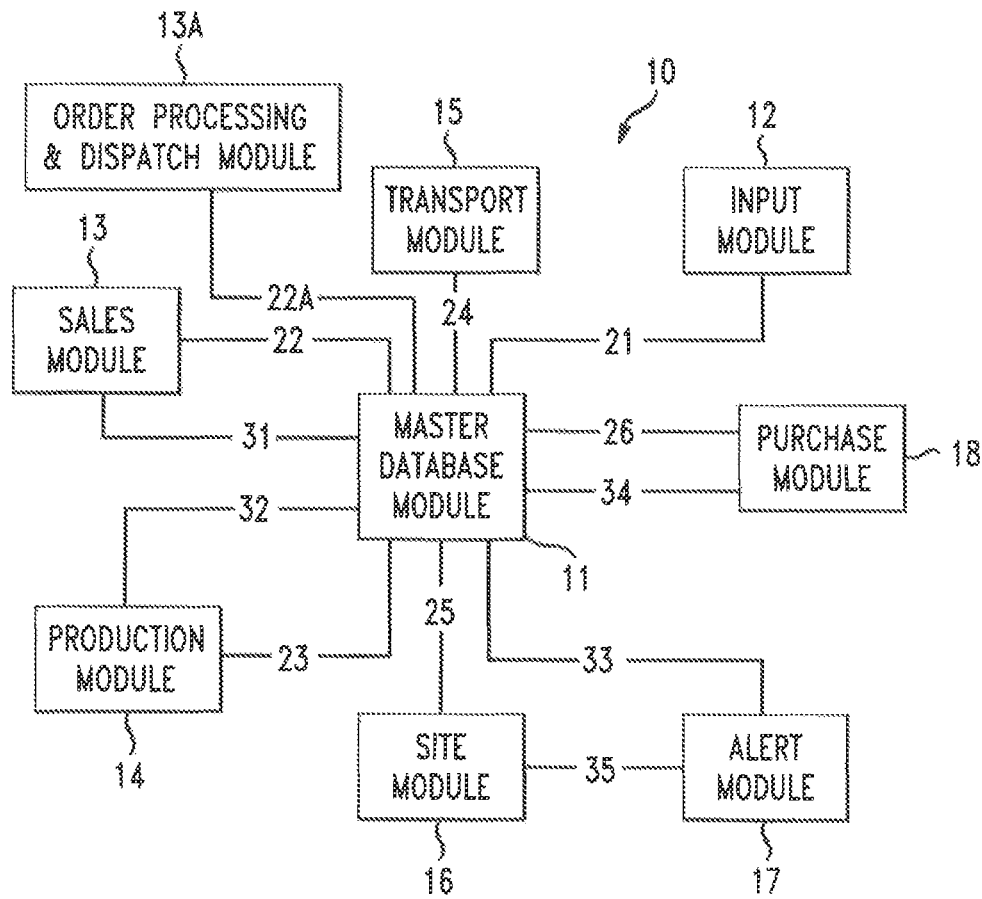
FIG. 1A illustrates a product management system in accordance with an embodiment.

In accordance with embodiments described herein, systems and methods of managing a closed-loop production management system used for production and delivery of a formulation-based product are provided. Systems, apparatus and methods described herein are applicable to a number of industries, including, without limitation, the food manufacturing industry, the paint industry, the fertilizer industry, the chemicals industry, the oil refining industry, the pharmaceuticals industry, agricultural chemical industry and the ready mix concrete industry.

In accordance with an embodiment, a method of managing a closed loop production system is provided. An order relating to a formulation-based product is received, wherein fulfilling the order requires production of the formulation-based product at a first location, transport of the formulation-based product in a vehicle to a second location different from the first location, and performance of an activity with respect to the formulation-based product at the second location. First information relating to a first change made to the formulation-based product at the first location is received, from the first location, prior to transport of the formulation-based product. Second information relating to a second change made to the formulation-based product during transport of the formulation-based product is received during transport of the formulation-based product. Third information relating to the activity performed with respect to the formulation-based product at the second location is received from the second location. The first, second, and third information are stored in a data structure, and may be displayed with an analysis of the impact of selected information on the cost of the product.

In one embodiment, the processor operates within a product management system comprising a plurality of modules operating at independent locations associated with various stages of the ordering, production, transport and delivery of the product.

In accordance with an embodiment, the product is a formulation-based product. In one embodiment, the product is a formulation-based concrete product. In other embodiments, the formulation-based product may be any type of product that is manufactured based on a formulation. For example, the formulation-based product may be a chemical compound or other type of chemical-based product, a petroleum-based product, a food product, a pharmaceutical drug, etc. Systems, apparatus and methods described herein may be used in the production of these and other formulation-based products.

In another embodiment, statistical information concerning a plurality of production facilities is generated and provided to a producer and/or a customer. For each of a plurality of production facilities, a series of actions is performed. For each of a plurality of batches of a concrete mixture produced at the respective production facility based on a formulation, a first difference between a measured quantity of cementitious and a first quantity specified in the formulation is determined. A first standard deviation is determined based on the first differences. For each of the plurality of batches, a second difference between a measured quantity of water and a second quantity specified in the formulation is determined. A second standard deviation is determined based on the second differences. A first benchmark is selected from among the first standard deviations, and a second benchmark is selected from among the second standard deviations. An amount by which costs may be reduced by improving production at the production facility to meet the first and second benchmarks is determined.

In accordance with another embodiment, information relating to a change made to a concrete mixture in a concrete mixer truck is obtained. For example, the change may comprise an addition of water to the mixture. An expected value of a selected characteristic of the concrete mixture, such as water content, strength, slump, etc., is determined based on the change. A representation of the expected value is displayed on a processing device located in a cab of the concrete mixer truck. For example, a difference between the expected value and a design value may be displayed in the form of a gauge, displayed on a computer carried by the driver of the truck.

The terms "formulation," "recipe," and "design specification" are used herein interchangeably. Similarly, the terms "components" and "ingredients" are used herein interchangeably.

FIG. 1A illustrates a production management system in accordance with an embodiment. Product management system 10 includes a master database module 11, an input module 12, a sales module 13, an order processing & dispatch module 13A, a production module 14, a transport module 15, a site module 16, an alert module 17 and a purchasing module 18.

Master database module 11 may be implemented using a server computer equipped with a processor, a memory and/or storage, a screen and a keyboard, for example. Modules 12-18 may be implemented by suitable computers or other processing devices with screens for displaying and keep displaying data and keyboards for inputting data to the module.

Master database module 11 maintains one or more product formulations associated with respective products. In the illustrative embodiment, formulations are stored in a database; however, in other embodiments, formulations may be stored in another type of data structure. Master database module 11 also stores other data related to various aspects of production management system 10. For example, master database module may store information concerning acceptable tolerances for various components, mixtures, production processes, etc., that may be used in system 10 to produce various products. Stored tolerance information may include tolerances regarding technical/physical aspects of components and processes, and may also include tolerances related to costs. Master database module 11 may also store cost data for various components and processes that may be used in system 10.

Each module 12-16 and 18 transmits data to master database module 11 by communication lines 21-26, respectively. Master database module 11 transmits data to modules 13, 14, 17 and 18 by communication lines 31-34, respectively. Order processing & dispatch module is linked to master database module via communication line 22A. Each communication line 21-26 (including line 22A) and 31-34 may comprise a direct communication link such as a telephone line, or may be a communication link established via a network such as the Internet, or another type of network such as a wireless network, a wide area network, a local area network, an Ethernet network, etc.

Alert module 17 transmits alerts to the producer and/or customers by communication line 35 to site module 16.

Master database module 11 stores data inputted from modules 12-16 and 18. Master database module 11 stores data in a memory or storage using a suitable data structure such as a database. In other embodiments, other data structures may be used. In some embodiments, master database module 11 may store data remotely, for example, in a cloud-based storage network.

Input module 12 transmits to master database module 11 by communication line 21 data for storage in the form of mixture formulations associated with respective mixtures, procedures for making the mixtures, individual ingredients or components used to make the mixture, specifics about the components, the theoretical costs for each component, the costs associated with mixing the components so as to make the product or mixture, the theoretical characteristics of the product, acceptable tolerances for variations in the components used to make the product, the time for making and delivering the product to the site and costs associated shipping the product.

The terms "product" and "mixture" are used interchangeably herein.

Data transmitted by input module 12 to master database module 11 and stored in master database module 11 may be historical in nature. Such historical data may be used by the sales personnel through sales module 13 to make sales of the product.

In one embodiment, sales module 13 receives product data by communication line 31 from master database module 11 relating to various products or mixtures that are managed by system 10, the components that make up those products/mixtures, the theoretical costs associates with the components, making the mixture and delivery of the mixture, times for delivery of the mixture and theoretical characteristics and performance specifications of the product. Order processing & dispatch module 13A processes orders and handles certain dispatching activities.

Figure 1B:
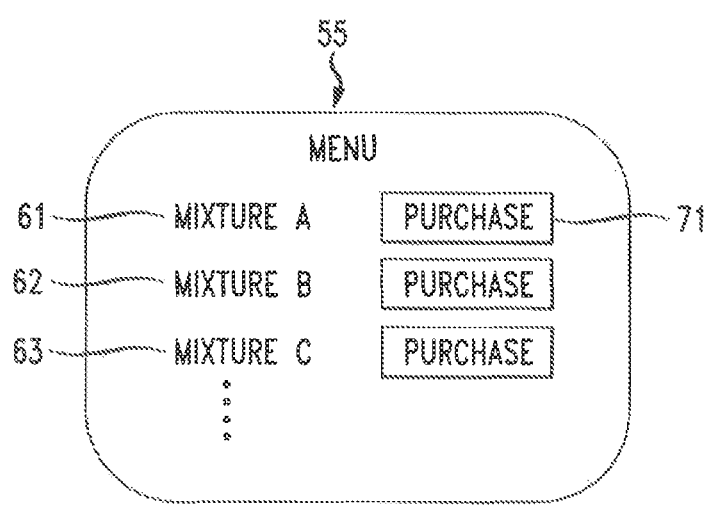
FIG. 1B shows an exemplary menu that may be presented to a customer in accordance with an embodiment.

Sales module 13 may present all or a portion of the product data to a producer and/or customer in the form of a menu of options. FIG. 1B shows an exemplary menu 55 that may be presented to a producer and/or customer in accordance with an embodiment. Menu 55 comprises a list of mixtures available for purchase, including Mixture A (61), Mixture B (62), Mixture C (63), etc. Each mixture shown in FIG. 1B represents a product offered for sale. For example, each mixture may be a respective concrete mixture that may be purchased by a customer. Menu 55 is illustrative only; in other embodiments, a menu may display other information not shown in FIG. 1B. For example, a menu may display the components used in each respective mixture, the price of each mixture, etc.

From the menu, the producer and/or customer may choose one or more products to purchase. For example, a producer and/or customer may purchase Mixture A (61) by selecting a Purchase button (71). When the producer and/or customer selects a mixture (by pressing Purchase button (71), for example), sales module 13 generates an order for the selected mixture and transmits the order by communication line 22 to master database module 11. The order may specify the mixture selected by the producer and/or customer, the components to be used to make the selected mixture, a specified quantity to be produced, the delivery site, the delivery date for the product, etc. An order may include other types of information.

In accordance with an embodiment, the producer and/or customer may input a specialty product into system 10. Such input may be accomplished through input module 12.

Figure 1C:
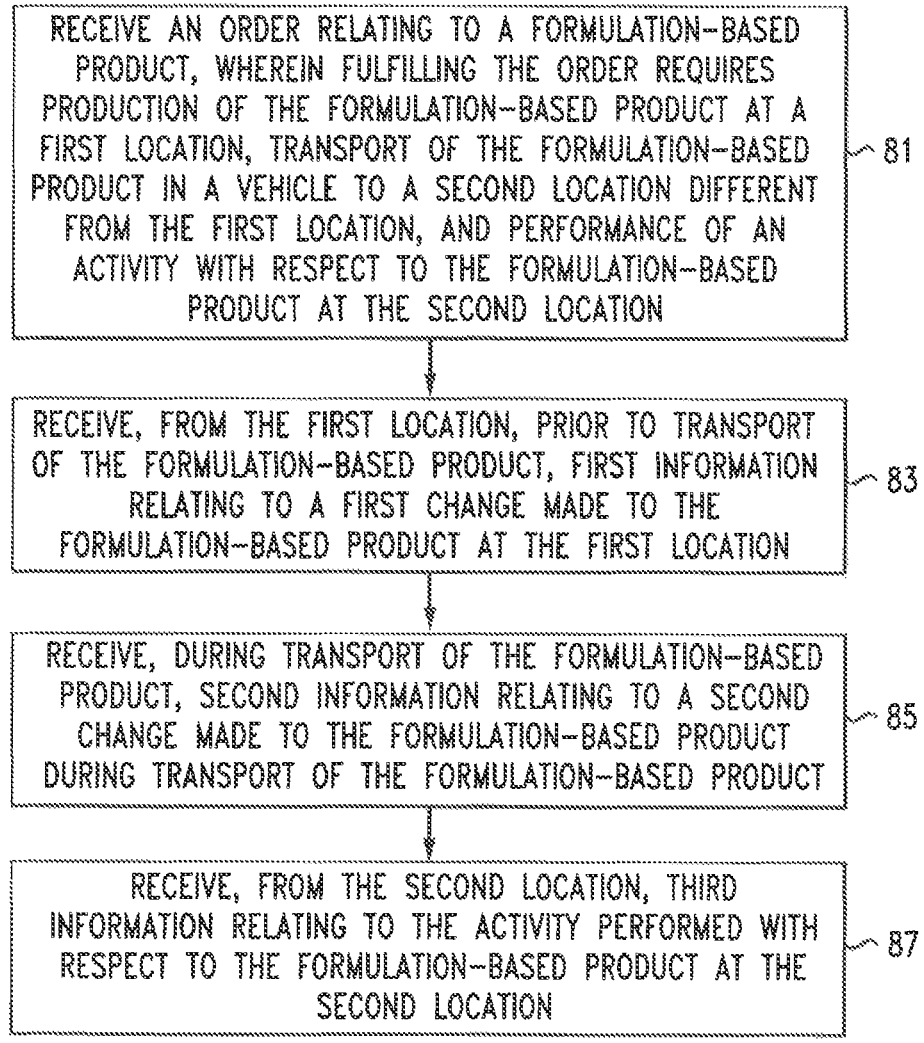
FIG. 1C is a flowchart of a method of managing a production system in accordance with an embodiment.

Producer and/or customer orders are transmitted to master database module 11. Master database module 11 uses an integrated database system to manage information relating to the orders, as well as the production, transport, and delivery of the ordered products. FIG. 1C is a flowchart of a method of managing a production system in accordance with an embodiment. At step 81, an order relating to a formulation-based product is received, wherein fulfilling the order requires production of the formulation-based product at a first location, transport of the formulation-based product in a vehicle to a second location different from the first location, and performance of an activity with respect to the formulation-based product at the second location. As described above, the producer's and/or customer's order is transmitted to master database module 11. Master database module receives the order from sales module 13, and stores the order.

Based on the order inputted to master database module 11, master database module 11 places a production order for production of the product to production module 14 by communication line 32. Production module 14 is located at a production facility capable of manufacturing the purchased product in accordance with the order.

In the illustrative embodiment, the product is a formulation-based product. Thus, the product may be produced based on a formulation defining a plurality of components and respective quantities for each of the components. The formulation may also specify a method, or recipe, for manufacturing the product. The production order provided to the production module 14 may include the mixture or product to be made, the components to be used to make the mixture or product, the specifics about the individual components, the method to make the mixture and the delivery dates. The product is produced at the production facility and placed in a vehicle for transport to a delivery site specified in the order.

At step 83, first information relating to a first change made to the formulation-based product at the first location is received from the first location, prior to transport of the formulation-based product. If any changes are made to the product at the production facility, production module 14 transmits information relating to such changes to master database module 11. For example, a particular component specified in the formulation may be replaced by an equivalent component. In another example, a quantity of a selected component specified in the formulation may be altered. In another example, an additional component not specified in the formulation may be added. For example, components such as water, cementitious, particular chemicals, particular fibers, etc., may be replaced, added, or their specified quantities may be altered. Master database module 11 receives and stores such information.

At step 85, second information relating to a second change made to the formulation-based product during transport of the formulation-based product is received during transport of the formulation-based product. If any changes are made to the product during transport of the product, transport module 15 transmits information relating to such changes to master database module 11. Master database module 11 receives and stores such information.

Upon arrival at the specified delivery site, the product is delivered. At step 87, third information relating to the activity performed with respect to the formulation-based product at the second location is received from the second location. For example, site module 16 may transmit to master database module 11 information indicating the time of delivery, or information relating to the performance of the product after delivery.

In the illustrative embodiment, information transmitted among modules 11-19, and to a producer and/or customer, may be transmitted in the form of an alert. An alert may be any suitable form of communication. For example, an alert may be transmitted as an electronic communication, such as an email, a text message, etc. Alternatively, an alert may be transmitted as an automated voice message, or in another form.

In one embodiment, information is transmitted to master database module 11 in real time. For example, strict rules may be applied requiring that any information concerning changes to a product that is obtained by any module (including production module 14, purchase module 18, transport module 15, site module 16, etc.) be transmitted to master database module 11 within a predetermined number of milliseconds.

Various embodiments are discussed in further detail below.

Figure 2:
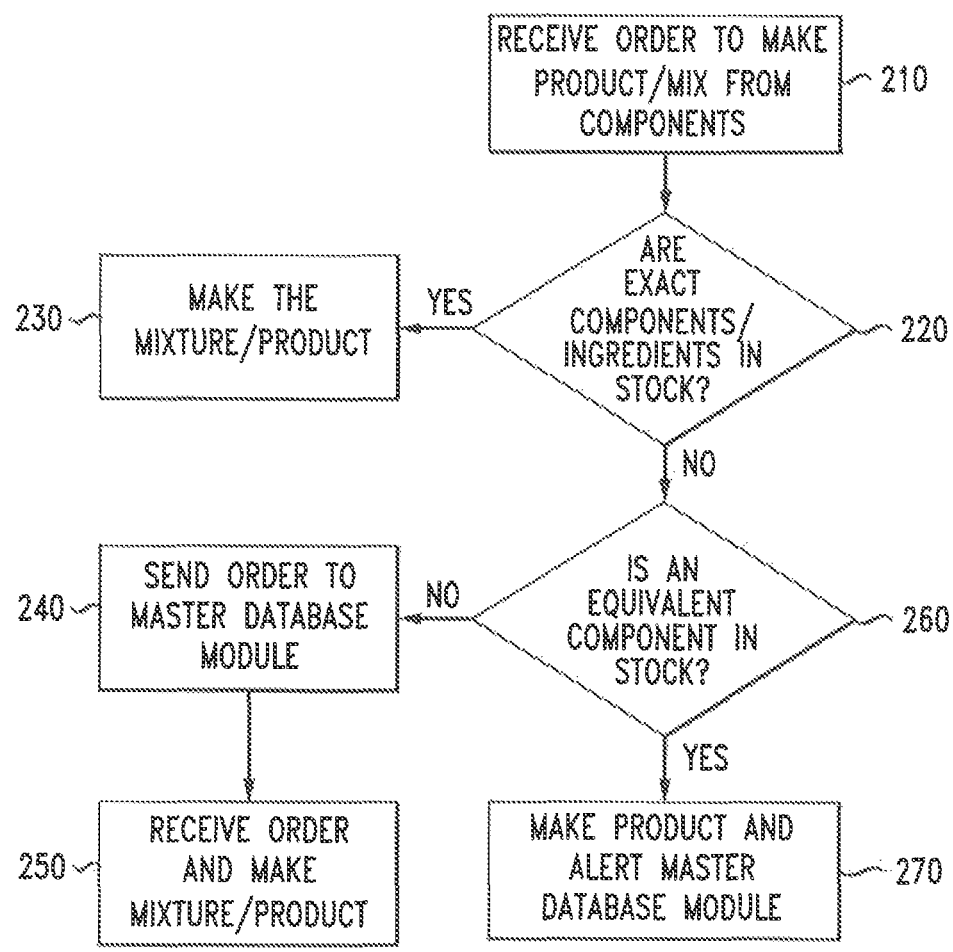
FIG. 2 is a flowchart of a method of producing a mixture in accordance with an embodiment.

As described above, in some embodiments, the product is made at a production facility in accordance with a predetermined formulation. Production module 14 operates at the production facility and has stored data as to the specifics of the individual components or raw ingredients on hand at the facility. FIG. 2 is a flowchart of a method of producing a mixture in accordance with an embodiment. At step 210, an order to make a product/mixture from specified components is received. Referring to block 220, if the exact components or ingredients are in stock, the production facility proceeds to make the mixture/product (step 230). If the production facility does not have on hand the exact components needed to make the mixture/product, then the method proceeds to step 260 and determines whether an equivalent component is in stock. If an equivalent component is in stock, the method proceeds to step 270. At step 270, production module 14 makes the product using the equivalent component and alerts master database module 11 of the change. Such a replacement may change the cost of the raw materials and/or the characteristics of the mixture/product which is finally made.

Returning to block 260, if there is no equivalent component in stock, the production module 14 may send an order by communication line 32 to master database module 11 for the specified component (or for the equivalent component). When the order is received, production module 14 makes the product (step 240). The manufactured formulation and physical results are sent to master database module 11 (step 250).

In another embodiment, production module 14 alerts master database module 11 if the method of manufacture specified in a mixture formulation is modified. For example, a step of the method may be changed or eliminated, or a new step may be added. Master database module stores information related to the change. Master database module 11 may also determine if the change is within acceptable tolerances and alert the producer and/or customer if it is not within acceptable tolerances. For example, master database module 11 may compare the modified method to stored tolerance information to determine if the modified method is acceptable.

Figure 3:
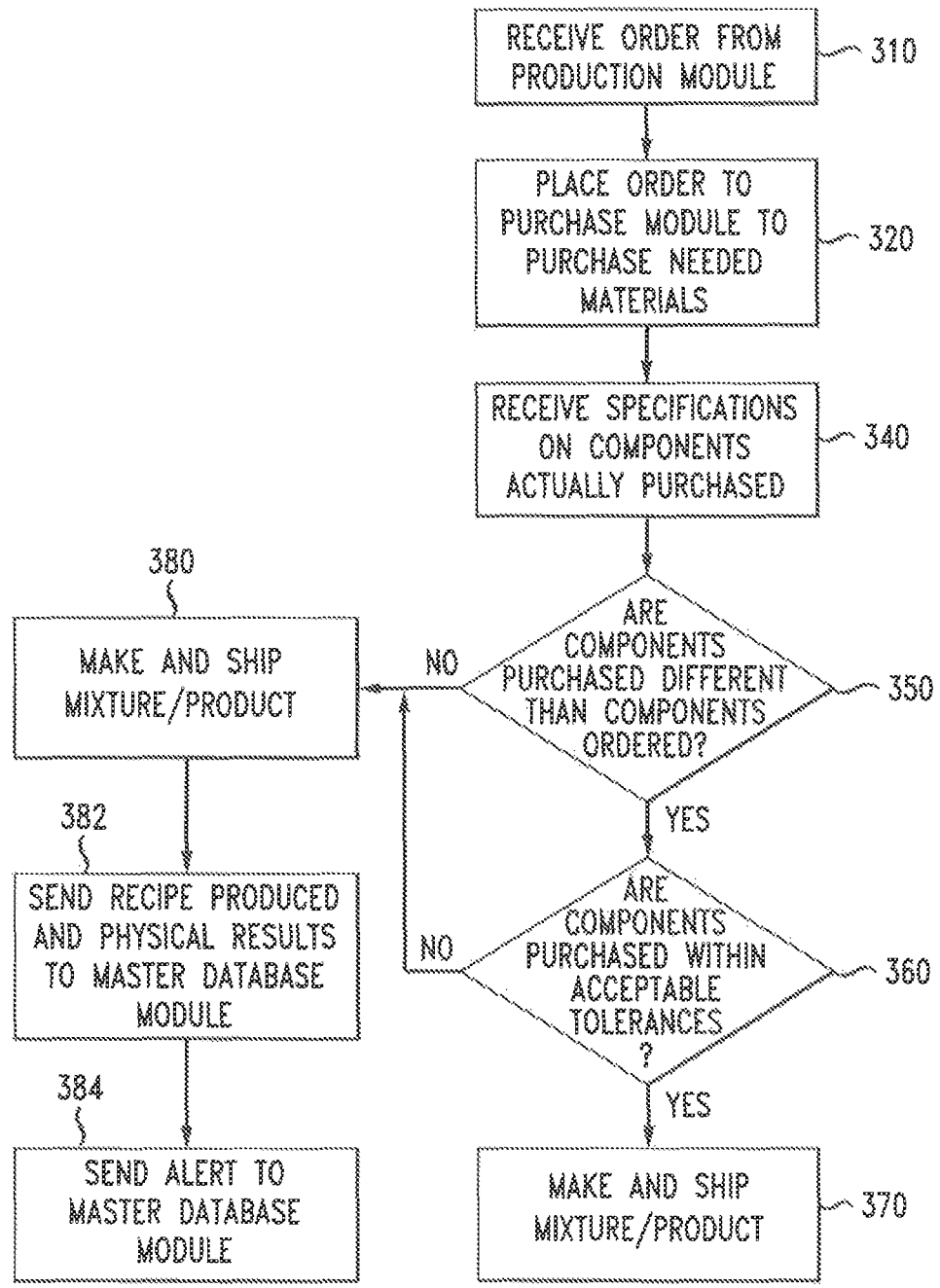
FIG. 3 is a flowchart of a method of handling an order received from a production facility in accordance with an embodiment.

FIG. 3 is a flowchart of a method of handling an order received from a production facility in accordance with an embodiment. At step 310, an order is received from production module 14, by master database module 11. At step 320, master database module 11 places an order by communication line 34 to purchase module 18 to purchase the needed components or raw materials. Purchase module 18 transmits by communication line 26 the specifics of the components that it has purchased and the estimated delivery date to the production facility as well as the costs associated with the component. Purchase module 18 is associated with a raw material/component supply facility. At step 340, master database module 11 receives the specifics on the components actually purchased by purchase module 18.

Referring to block 350, if the components purchased (by purchase module 18) are the same as the order placed, the method proceeds to step 380, and the product is made and shipped to the production facility. At step 382, the recipe produced and the physical results are sent to master database module 11. At step 384, an alert is sent to master database module 11.

Returning to block 350, if the components purchased (by purchase module 18) differ from those specified in the order, the method proceeds to block 360. Master database module 11 compares the components purchased, either those replaced by the production facility or those purchased by the purchase module 18, to stored tolerance information (which may include tolerances regarding physical/technical aspects of a component and/or cost tolerances). Referring to block 360, if the replacement components fall within acceptable tolerances both for performance characteristics and cost, then at step 370, the mixture/product is made is shipped. If the cost or characteristics of the raw ingredients fall outside acceptable tolerances, then the method proceeds to step 380 (described above).

Figure 4:
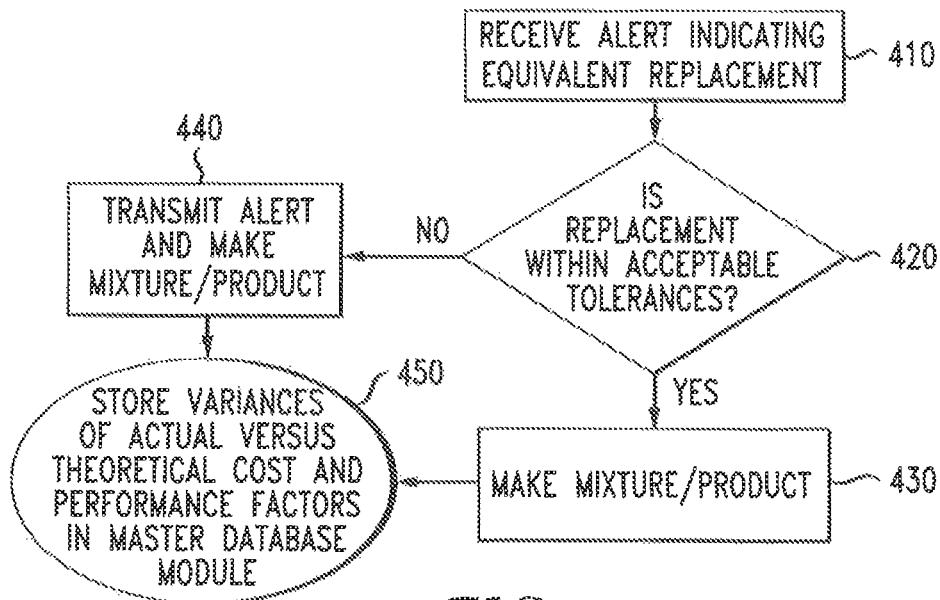
FIG. 4 illustrates a method of responding to an alert when a production facility replaces an ingredient with a known equivalent, in accordance with an embodiment.

FIG. 4 is a flowchart of a method of responding to an alert in accordance with an embodiment. Specifically, FIG. 4 illustrates a method of responding to an alert when a production facility replaces an exact ingredient with a known equivalent, in accordance with an embodiment. At step 410, an alert indicating an equivalent replacement is received by master database module 11 from production module 14. Referring to block 420, a determination is made by master database module 11 whether the equivalent component is within acceptable tolerances. If the equivalent component is within acceptable tolerances, the method proceeds to step 430 and the product is made. Master database module 11 instructs production module 14 to proceed with manufacturing the mixture. If the equivalent component is not within acceptable tolerances, the method proceeds to step 440. At step 440, and an alert is transmitted and the product is made. For example, an alert may be transmitted by master database module 11 or by alert module 17 to the producer and/or customer.

At step 450, the variances of actual versus theoretical cost and performance factors are stored at master database module 11.

As described above, production module 14 receives instructions from master database module 11, prior to production of a mixture, specifying the recipe and components required for producing the mixture. However, from time to time the batched amounts of each component (i.e., the amount of each component in the batch actually produced) differs from the amounts specified in the recipe received from master database module 11 due to statistical or control factors.

Figure 5:
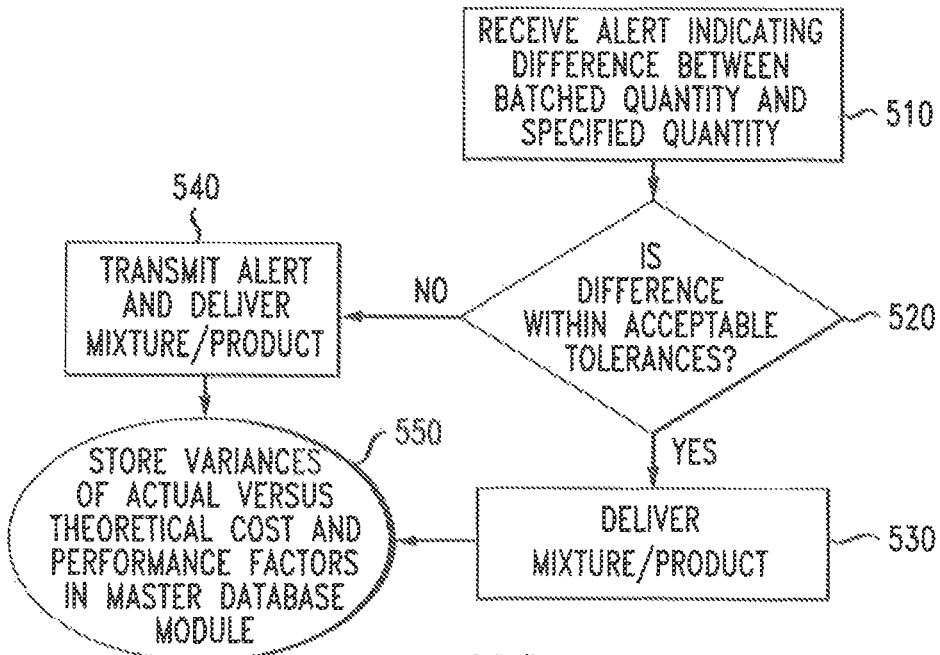
FIG. 5 is a flowchart of a method of responding to an alert indicating a difference between a batched quantity and a specified quantity in accordance with an embodiment.

When quantity variances are outside the specified tolerances, alerts are transmitted and the actual amounts produced, and cost variances from target costs, are provided to master database module 11. FIG. 5 is a flowchart of a method of responding to an alert indicating a difference between a batched quantity and a specified recipe quantity in accordance with an embodiment. At step 510, an alert is received indicating a difference between a batched quantity and a specified recipe quantity. The alert typically indicates variances of actual versus theoretical cost and performance factors. Referring to block 520, if the differences are within acceptable tolerances, the method proceeds to step 530 and the product is delivered. If the differences are not within acceptable tolerances, the method proceeds to step 540. At step 540, an alert is transmitted and the product is delivered. An alert may be transmitted to the producer and/or customer, for example. At step 550, the variances of actual versus theoretical cost and performance factors are stored at master database module 11. In other embodiments, variances are not stored.

After production of the mixture, the production facility uses one or more transport vehicles to transport the product/mixture from the production facility to the producer's and/or the customer's site. Such transport vehicles may include trucks, automobiles, trains, airplanes, ships, etc. Each transport vehicle is equipped with a transport module such as transport module 15. Transport module 15 transmits by communication line 24 to master database 11 information concerning the transport of the product/mixture. The information concerning the transport can include changes which are made to the mixture during transport (e.g., addition of water or other chemicals), the length of travel, temperatures during transport, or other events that occur during transport. For example, in the ready mix concrete industry it is common for a truck transporting the mixture from the production facility to a delivery site to add water and/or chemicals during the transport process. Information indicating such addition of chemicals or water is transmitted to master database module 11 by communication line 24. Furthermore, in the ready mix concrete industry, measuring and recording the temperature of the concrete during transport is advantageous for several reasons: (a) such data can be used to determine a maturity value per ASTM c1074; (b) such data, in combination with reference heat of hydration data may be used to determine degree of hydration attained during transport; (c) the data, in combination with reference strength and heat of hydration data may be used to determine pre-placement strength loss due to pre-hydration prior to discharge of the concrete at project site.

Figure 6:
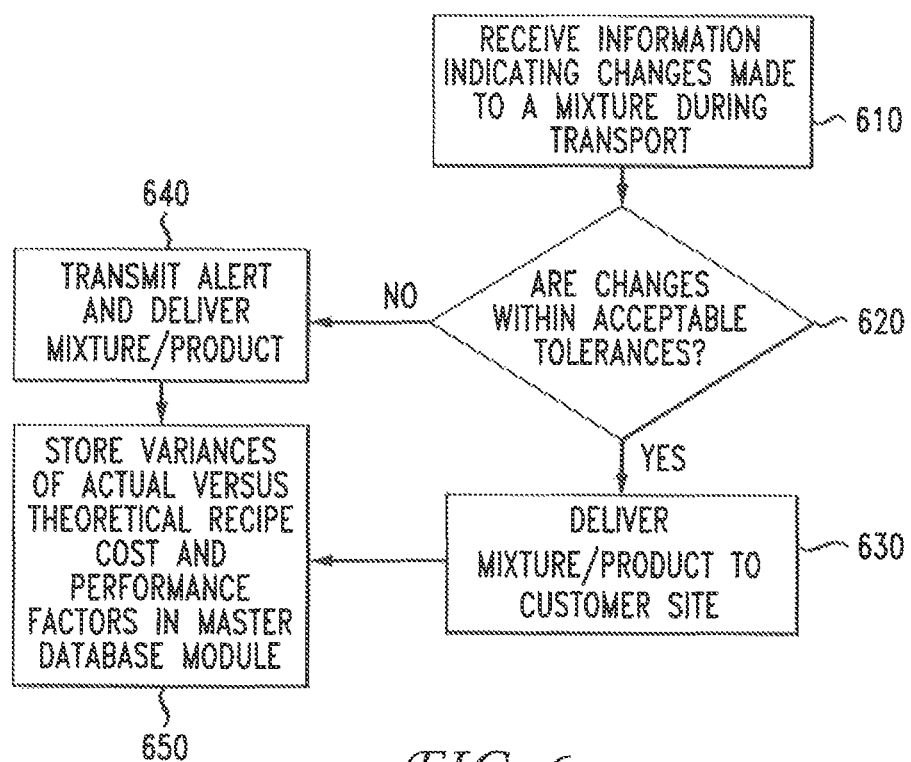
FIG. 6 is a flowchart of a method of managing transport-related data in accordance with an embodiment.

The transport-related information is transmitted by transport module 15 to master database module 11. For example, such information may be transmitted in the form of an alert. The information is analyzed by master database module 11 to determine whether the changes that are made are within acceptable tolerances. FIG. 6 is a flowchart of a method of managing transport-related data in accordance with an embodiment.

At step 610, information indicating changes to a mixture during transport is received from a transport module. For example, master database module 11 may receive an alert from transport module 15 indicating that changes occurred to a mixture during transport of the mixture. Referring to block 620, a determination is made whether the changes are within acceptable tolerances. If the changes are within acceptable tolerances, the method proceeds to step 630. At step 630, the product/mixture is delivered to the producer's and/or customer's site. If the changes are not within acceptable tolerances, the method proceeds to step 640. At step 640, an alert is transmitted to the producer and/or customer and the product/mixture is delivered. Alerts to the producer and/or customer may be issued by alert module 17, or by master database module 11. At step 650, the variances of actual versus theoretical recipe cost and performance factors is stored at master database module 11. In other embodiments, the information concerning changes is not stored.

In the illustrative embodiment, the producer's and/or the customer's site or location is equipped with site module 16, which transmits to master database module 11, by communication line 25, information about the mixture of product that is delivered to the site. Such information may include, for example, information indicating the actual performance of the product/mixture as delivered. Master database module 11 stores the actual performance data. Master database module 11 may provide to the producer and/or customer a report concerning various aspects of the actual product delivered.

Site module 16 may also receive alerts from alert module 17 by communication line 35.

In the illustrative embodiment, alert module 17 is a module separate from master database module 11. However, in other embodiments, the functions of alert module 17 may be performed by master database module 11.

Alert module 17 may also transmit final reports concerning the products to site module 16, thereby enabling the seller and the producer and/or customer a way of managing the product. Feedback provided throughout the production process, as illustrated above, advantageously allows the producer and/or customer and the manufacturer to manage costs and quality of the products.

The alert functions described above facilitate the process of managing production and costs. In response to any alert, the producer and/or customer or the manufacturer has the ability to make a decision not to continue the production or delivery of the product because the product has fallen outside of acceptable tolerances.

While the illustrative embodiment of FIG. 1A includes only one production module, one transport module, one site module, one alert module, one purchase module, one input module, and one sales module, in other embodiments, a system may include a plurality of production modules, a plurality of transport modules, a plurality of site modules, a plurality of alert modules, a plurality of purchase modules, a plurality of input modules, and/or a plurality of sales modules. For example, in an illustrative embodiment, suppose that a system used by a company in the ready mix concrete industry includes a master database module 11 residing and operating on a server computer located in Pittsburgh, Pa. The company's sales force may be located in Los Angeles, Calif., where the sales module 13 resides and operates (on a computer). Suppose that a sale is made in Los Angeles, and the purchase order specifies a site in San Francisco, Calif. Thus, master database module 11 may output an order to a production module 14 which is located at a ready mix production facility in the vicinity of San Francisco, Calif. Suppose further that a single production facility in the vicinity of San Francisco cannot handle the volume of the concrete that is needed for the job site in San Francisco. In such a case, master database module 11 may output to a plurality of production facilities, each having a production module 14, the necessary orders for fulfillment. Thus, the system includes a plurality of production modules, one in each of the various production facilities. The production facilities produce the specified mixture and transport the ready mix concrete in a plurality of trucks to the producer site and/or customer site in San Francisco. Each truck has a transport module associated therewith. Suppose that one or more of the production modules does not have the specific components that were specified in the purchase order for the concrete. Thus, adjustments may be made at the production facility to the concrete mixes, and information concerning such adjustments are transmitted back to the master data base module 11. Such adjustment information may be processed in accordance with the steps illustrated in FIGS. 3 and/or 4.

During the transport of the ready mix concrete from the various production facilities, the transport modules 15 in each of the trucks transmit to the master database module 11 any changes made to the mixture. The master database module 11 may then perform the method described FIG. 6. In a similar manner, master database module 11 is informed of any changes occurring during production and, as a result, master database module 11 may perform the method described in FIG. 5.

Finally, the concrete is delivered to the producer and/or customer site in San Francisco and information concerning the delivered concrete may be transmitted to the master database module 11. The site module 16 may also be used to provide the master database module 11 with information relating to one or more of the following: measurements of the actual heat of hydration taken from the fresh state through the hardening process, strength characteristics of the concrete after it is hardened, etc. Advantageously, the feedback provided in this manner to master database module 11 from the various modules enables the producer and/or customer of the concrete in Los Angeles to monitor, on a real time basis, the concrete poured at the producer's and/or customer's construction site in San Francisco, without having to physically be in San Francisco.

Furthermore, the producer and/or customer in Los Angeles may monitor, on a real time basis, costs associated with the concrete which is delivered to the site in San Francisco.

Furthermore, the ready mix concrete producer may associate, in real time, variances in one or more parameters relating to the concrete's performance from specified expectations, and correlate such variances to actual batched versus the expected specified recipe. These capabilities advantageously allow the maintenance of consistent, low standard deviation production batching from a mixture recipe baseline, and production of concrete that has a consistent strength performance with a low standard deviation.

Changes in materials may impact a producer's cost of materials (COM). An increase in COM can in turn impact the producer's profitability. In many instances, any increase (in percentage terms) in the COM results in a much greater impact on profitability (in percentage terms). For example, it has been observed that, using ACI 318 statistical quality criteria, it can be demonstrated that each 1% cement or water variance from the mix design theoretical recipe value can result in a cost impact of around $0.2 to $0.4 per cubic yard. Since such variances can typically range from 2% to 10%, the cost impact may range from $0.4 to $10 per cubic yard annually. This cost impact is a very large percentage of the average profit of a producer in the ready mix concrete industry, which is on the order of $1/cubic yard.

Advantageously, the integrated production management system and method described herein enables a producer to manage the overall production system for ready mix concrete, and allows greater control over changes that may impact the producer's costs (and profits). The integrated production management system and method described herein also provides a producer and/or customer increased control over the producer's and/or customer's construction site.

For convenience, several examples relating to the ready mix concrete industry are described below.

Concrete Construction & Manufacturing/Production Examples

Examples are provided for three different market segments:
  A. Ready Mix Concrete
  B. Contractors
  C. State Authorities Closed Loop Solutions (CLS) Overview Set forth below is a discussion of a closed loop solution (CLS) in accordance with an embodiment. Each operation has a set of theoretical goals and obtained physical or actual results. Practically all operational IT architectures include a collection of disparate information systems that need to work together.

CLS is an information technology solution that enforces:

Data Integrity across linked or associated disparate information systems (Ready Mix Example: Mix costs & formulae to have data integrity or be the same across mix management, sales, dispatch, batch panels, and business systems)

Closed Loop Data Integrity, meaning that the operations' goals and its actual physical results match within tolerances (concrete batch & mix BOMs (Bill of Materials) closely match)

Four Types of CLS for Different Market Segments
  I. Ready Mix Producers: Closed Loop Integration (CLI):
    1) CLI has been implemented as a CLS application for many Ready Mix Producers in the US and Canada.
    2) CLI applications are real-time, two-way interfaces with production systems
    3) One of the main purposes of CLI is to enforce data integrity between batches in trucks and parent mix designs; CLI closes the loop between the mix management and production cycles.
  II. Ready Mix Producers: Closed Loop Sales Management (CLSM):
    1) CLSM is a CLS application for Ready Mix Producers in the US and Internationally.
    2) One of the main purposes of Closed Loop Sales Management is a project-based workflow for the industry sales process, tracking actual versus target profitability, This application closes the loop between actual and target profitability factors. One benefit is maximization of profitability.
  III. Contractors: Closed Loop Quality & Cost:
    1) The solution for the Contractor market segment is similar to the Closed Loop Quality application, except that it also includes concrete delivered cost management
    2) One of the main purposes of Closed Loop Quality & Cost is a real time enforcement of placed concrete obtained specs and performance to the applicable project specs, plus monitoring placed versus as-purchased cost—This application closes the loop between both the delivered versus specified project concrete performance and cost.
  IV. State Authorities: Closed Loop Quality:
    1) This solution is intended for the Authorities market segment as a modification of the CLI production driven Ready Mix application
    2) One of the main purposes of Closed Loop Quality is a real time enforcement of placed concrete obtained specs and performance to the applicable project specs. This application closes the loop between the delivered versus specified project concrete performance.

Set forth below are several application examples.

[A] Ready Mix Concrete Producers—CLS Type: Closed Loop Integration for Real Time, Production Level, Consolidated Mix Management
  I. Ready Mix Needs Include:
    1) Consolidate critical mix, cost, and quality data in a single database
    2) Minimize quality issues
    3) Utilize materials efficiently
    4) Real time information visibility—customized by user profile
  II. Ready Mix Economics & its Management:
    1) 50% to 70% of cost of business (COB) is cost of materials (COM)
    2) A 1% increase in COM can translate to more than a 10% profitability drop
    3) Thus, production level materials management is important to profitability.

TABLE 1

| Item | per Cyd |
|---|---|
| Net Profit % | 5.0% |
| Price | $85.00 |
| Cost of Business (COB) | $80.75 |
| Net Profit | $ 4.25 |

TABLE 1-continued

| Item | per Cyd |
|---|---|
| Cost of materials (COM) as % of | |
| COB | 55.0% |
| COM | $ 44.41 |
| 1% increase in COM | $ 0.44 |
| Change in COB | $ 0.44 |
| Change in Net profit | ($ 0.44) |
| % change in net profits per % COM | −10.5% |

Table 1 shows the relationship between COM and profitability.

III. To Meet Quality, Materials Utilization, and Information Visibility Needs:
1) Optimize mixes to performance and cost goals in a consolidated database using mix optimization tools.
2) Implement closed loop integration (CLI) for the production level management of optimized mixes; may use alerts application for alert notification of out-of-tolerance batches.
3) Use CLI to ship concrete to mix baselines for implementing production level, real time cost and quality management. The CLI system in effect uses mixes as a budgetary tool for both quality and cost control.

[B] CONTRACTORS—CLS TYPE: Closed Loop Cost & Quality

TABLE 2

Table 2 illustrates advantages of real time, consolidated costs and quality management.

Components of $0.5 to $ pcy/yr:

- Manage Yield — 1% over batching: $0.50 pcy annually
- Optimize Mixes — 1% over cementing: $0.25 pcy annually
- Achieve Low Variance, Consistent Quality — 1% Coefficient of Variation increase = $0.4 to $0.8 pcy anually
- Use Hi-Efficiency Constituents — 1% over cementing: $0.25 pcy annually I. Contractor Concrete Related Needs:
1) Consolidate aspects of concrete related data across all projects in a single database.
2) Ensure obtained quality meets specifications in order to minimize quality issues and avoid project delays
3) Track & match up contracted volume & cost versus actual delivered volumes & costs
4) Real time information visibility—customized by user profile II. Basic Contractor Economics:
1) Concrete cost and quality related schedule delay can amount to around 16% in profit loss.
2) Thus, production level concrete quality and cost management are important to contractor profitability III. Closed Loop Solution to Meet Quality, Cost Management, and Information Visibility Needs:
1) Implement Closed Loop Cost & Quality (CLCQ) for the real time management of obtained versus a) specified performance and recipe factors, b) Actual versus budgeted cost and volume factors; use an alert system for alert reporting & notification of out-of-tolerance monitored variables.
2) For each project, consolidate quality & engineering team, tests, concrete deliveries & poured volumes, cost, project mix designs and specs, project documents, in a single unified database; do this across all of the contractor's projects in one or more countries—makes possible sharing and learning cross project experience
3) Use CLCQ to maintain quality, enforce meeting specs in real time, enforce budgetary cost & volume goals, and create real time, production level visibility including alerting reports.

Contractor Concrete Economics
1. 10% to 20% of a project cost is concrete cost; in some regions/countries this number may be close to 20%
2. Since contractor margin is on the order of 1% to 5%, a 1% change in concrete cost may result on average in about a 8% profitability drop
3. Additionally, it is import to avoid schedule slippage due to quality issues:
    1. Each delay day may represent roughly 0.2% to 1% of total project cost—assume 0.2%
    2. Each delay day due to concrete quality for a $100 mil project may cost $200,000, or roughly an 8% drop in profitability
4. Concrete cost and quality schedule delay may total to around 16% in profit loss.
5. Thus, production level quality and cost management are important to contractor profitability, and the related cost factors can be managed by a closed loop production system

[C] State Authorities—CLS Type: Closed Loop Quality
For real time, consolidated concrete quality management
I. State Authority Key Concrete Related Needs:
1) Consolidate all aspects of concrete related data across all projects in a single database including mix specifications and designs, batch data, and test data, as well as the required QC/QA plan
2) Make possible data access, input, and sharing cross projects, and by project-based entities
3) Ensure obtained quality and performance meet specifications in order to minimize quality issues and avoid project delays
4) Track & match up contracted costs & volumes versus actual values
5) Real time information visibility—customized by project & user profile II. State Authority Economics—Costs of Poor Quality and Reduced Longevity:
1) Assume: $100 mil structure; 30,000 m3 concrete @ $100/m3 delivered
2) Concrete quality related schedule delay costs may amount to $70,000/delay day
3) Poor quality future repair costs may amount to $120,000 per 1% increase in strength CV
4) If the building service life is reduced by one year due to poor quality, then a revenue loss of around $1.25 mil. may result
5) Thus, production level, real time quality and cost management is important to the owner economics 6) These significant cost factors may be managed by the closed loop system III. To Meet Quality, Cost Management, and Information Visibility Needs:
1) For each project, consolidate concrete production volumes, project mix designs and specifications, and tests in a single database. Also, include the QA/QC plan
2) Make possible data access, input, and sharing across projects. Restrict access by project and user profile. Include: State officials, Engineers/Architects, Contractors, Test Labs, and Ready Mix Producers
3) Implement Closed Loop Quality (CLQ) for the real time management of obtained versus specified performance and recipe factors; use an alert system for alert notification of out-of-tolerance batches. Reconcile tests against QC/QA plan.
4) Create real time, production level visibility including alerting reports.

State Authority Concrete Economics
Assume a $100 Mil Structure Requiring 30,000 M3 Concrete @ an Average of $100/m3 Delivered.
1. Suppose that:
 1) The owner wishes to amortize the $100 mil cost during a 10-year period, which amounts to a monthly rate of $833,333, and wishes to lease the building for the same amount
 2) The owner takes a 30 year mortgage @ 5% interest amounting to a monthly payment of $535 k.
 3) This leaves a monthly cash flow of around $300 k, or $3.6 mil/yr
2. Poor Quality Cost Factors include:
 1) Each delay day may result in an opportunity cost of roughly $70,000, or around 2% of annual cash flow
 2) If poor quality goes unnoticed, and is repaired at a later date, each 1% increase in the 28-day strength coefficient of variation from its ACI 318 design base may result in future repair costs of $120 k, or around 7% of the annual cash flow
 3) If poor quality goes unnoticed, and is not treated, each one year reduction in the service life may amount to $3.6 in lost revenues Annualized over the first 10 years, this changes the monthly cash flow to around a loss of ($60,000)
3. Concrete poor quality costs without a reduction in the service life can amount to around 9% of cash flow; with service life reduction, the cash flow can turn negative.
4. Thus, production level quality management is important to the owner economics, and the related cost factors can be managed by the closed loop system In accordance with another embodiment, a mixture formulation is maintained by master database module 11. Localized versions of the mixture formulation intended for use at respective production facilities are generated, stored, and provided to the respective production facilities, as necessary. At a respective production facility, the mixture is produced based on the localized version of the mixture formulation.

Figure 7A:
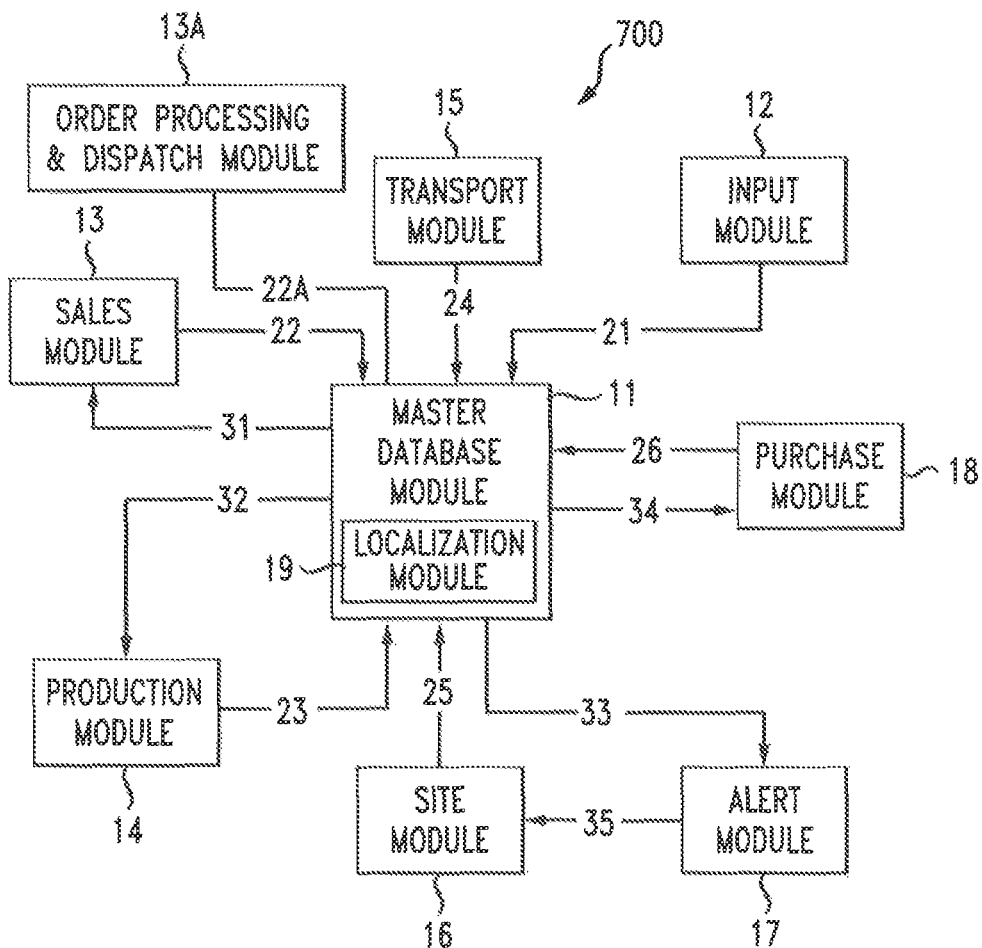
FIG. 7A shows a production management system in accordance with another embodiment.

FIG. 7A shows a production management system 700 in accordance with another embodiment. Similar to product management system 10 of FIG. 1A, product management system 700 includes a master database module 11, an input module 12, a sales module 13, an order processing & dispatch module 13A, a production module 14, a transport module 15, a site module 16, an alert module 17, and a purchase module 18.

A localization module 19 resides and operates in master database module 11. For example, master database module 11 and localization module 19 may comprise software that resides and operates on a computer.

Localization module 19 generates one or more localized versions of a mixture formulation for use at respective production facilities where a mixture may be produced. Localization module 19 may, for example, access a mixture formulation maintained at master database module 11, analyze one or more local parameters pertaining to a selected production facility, and generate a modified version of the mixture formulation for use at the selected production facility. Localization module 19 may generate localized versions of a particular mixture formulation for one production facility or for a plurality of production facilities. For example, master database module 11 may generate localized versions of a mixture formulation for every production facility owned or managed by a producer. Likewise, localization module 19 may generate localized versions of selected mixture formulations maintained by master database module 11, or may generate localized versions for all mixture formulations maintained by master database module 11.

Figure 7B:
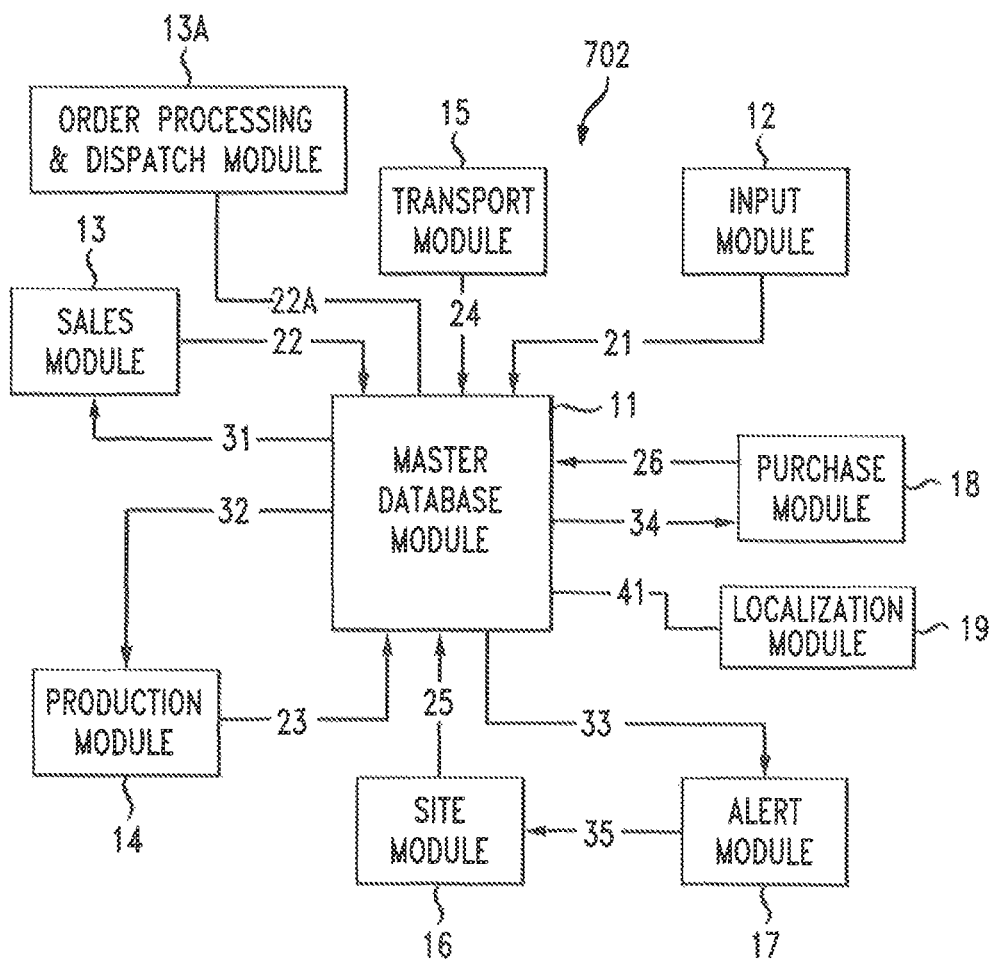
FIG. 7B shows a production management system in accordance with another embodiment.

FIG. 7B shows a production management system 702 in accordance with another embodiment. Similar to product management system 10 of FIG. 1A, product management system 702 includes a master database module 11, an input module 12, a sales module 13, an order processing & dispatch module 13A, a production module 14, a transport module 15, a site module 16, an alert module 17, and a purchase module 18. In the embodiment of FIG. 7B, localization module 19 is separate from master database module 11 and is connected to master database module 11 by a link 41. For example, master database module 11 may reside and operate on a first computer and localization module 19 may reside and operate on a second computer remote from master database module 11. For example, localization module 19 may reside and operate on a second computer located at a production facility. Localization module 19 may communicate with master database module 11 via a network such as the Internet, or via another type of network, or may communicate via a direct communication link.

Figure 7C:
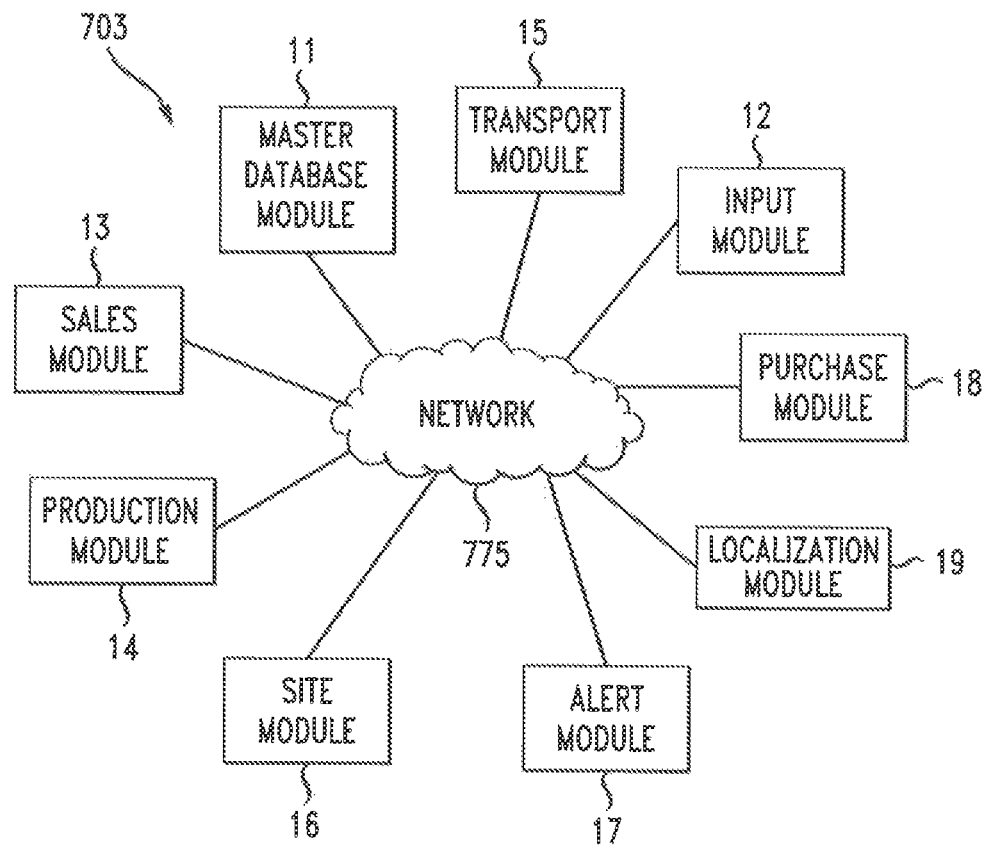
FIG. 7C shows a production management system in accordance with another embodiment.

FIG. 7C shows a production management system 703 in accordance with another embodiment. Product management system 703 includes a master database module 11, an input module 12, a sales module 13, a production module 14, a transport module 15, a site module 16, an alert module 17, a purchase module 18, and a localization module 19. Modules 11-19 are connected to a network 775. Modules 11-19 communicate with each other via network 775. For example, various modules may transmit information to master database 11 via network 775.

Network 775 may comprise the Internet, for example. In other embodiments, network 775 may comprise one or more of a number of different types of networks, such as, for example, an intranet, a local area network (LAN), a wide area network (WAN), a wireless network, a Fibre Channel-based storage area network (SAN), or Ethernet. Other networks may be used. Alternatively, network 775 may comprise a combination of different types of networks.

Figure 8:
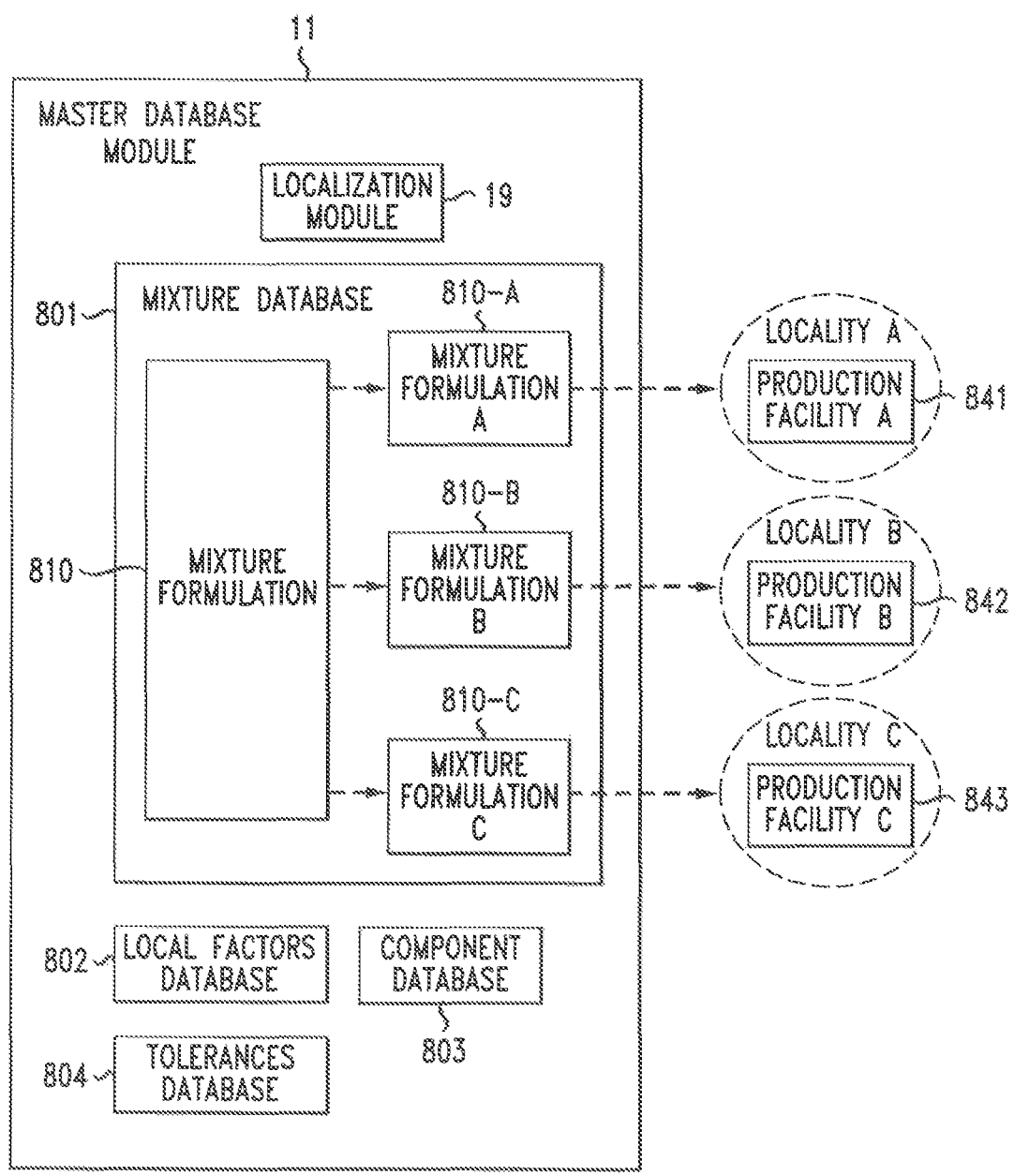
FIG. 8 illustrates a system for the management of localized versions of a mixture formulation in accordance with an embodiment.

FIG. 8 illustrates a system for the management of localized versions of a mixture formulation in accordance with an embodiment. In the illustrative embodiment of FIG. 8, master database module 11 comprises localization module 19, a mixture database 801, a local factors database 802, a components database 803, and a tolerances database 804. A mixture formulation 810 associated with a particular mixture is maintained in mixture database 801. While only one mixture formulation is shown in FIG. 8, it is to be understood that more than one mixture formulation (each associated with a respective mixture) may be stored by master database module 11.

Master database module 11 is linked to several production facilities, as shown in FIG. 8. In the illustrative embodiment, master database module 11 is in communication with Production Facility A (841), located in Locality A, Production Facility B (842) located in Locality B, and Production Facility C (843), located in Locality C. While three production facilities (and three localities) are shown in FIG. 8, in other embodiments more or fewer than three production facilities (and more or fewer than three localities) may be used.

In the embodiment of FIG. 8, local factors database 802 stores local factor data relating to various production facilities, including, for example, local availability information, local cost information, local market condition information, etc. Localization module 19 may obtain local factor data based on the information in local factors database 802. Components database stores information pertaining to various components of product mixtures, such as, for example, technical information concerning various components, costs of various components, etc. Tolerances database 804 stores information defining tolerances related to various components and mixtures.

In the illustrative embodiment, localization module 19 accesses mixture formulation 810 and generates a localized version for Production Facility A (841), shown in FIG. 8 as Mixture Formulation A (810-A). Localization module 19 generates a localized version for Production Facility B (842), shown in FIG. 8 as Mixture Formulation B (810-B). Localization module 19 also generates a localized version for Production Facility C (843), shown in FIG. 8 as Mixture Formulation C (810-C). Mixture Formulation A (810-A), Mixture Formulation B (810-B), and Mixture Formulation C (810-C) are stored at master database module 11.

In order to generate a localized version of a mixture formulation for a particular production facility, localization module 19 accesses local factors database 802 and analyzes one or more local factors pertaining to the particular production facility. For example, localization module 19 may analyze one or more local availability factors representing local availability of components in the mixture formulation, one or more local market condition factors representing characteristics of the local market, one or more local cost factors representing the cost of obtaining various components in the local market, etc.

Localization module 19 may modify a mixture formulation based on a local factor. For example, if a local market factor indicates a strong preference for a product having a particular feature (or a strong bias against a certain feature), localization module 19 may alter the mixture formulation based on such local market conditions. If a particular component is not available in a local market, localization module 19 may alter the mixture formulation by substituting an equivalent component that is locally available. Similarly, if a particular component is prohibitively expensive in a particular locality, localization module 19 may reduce the amount of such component in the mixture formulation and/or replace the component with a substitute, equivalent component.

It is to be understood that FIG. 8 is illustrative. In other embodiments, master database module 11 may include components different from those shown in FIG. 8. Mixtures and local factors may be stored in a different manner than that shown in FIG. 8.

Figure 9:
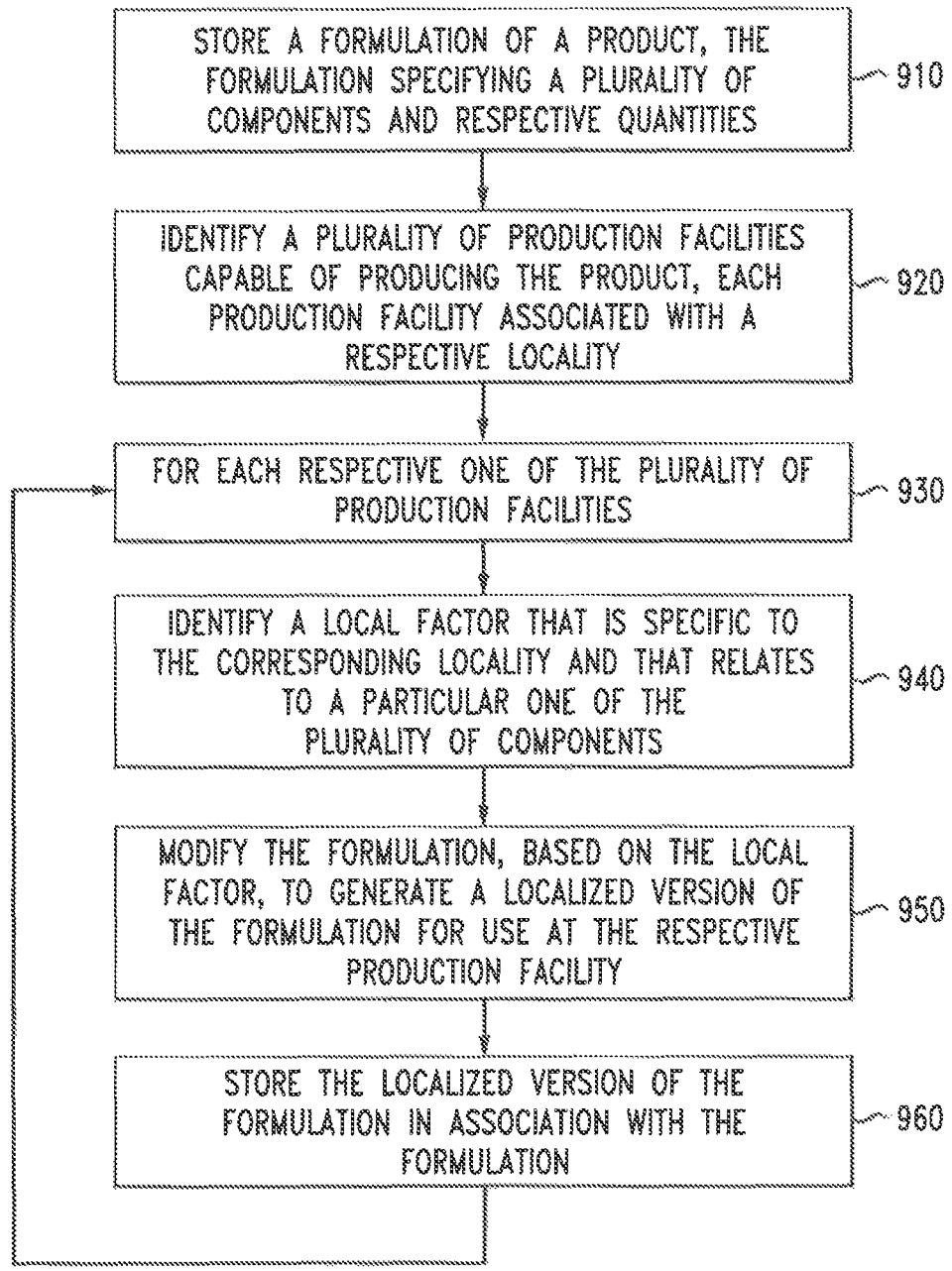
FIG. 9 is a flowchart of a method of generating localized versions of a mixture formulation in accordance with an embodiment.
Figure 10:
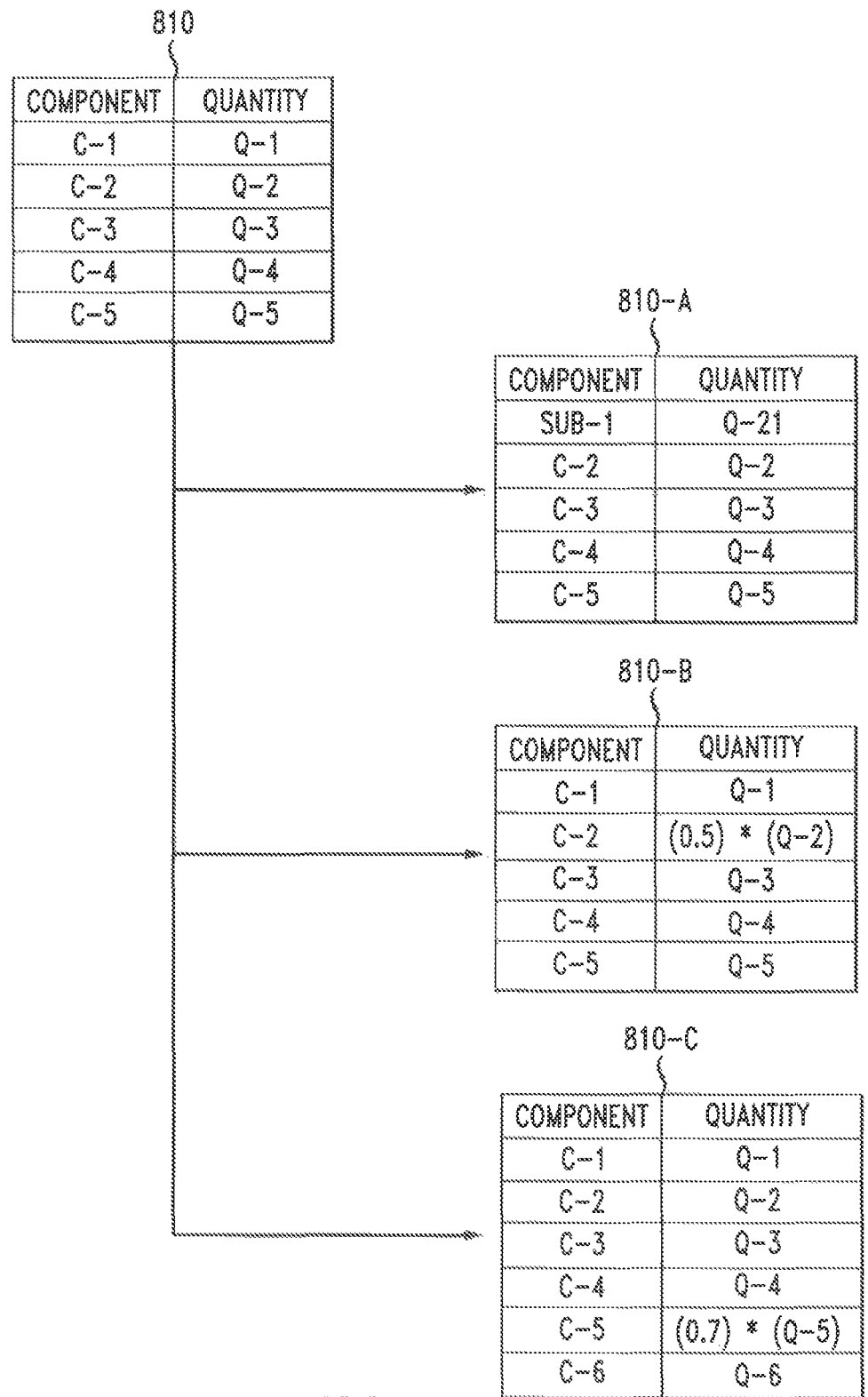
FIG. 10 shows a mixture formulation and several localized versions of the mixture formulation in accordance with an embodiment.

FIG. 9 is a flowchart of a method of generating localized versions of a mixture formulation in accordance with an embodiment. The method presented in FIG. 9 is discussed with reference to FIG. 10. FIG. 10 shows mixture formulation 810 and several corresponding localized versions of the mixture formulation in accordance with an embodiment.

At step 910, a formulation of a product is stored, the formulation specifying a plurality of components and respective quantities. As discussed above, mixture formulation 810 is stored at master database module 11. Referring to FIG. 10, mixture formulation 810 specifies the following components and quantities: C-1, Q-1; C-2, Q-2; C-3, Q-3; C-4, Q-4; and C-5, Q-5. Thus, for example, mixture formulation 810 requires quantity Q-1 of component C-1, quantity Q-2 of component C-2, etc. Mixture formulation 810 may also specify other information, including a method to be used to manufacture the mixture.

At step 920, a plurality of production facilities capable of producing the product are identified, each production facility being associated with a respective locality. In the illustrative embodiment, localization module 19 identifies Production Facility A (841) in Locality A, Production Facility B (842) in Locality B, and Production Facility C (843) in Locality C.

Referring to block 930, for each respective one of the identified production facilities, a series of steps is performed. At step 940, a local factor that is specific to the corresponding locality and that relates to a particular one of the plurality of components is identified. Localization module 19 first accesses local factors database 802 and examines local factors relating to Locality A and Production Facility A (841). Suppose, for example, that localization module 19 determines that in Locality A, component C-1 is not readily available.

At step 950, the formulation is modified, based on the local factor, to generate a localized version of the formulation for use at the respective production facility. In the illustrative embodiment of FIG. 10, localization module 19 substitutes an equivalent component SUB-1 for component C-1 to generate a localized version 810-A of mixture 810. Localized version 810-A is intended for use at Production Facility A (841).

At step 960, the localized version of the formulation is stored in association with the formulation. In the illustrative embodiment, localized version 810-A is stored at master database module 11 in association with mixture formulation 810.

Referring to FIG. 9, the routine may return to step 930 and repeat steps 930, 940, 950, and 960 for another production facility, as necessary. Suppose, for example that localization module 19 determines that in Locality B (associated with Production Facility B (842)), local purchasers prefer a product with less of component C-2. Localization module 19 thus reduces the quantity of component C-2 in the respective localized version 810-B of mixture 810, as shown in FIG. 10. In particular, the amount of component C-2 in localized version 810-B is (0.5)*(Q-2). Localized version 810-B is intended for use at Production Facility B (842). Localized version 810-B is stored at master database module 11 in association with mixture formulation 810, as shown in FIG. 8.

Suppose that localization module 19 also determines that in Locality C (associated with Production Facility C (843)), local purchasers prefer a product with an additional component C-6. Localization module 19 further determines that component C-6 is an equivalent of component C-5, but is of lower quality. To accommodate local market conditions, localization module 19 reduces the quantity of component C-5 to (0.7)*(C-5) and also adds a quantity Q-6 of component C-6 to generate a localized version 810-C of mixture 810, as shown in FIG. 10. Localized version 810-C is intended for use at Production Facility C (843). Localized version 810-C is stored at master database module 11 in association with mixture formulation 810, as shown in FIG. 8.

Master database module 11 may subsequently transmit one or more of the localized versions 810-A, 810-B, 810-C to Production Facilities A, B, and/or C, as necessary. For example, suppose that an order is received for Mixture Formulation 810. Suppose further that Production Facility A and Production Facility B are selected to produce the mixture. Master database module 11 accordingly transmits the localized version Mixture Formulation A (810-A) to Production Facility A (841). Mixture Formulation A (810-A) is stored at Production Module 14. Master database module 11 also transmits the localized version Mixture Formulation B (810-B) to Production Facility B (842). Mixture Formulation B (810-B) is stored at a respective production module (not shown) operating at Production Facility B (842).

The mixture is then produced at each designated production facility based on the respective localized version of the mixture formulation. In the illustrative embodiment, the mixture is produced at Production Facility A (841) in accordance with the localized version Mixture Formulation A (810-A)). The mixture is produced at Production Facility B (842) in accordance with the localized version Mixture Formulation B (810-B).

In accordance with another embodiment, master database module 11 from time to time updates the master version of a mixture formulation (stored at master database module 11). Master database module 11 also monitors versions of the mixture formulation maintained at various production facilities. If it is determined that a version of the mixture formulation stored at a particular production facility is not the same as the master version of the mixture formulation, an alert is issued and the local version is synchronized with the master version. For purposes of the discussion set forth below, any version of a mixture formulation that is stored at master database module 11 may be considered a "master version" of the mixture formulation.

Figure 11A:
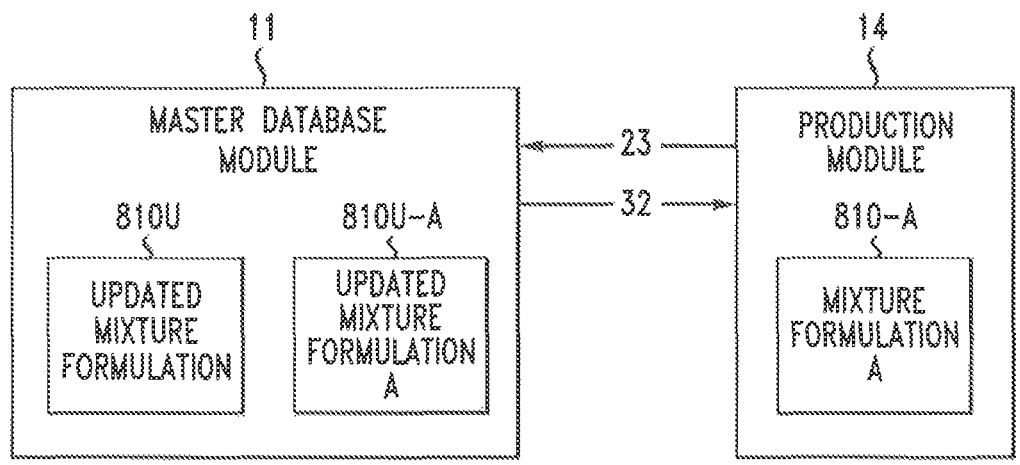
FIGS. 11A-11B illustrate a system for synchronizing versions of a mixture formulation in accordance with an embodiment.

In an illustrative embodiment, suppose that master database module 11 updates Mixture Formulation 810. This may occur for any of a variety of reasons. For example, the cost of one of the components in Mixture Formulation 810 may increase substantially, and the particular component may be replaced by an equivalent component. Referring to FIG. 11A, the updated formulation is stored at master database module 11 as Updated Mixture Formulation 810U.

Master database module 11 also generates localized versions of the updated mixture formulation. Thus, for example, master database module 11 generates an updated localized version of Mixture Formulation 810U for Production Facility 841 (in Locality A). The updated localized version of is stored at master database module 11 as Updated Mixture Formulation A (810U-A), as shown in FIG. 11A.

Figure 12:
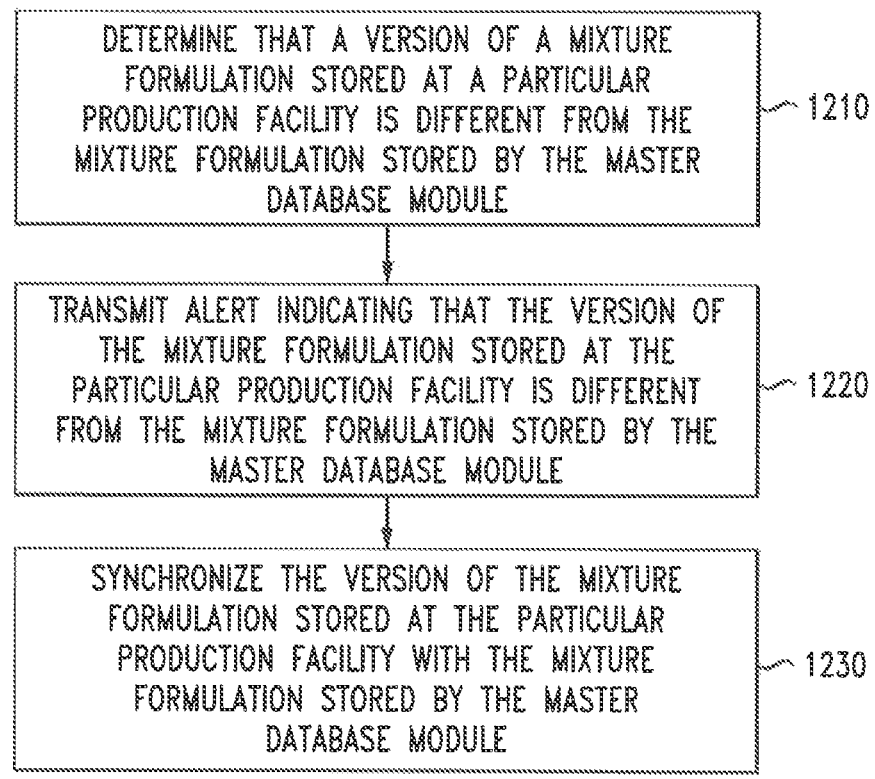
FIG. 12 is a flowchart of a method of synchronizing a localized version of a mixture formulation with a master version of the mixture formulation in accordance with an embodiment.

Master database module 11 identifies one or more production facilities that store a localized version of Mixture Formulation 810, and notifies each such production module that Mixture Formulation 810 has been updated. If a production module does not have the correct updated version of the mixture formulation, the localized version must be synchronized with the updated master version stored at master database module 11. FIG. 12 is a flowchart of a method of synchronizing a localized version of a mixture formulation with a master version of the mixture formulation in accordance with an embodiment.

In the illustrative embodiment, certain aspects of production at Production Facility A (841) are managed by production module 14. For example, production module 14 may operate on a computer or other processing device located on the premises of Production Facility A (841).

At step 1210, a determination is made that a mixture formulation stored at a particular production facility is different from the mixture formulation stored by the master database module. For example, master database module may communicate to production module 14 (operating at Production Facility A (841)) that Mixture Formulation A (810-A) has been updated. Production module 14 determines that its current localized version of the mixture formulation is not the same as Updated Mixture Formulation A (810U-A).

At step 1220, an alert is transmitted indicating that the version of the mixture formulation stored at the particular production facility is different from the mixture formulation stored by master database module 11. Accordingly, production module 14 transmits an alert to master database module 11 indicating that its local version of the mixture formulation is not the same as the updated version stored at master database module 11.

Figure 11B:
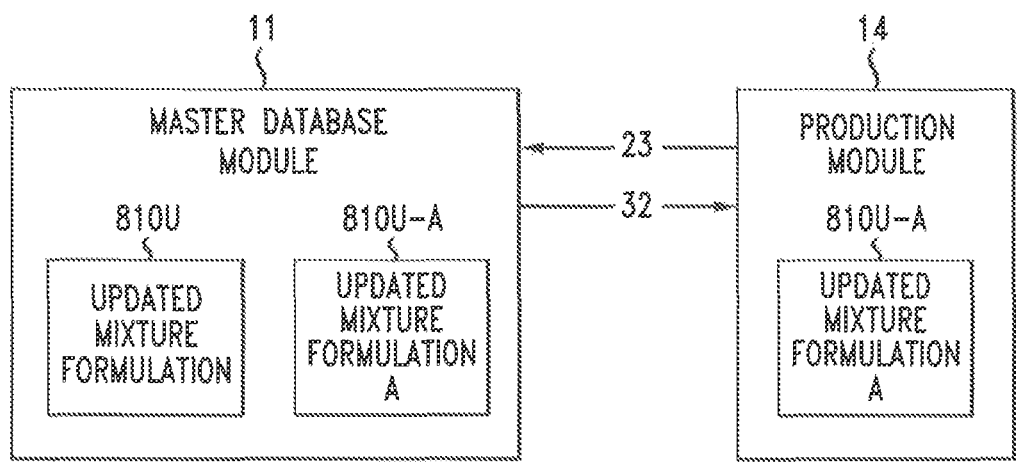

At step 1230, the version of the mixture formulation stored at the particular production facility is synchronized with the mixture formulation stored at the master database module 11. In response to the alert, master database module 11 provides production module 14 with a copy of Updated Mixture Formulation A (810U-A). Production module 14 stores Updated Mixture Formulation A (810U-A), as shown in FIG. 11B.

Various methods and system described above may be used in an integrated closed-loop production system to manage a production system. In accordance with an embodiment, a method of managing a closed-loop production system is provided. Master database module 11 provides to sales module 13 descriptions, prices, and other information relating to a plurality of available mixtures, enabling sales module 13 to offer several options to potential producers and/or customers. Specifically, master database module 11 provides information relating to a plurality of concrete mixtures. Sales module 13 may present the information to a producer and/or customer in the form of a menu, as discussed above with reference to FIG. 1B.

Suppose now that a producer and/or customer considers the available mixtures and selects one of the plurality of concrete mixtures. Suppose further that the producer and/or customer submits an order for the selected mixture, specifying parameters such as quantity, date and place of delivery, etc. For illustrative purposes, suppose that the producer and/or customer selects the mixture associated with mixture formulation 810 (shown in FIG. 8) and specifies a delivery site located in or near Locality A (also shown in FIG. 8). Master database module 11 utilizes a closed-loop production system such as that illustrated in FIG. 1A to manage the sale, production and delivery of the selected mixture to the producer and/or customer.

Figure 13A:
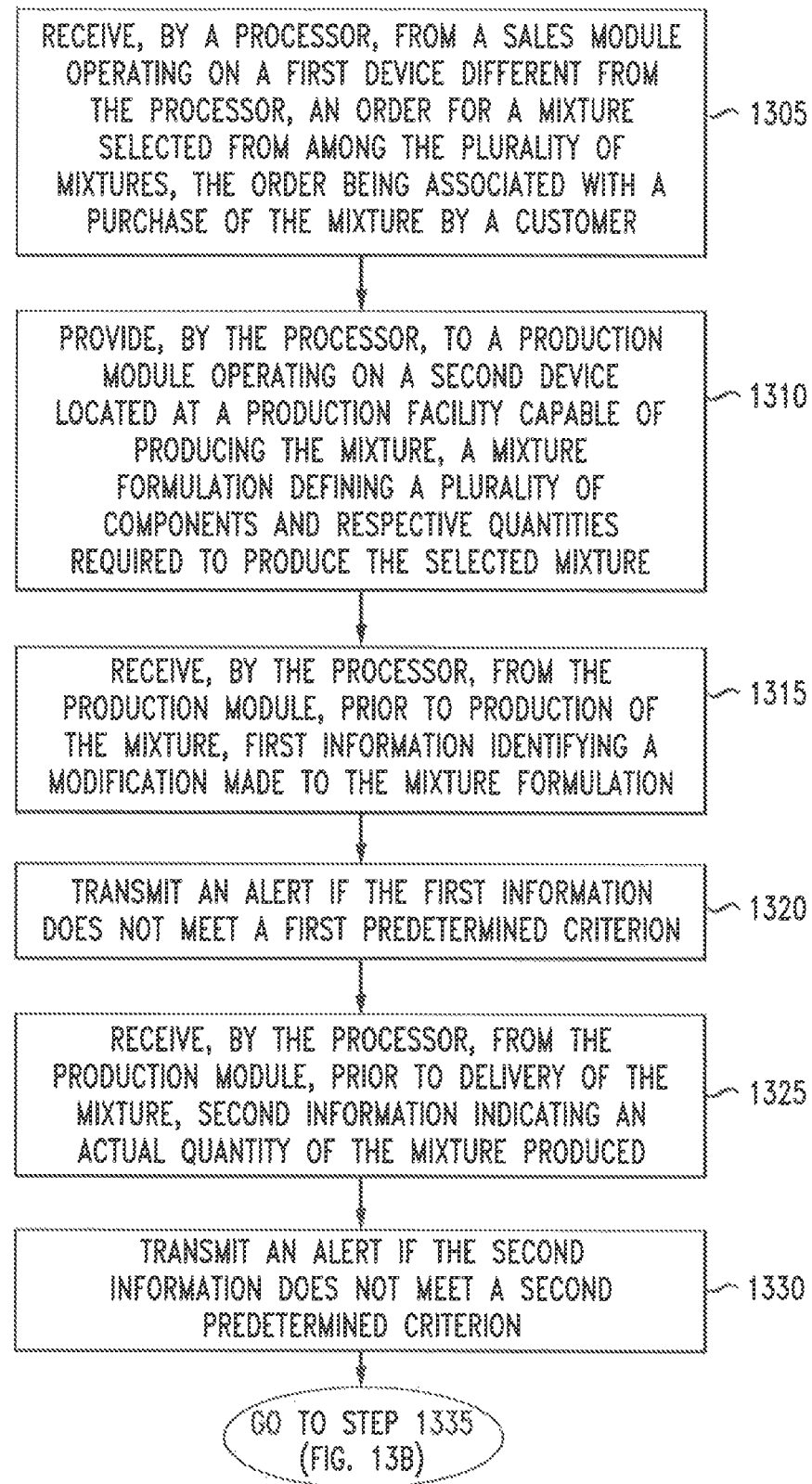
FIGS. 13A-13B comprise a flowchart of a method of managing a closed-loop production system in accordance with an embodiment.
Figure 13B:
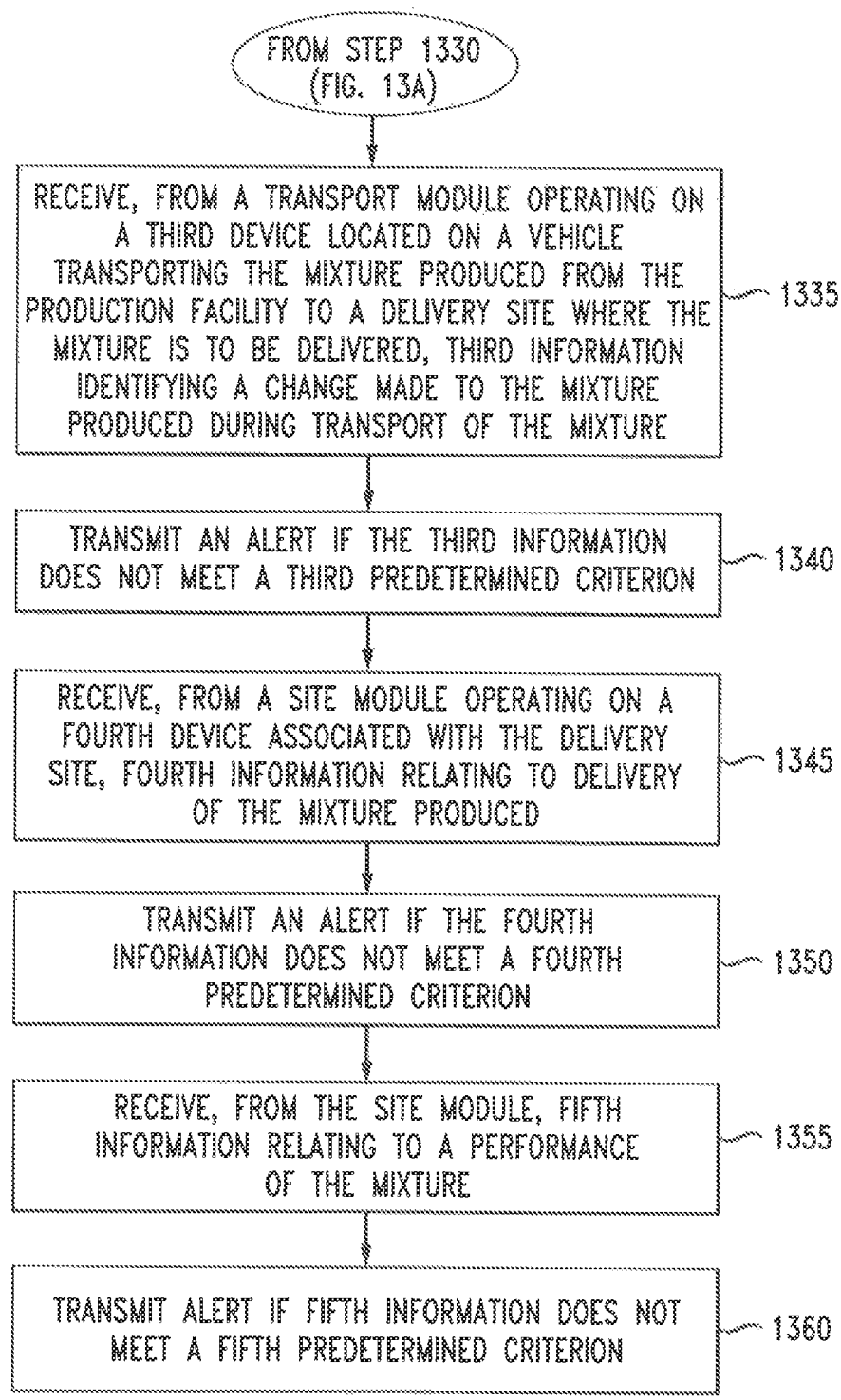

FIGS. 13A-13B comprise a flowchart of a method of managing a closed-loop production system in accordance with an embodiment. At step 1310, an order for a mixture selected from among the plurality of mixtures is received, by a processor, from a sales module operating on a first device different from the processor, the order being associated with a purchase of the mixture by a producer and/or customer. In the illustrative embodiment, sales module 13 transmits the order for the selected concrete mixture to master database module 11. The order specifies the selected mixture and other information including quantity, date and place of delivery, etc. Master database module 11 receives the order for the selected concrete mixture from sales module 13.

At step 1310, a mixture formulation defining a plurality of components and respective quantities required to produce the selected mixture is provided, by the processor, to a production module operating on a second device located at a production facility capable of producing the mixture. Accordingly, master database module 11 identifies one or more production facilities capable of producing the selected mixture. Production facilities may be selected based on a variety of factors. For example, master database module 11 may select one or more production facilities that are located near the delivery site specified in the order. In the illustrative embodiment, master database module 11 selects Production Facility A (841) due to the fact that the producer's and/or customer's delivery site is located in or near Locality A. It is to be understood that more than one production facility may be selected and used to produce a mixture to meet a particular order.

Master database module 11 transmits Mixture Formulation A (810-A) (or any updated version thereof) to Production Facility A (841). Production module 14 manages and monitors the production process. In the illustrative embodiment, production module 14 determines that a particular component of mixture formulation A (810-A) is currently unavailable and replaces the component with a known equivalent. Production module 14 accordingly transmits an alert to master database module 11 indicating that the component has been replaced. An alert may then be provided to the producer and/or customer, as well. Production of the selected mixture proceeds. In one embodiment, the alert may be transmitted in real time (e.g., within a specified time period after production module 14 receives the information).

At step 1315, first information identifying a modification made to the mixture formulation is received, by the processor, from the production module, prior to production of the mixture. Master database module 11 receives the alert from production module 14.

At step 1320, an alert is transmitted if the first information does not meet a first predetermined criterion. If the modification does not meet specified requirements, master database module 11 transmits an alert to the producer and/or customer. In one embodiment, the alert is transmitted in real time.

In the illustrative embodiment, a quantity of the mixture actually produced at Production Facility A (841) differs from the quantity specified in the order. Production module 14 transmits an alert to master database module 11 and to alert module 17 indicating that the quantity actually produced differs from the quantity ordered. The alert may be transmitted in real time. At step 1325, second information indicating an actual quantity of the mixture produced is received, from the production module, prior to delivery of the mixture. Master database module 11 receives the alert and stores the information specifying the actual quantity produced.

At step 1330, an alert is transmitted if the second information does not meet a second predetermined criterion. If the quantity of concrete mixture actually produced does not meet specified requirements, master database module 11 transmits an alert to the producer and/or customer. In one embodiment, the alert is transmitted in real time.

In another embodiment, production module 14 may inform master database module 11 if the method of manufacture specified in the mixture formulation is changed. For example, a step of the method may be modified or eliminated, or a new step may be added.

The method now proceeds to step 1335 of FIG. 13B.

The mixture is now placed on a transport vehicle, such as a truck, and transported to the delivery site specified in the order. The vehicle includes transport module 15, which may be a software application operating on a processing device, for example. The vehicle may have one or more sensors to obtain data such as temperature of the mixture, water content of the mixture, etc. During transport, transport module 15 monitors the condition of the mixture and detects changes made to the mixture.

At step 1335, third information identifying a change made to the mixture produced during transport of the mixture is received, from a transport module operating on a third device located on a vehicle transporting the mixture produced from the production facility to a delivery site. In the illustrative embodiment, the driver of the truck makes a change to the mixture during transport to the delivery site. For example, the driver may add additional water to the mixture while the mixture is in the truck. Transport module 15 transmits an alert to master database module 11 and to alert module 17 indicating the change that was made. In one embodiment, the alert is transmitted in real time.

At step 1340, an alert is transmitted if the third information does not meet a third predetermined criterion. If the third information is not within pre-established tolerances, an alert is issued to the producer and/or customer. In one embodiment, the alert is transmitted in real time.

In the illustrative embodiment, the mixture is delivered to the producer's and/or customer's construction site. At the producer's and/or customer's site, site module 16 monitors delivery of the mixture and performance of the mixture after delivery. At step 1345, fourth information relating to delivery of the mixture produced is received, from a site module operating on a fourth device associated with the delivery site. When the mixture is delivered to the specified delivery site, site module 16 transmits an alert to master database module indicating that the mixture has been delivered. In one embodiment, the alert is transmitted in real time.

At step 1350, an alert is transmitted if it is determined that the fourth information does not meet a fourth predetermined criterion. For example, if the delivery of the mixture occurs outside of a specified delivery time frame (e.g., if the delivery is late), master database module 11 (or alert module 17) may transmit an alert to the producer and/or customer. In one embodiment, the alert is transmitted in real time.

The site module 16 may also monitor certain performance parameters of the mixture after it is delivered and used. At step 1355, fifth information relating to a performance of the mixture is received, from the site module. After the mixture is used (e.g., when the concrete mixture is laid), site module 16 may transmit to master database module 11 information including performance data. In one embodiment, the information is transmitted in real time.

At step 1360, an alert is transmitted if it is determined that the fifth information does not meet a fifth predetermined criterion. Thus, if the performance data does not meet specified requirements, master database module 11 (or alert module 17) transmits an alert to the producer and/or customer. In one embodiment, the alert is transmitted in real time.

As described above, alerts are issued at various stages of the production process to inform master database module 11 of events and problems that occur during production, transport, and delivery of the mixture. Master database module 11 (or alert module 17) may then alert the producer and/or customer if a parameter does not meet specified requirements.

Master database module 11 may collect information from various modules involved in the production of a mixture, in real time, and provide the information to the producer and/or customer, in real time. For example, when master database module 11 receives from a respective module information pertaining to the production of a mixture, master database module 11 may transmit an alert to the producer and/or customer in the form of an email, or in another format.

In one embodiment, master database module 11 maintains a web page associated with a producer's and/or customer's order and allows the producer (and/or the customer) to access the web page. Information received from various modules involved in the production of the mixture may be presented on the web page. In addition, information relating to cost analysis may be presented on the web page. For example, an analysis of the impact of a modification to the mixture formulation, a change to the mixture during production or transport, a delay in delivery, or any other event, on the cost of materials (COM) and/or on the producer's profitability may be provided on the web page.

Figure 14:
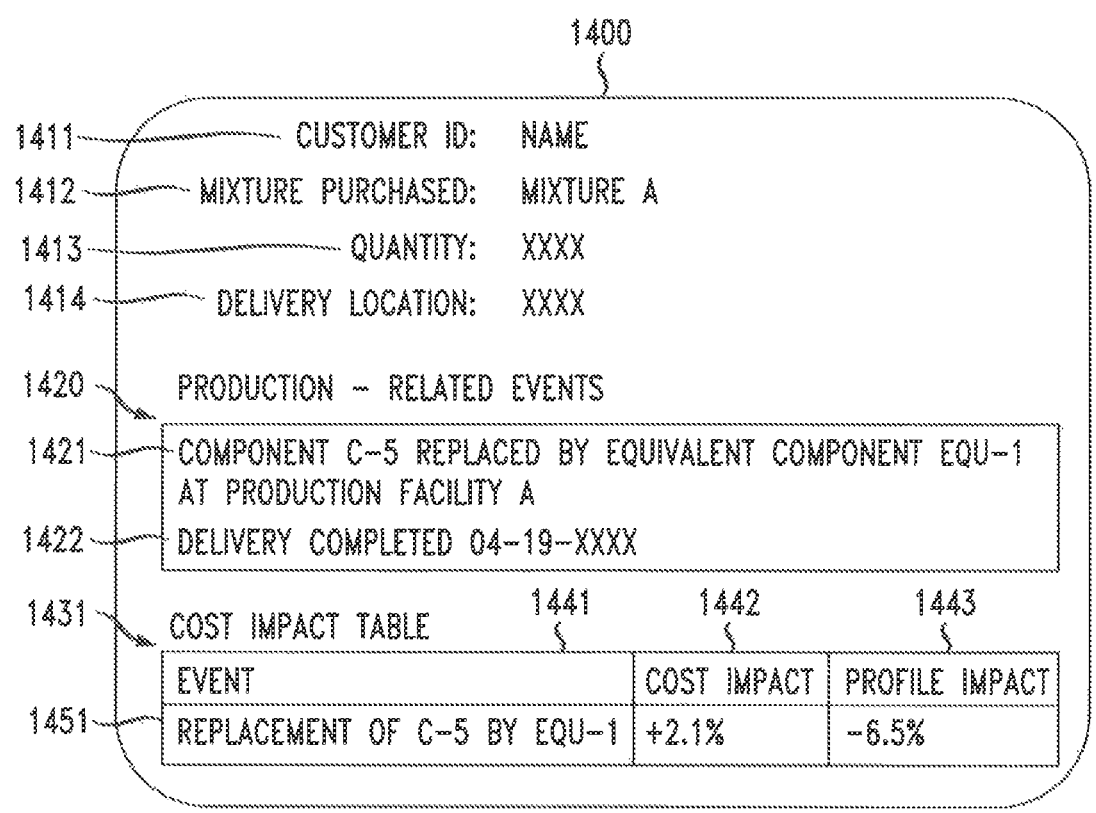
FIG. 14 shows an exemplary web page that displays information relating to purchase, production and delivery of a mixture in accordance with an embodiment.

FIG. 14 shows an exemplary web page that may be maintained in accordance with an embodiment. For example, access to the web page may be provided to a producer to enable the producer to manage the production system and to control costs and profitability. Web page 1400 includes a customer ID field 1411 showing the producer's and/or customer's name or other identifier, a mixture purchased field 1412 showing the mixture that the producer and/or customer purchased, a quantity field 1413 showing the quantity of the mixture ordered, and a delivery location field 1414 showing the delivery location specified by the producer and/or customer.

Web page 1400 also includes a Production-Related Events field 1420 that lists events that occur during production of the mixture. Master database module 11 may display in field 1420 information received from various modules during production of the mixture, including information indicating modifications made to the mixture formulation prior to production, changes made to the mixture during transport of the mixture, information related to delivery, etc. In the illustrative embodiment of FIG. 14, field 1420 includes a first listing 1421 indicating that component C-5 of the mixture formulation was replaced by an equivalent component EQU-1 at Production Facility A (prior to production). Field 1420 also includes a second listing 1422 indicating that delivery of the mixture was completed on 04-19-XXXX.

Web page 1400 also includes a Cost Impact Table 1431 showing the expected impact of certain events on cost and profitability. Table 1431 includes an event column 1441, a cost impact column 1442, and a profitability impact column 1443. Master database module 11 accesses stored information concerning the costs of various components and calculates the expected impact of one or more selected events on the producer's costs. In the illustrative embodiment, row 1451 indicates that the replacement of C-5 by EQU-1 is expected to increase the cost of the mixture by +2.1%, and reduces the producer's profit by 6.5%.

In accordance with another embodiment, statistical measures of various aspects of the production process are generated for a plurality of production facilities and used to establish one or more benchmarks.

Concrete performance is generally specified and used on the basis of its 28 day compressive strength, or at times for pavement construction on the basis of its flexure strength at a specified age such as 7 or 28 days. The methods of measurement and reporting are generally specified by the American Society for Testing and Materials, or ASTM (such as ASTM C39 and C78) and the equivalent International standards such as applicable EN (European Norms). Additionally, concrete mix design and quality evaluation is guided by American Concrete Institute (ACI) 318 as a recommended procedure, which is almost always mandated by project specifications in the US, and also used in many countries worldwide. In ACI 318 a set of statistical criteria are established that relate concrete mix design strength, F'cr, to its structural grade strength, F'c, as used in the design process by the structural engineer. Thus the concrete producer designs his or her mixtures to meet certain F'cr values in order to meet certain desired F'c structural grades specified in the project specifications. A variable relating F'cr and F'c is the standard deviation of strength testing, SDT, as determined per prescribed ACI procedures. The ACI formulae include:

For F'c<5,000 psi:

$$F'cr = F'c + 1.34\, SDT \quad \text{(ACI 1)}$$

(1% probability that the run average of 3 consecutive tests are below F'c)

$$F'cr = F'c - 500 + 2.33\, SDT \quad \text{(ACI 2)}$$

(1% probability that a single test is 500 psi or more below F'c)

For F'c>5,000 psi—[1] applies but [2] is replaced by [3] below:

$$F'cr = F'c - 0.1 F'c + 2.33\, SDT \quad \text{(ACI 3)}$$

(1% probability that a single test is 10% of F'c or more below F'c)

In general the above equations can be expressed in the following form:

Mix Design Strength (F'cr)=Structural Grade Strength (F'c)+An overdesign factor proportional to the Standard Deviation of testing, SDT.

The factor SDT is a direct measure of concrete quality and reliability, and experience shows that it can range widely from an excellent level of on the order of 80 to 200 psi, to the very poor level of over 1,000 psi. Concrete mix design cost factor is directly proportional to SDT, which means that high quality concrete is also less expensive to produce since it would contain less cement (or cementitious materials, which include binders such as slag, fly ash, or silica fume in addition to cement).

Because of the above ACI approach now in practice for many decades, the industry (including ready mix producers, test labs, contractor, and specifying engineers) has paid significant attention to test results variability and the standard deviation of testing.

Figure 15:
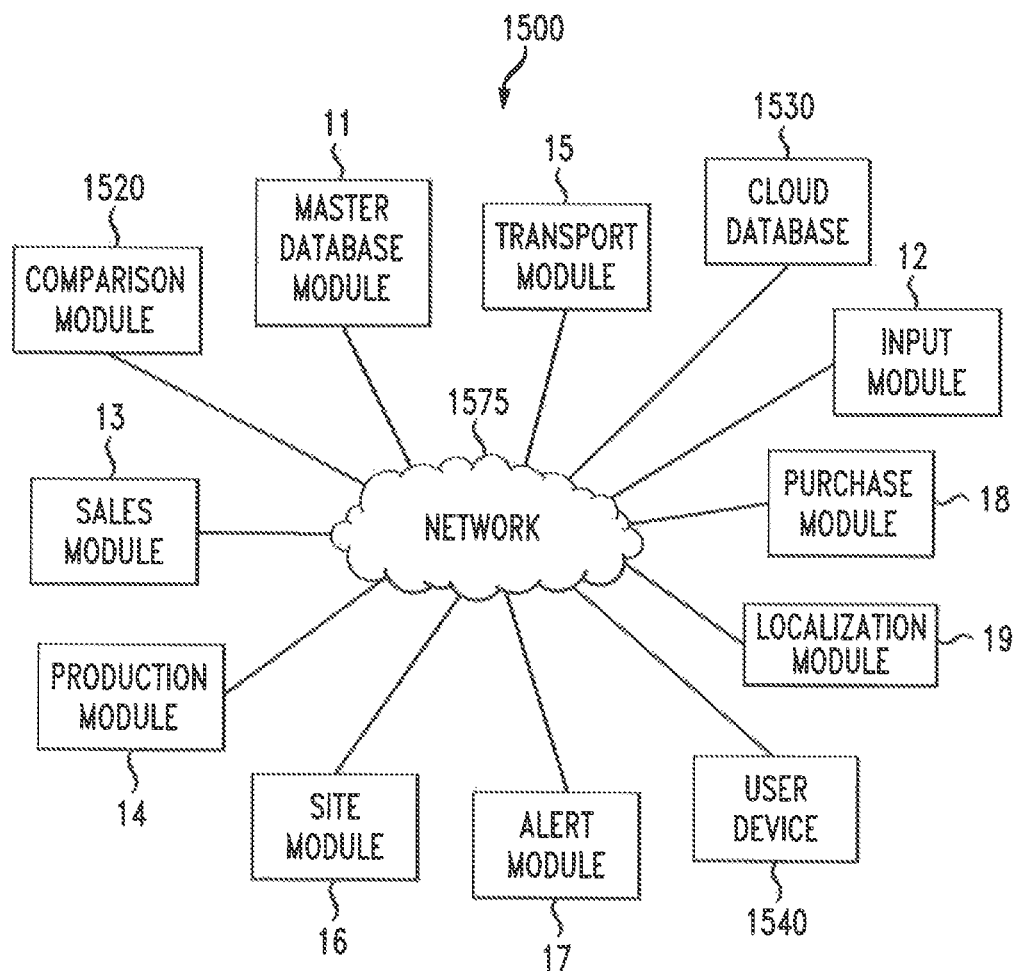
FIG. 15 shows a production management system in accordance with another embodiment.

FIG. 15 shows a production management system 1500 in accordance with an embodiment. Product management system 1500 includes a master database module 11, input module 12, sales module 13, production module 14, transport module 15, site module 16, alert module 17, purchase module 18, and localization module 19. Production management system 1500 also includes a comparison module 1520, a network 1575 and a cloud database 1530. Various components, such as master database module 11, may from time to time store data in cloud database 1530. Production management system 1500 also comprises a user device 1540.

In another embodiment, the master database module 11, the comparison module 1520, and the alert module 17 are housed within a single module.

In one embodiment, a batch of a concrete mixture is produced at a production facility in accordance with a formulation. Certain aspects of the batch produced are measured and differences between the batch produced and the formulation requirements are identified. The differences are analyzed to determine if the differences fall within acceptable tolerances.

Figure 16B:
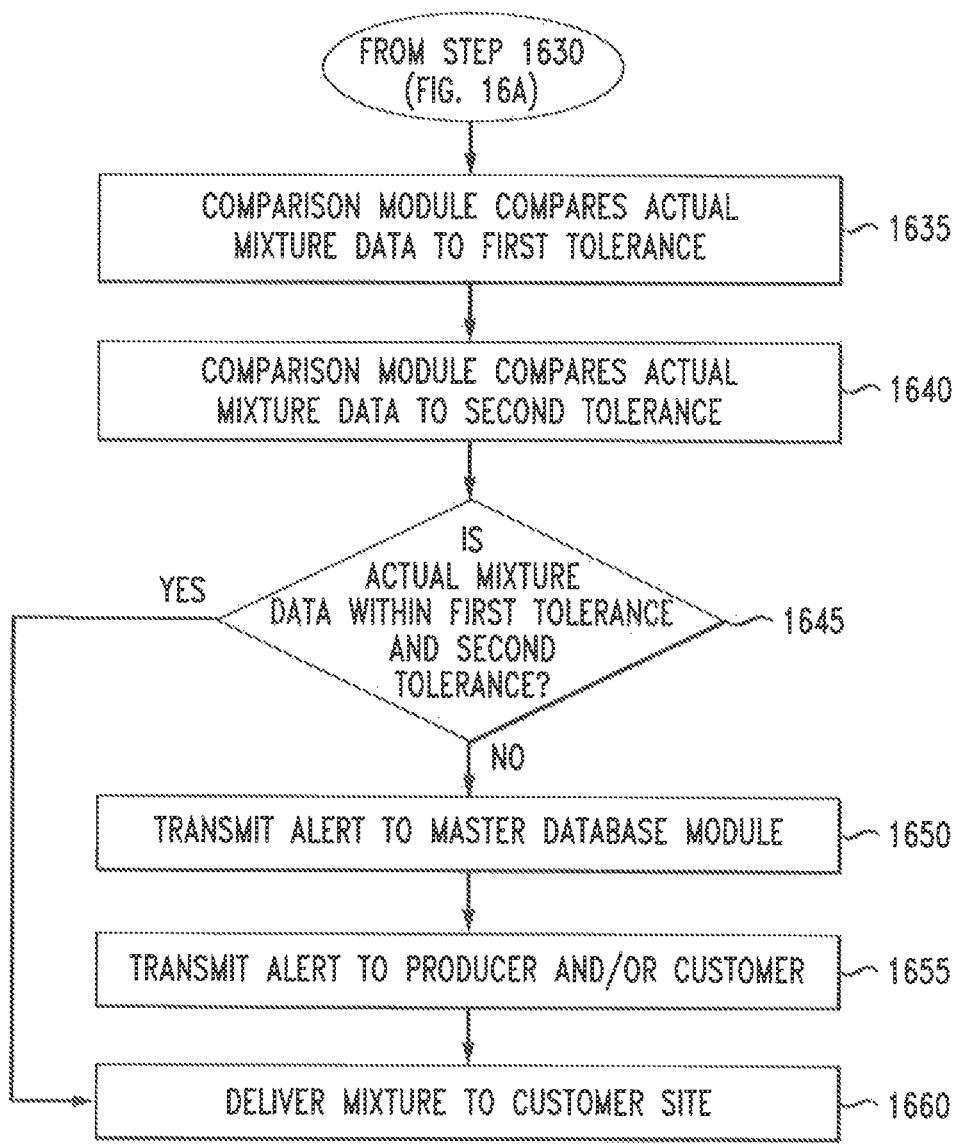

FIGS. 16A-16B comprise a flowchart of a method of producing and analyzing a mixture in accordance with an embodiment. At step 1605, a mixture formulation is input into a master database module. In the illustrative embodiment, input module 12 provides a formulation for a particular concrete mixture to master database module 11. Master database module 11 stores the formulation.

In one embodiment, a plurality of mixture formulations is provided by input module 12 to master database module 11. A master list of mixtures, comprising a plurality of mixture formulations, is maintained at master database module 11.

As described above, master database module 11 may generate localized versions of a mixture formulation. Referring again to FIG. 8, localization module 19 generates localized mixture formulations for Production Facility A, Production Facility B, etc.

At step 1610, data relating component types and costs are input into the master database module. Technical data for a variety of components used in the formulation (and in other formulations), as well as cost data for the components, is provided by input module 12 to master database module 11. Technical data and cost data for various components may be stored in a components database 803, shown in FIG. 8.

At step 1615, first tolerance data and second tolerance data are input into the master database module. Input module 12 transmits to master database module 11 information defining a first tolerance and information defining the second tolerance. For example, tolerances may indicate that an amount of water in a batch of a concrete mixture must fall within a specified range, or that an amount of cementitious in the concrete mixture must fall within a specified range. Tolerance information is stored in tolerances database 804.

At step 1620, a formulation is provided to the production module. Master database module 11 transmits the mixture formulation to a selected production facility. For example, master database module 11 may provide a respective localized mixture formulation to Production Facility A (841). A different localized mixture formulation may be provided to Production Facility B (842), for example.

At step 1625, the mixture is produced at the production facility. The production facility produces one or more batches of the mixture. For example, Production Facility A (841) may produce a batch of the mixture based on the mixture formulation.

At step 1630, actual mixture data is provided to master database module. After a batch is made, production module 14 provides batch data indicating the actual quantity of the mixture produced, the components used to make the batch, the quantity of each component, etc., to master database module 11. Production module 14 obtains batch data indicating the actual quantity of the mixture produced, which components were actually used, etc., and transmits the batch data to master database module 11. Master database module 11 may store the batch data. The method now proceeds to step 1635 of FIG. 16B.

At step 1635, the comparison module compares the actual mixture data to the first tolerance. Comparison module 1520 accesses the stored batch data, and accesses tolerance information in tolerances database 804 (shown in FIG. 8). Comparison module 1520 applies the first tolerance to the batch data to determine whether the batch data is acceptable.

At step 1640, the comparison module compares the actual mixture data to the second tolerance. Comparison module 1520 accesses the stored batch data and applies the second tolerance to the batch data to determine whether the batch data is acceptable.

Referring to block 1645, a determination is made whether the actual mixture data are within the first tolerance and the second tolerance. Comparison module 1520 determines whether the actual mixture data are within the specified tolerances. If the actual mixture data are within the first tolerance and the second tolerance, the method proceeds to step 1660. If the actual mixture data are not within the first tolerance and the second tolerance, the method proceeds to step 1650.

At step 1650, an alert is transmitted to the master database module. Comparison module 1520 transmits to master database module 11 an alert indicating that the batch data are not within acceptable tolerances.

At step 1655, an alert is transmitted to the producer and/or to the customer. Alert module 17 transmits to the producer and/or customer an alert indicating that the batch data are not within acceptable tolerances.

In another embodiment, a first alert is issued if the batch data is not within the first tolerance, and a second alert is issued if the batch data is not within the second tolerance.

At step 1660, the mixture is delivered to the producer and/or customer site. The mixture is placed on a transport vehicle and is delivered to the site specified by the producer and/or customer in the order.

In accordance with another embodiment, comparison module 1520 monitors the quantity of one or more components in each batch actually produced, and compares the amounts to the amounts of such components as specified in the formulation.

Figure 17:
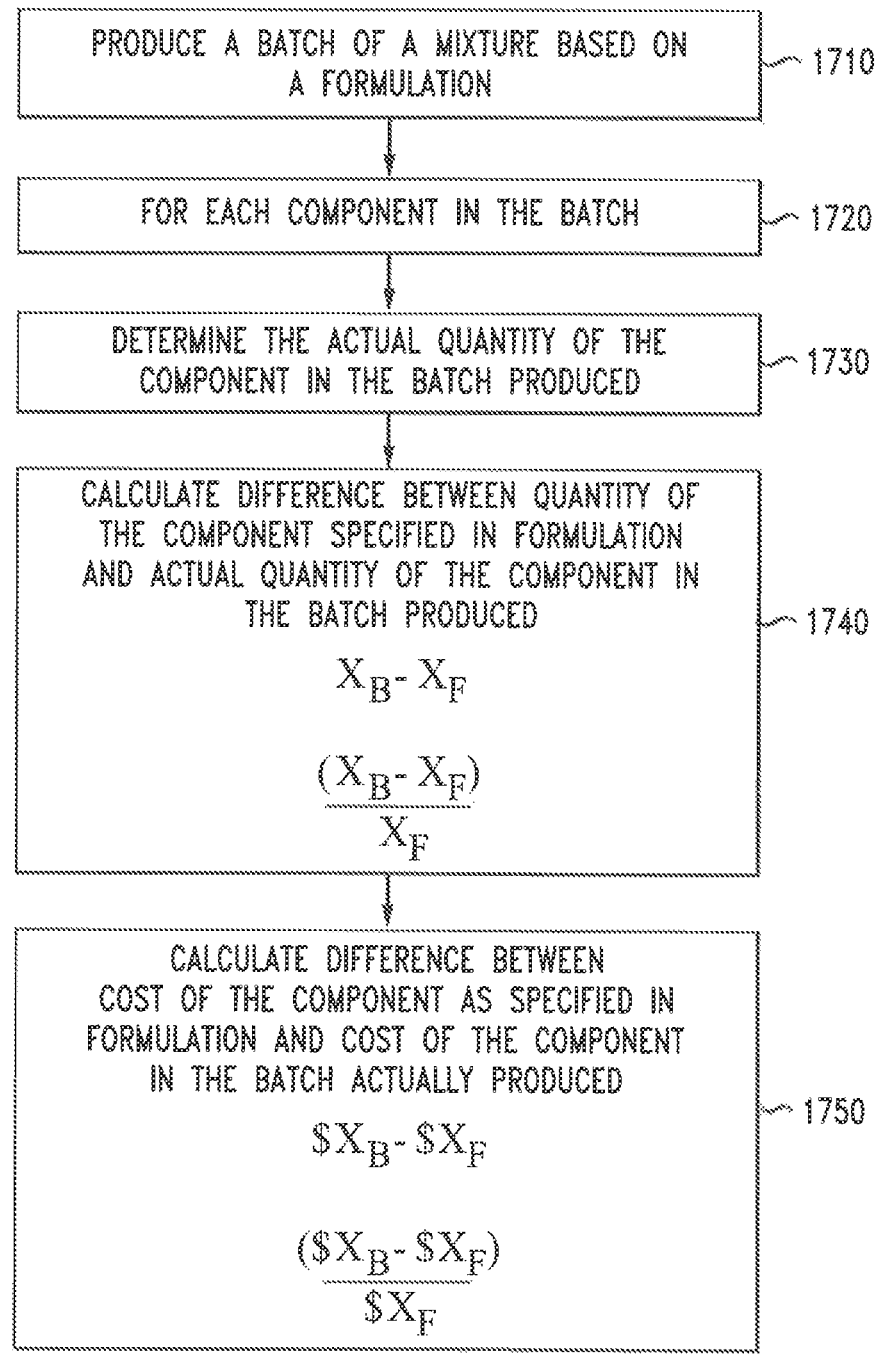
FIG. 17 is a flowchart of a method of producing a formulation-based mixture in accordance with an embodiment.

FIG. 17 is a flowchart of a method of producing a formulation-based mixture in accordance with an embodiment. In another illustrative embodiment, suppose that another producer and/or customer orders a desired quantity of the mixture defined by Mixture Formulation (810). Several production facilities may be selected to produce the mixture, including Production Facility C (841). Master database module 11 transmits localized Mixture Formulation C (810-C) to production facility C (843).

At step 1710, a batch of a mixture is produced based on a formulation. A batch of the mixture is produced at Production Facility C (843) based on localized Mixture Formulation A (810-C). Referring to FIG. 10, localized Mixture Formulation (810-C) specifies the following components and quantities: C-1, Q-1; C-2, Q-2; C-3, Q-3; C-4, Q-4; C-5, (0.7)*(Q-5); and C-6, Q-6.

Referring to block 1720, for each component X in the batch, a series of step is performed. Thus, the steps described below are performed with respect to each of the components C-1, C-2, C-3, C-4, C-5, and C-6. For convenience, the method steps are described with respect to component C-1; however, the steps are also performed for each of the other components.

At step 1730, the actual quantity of the component in the batched mixture, $X_B$, is determined. Thus, the actual quantity of C-1 used in the batch produced at Production Facility C (843) is determined. Production module 14 obtains this information concerning the actual quantity of the component in the batched mixture, $X_B$, and transmits the information to master database module 11.

Now a measure of a difference between the batch and the formulation is determined based on a relationship between the quantity of the component in the batched mixture, $X_B$, and the quantity of the component as specified by the formulation, $X_F$.

Specifically, at step 1740, a difference between the quantity of the component specified in the formulation and the actual quantity of the component in the batch produced is calculated. Specifically, the difference $(X_B - X_F)$ is calculated, where $X_B$ is the amount of the component actually used in the batch produced and $X_F$ is the amount of the component as specified in the formulation. In some embodiments, a percentage value representing the difference may also be computed using the following formula:

$$\Delta X = (X_B - X_F)/X_F.$$

In the illustrative embodiment, comparison module 1520 calculates the quantity $\Delta X$, and provides the information to master database module 11. The quantity $\Delta X$ is stored at master database module 11.

At step 1750, a difference between the cost of the component as specified in the formulation and the cost of the component in the batch produced is calculated. Thus, the difference ($\$X_B - \$X_F$) is calculated, where $\$X_B$ is the cost of the component actually used in the batch produced and $\$X_F$ is the cost of the component as specified in the formulation. In some embodiments, a percentage value representing the difference may also be calculated using the following formula:

$$\Delta \$X = (\$X_B - \$X_F)/\$X_F,$$

In the illustrative embodiment, comparison module 1520 calculates the quantity $\Delta \$X$ and provides the information to master database module 11. The quantity $\Delta \$X$ is stored at master database module 11.

In accordance with an embodiment, comparison module 1520 particularly monitors the quantity of cementitious and the quantity water in each batch. Systems and methods for monitoring and analyzing quantities of cementitious and water in batches produced are described below.

For convenience, the terms $CM_F$, $CM_B$, $W_F$, and $W_B$ are defined as follows:

$CM_F$=the amount of cementitious specified in the formulation, $CM_B$=the actual amount of cementitious in a batch produced, $W_F$=the amount of water specified in the formulation, $W_B$=the actual amount of water in a batch produced.

Then $\Delta CM$ and $\Delta W$ are defined as follows:

$$\Delta CM = CM_B - CM_F$$

$$\Delta W = W_B - W_F$$

Using the terms defined above, set forth below is a method of computing a standard deviation of $\Delta CM/CM_F$ (referred to as SDrCM) and a standard deviation of $\Delta W/W_F$ (referred to as SDrW, for each production facility, across all its production batches and mixes.

In accordance with well-known principles of concrete technology, and since strength is proportional to CM/W ratio, it can be shown that for any given mix, a variance of the strength S of a given batch of concrete has the following relationship to CM and W:

$$\Delta S/S = (\Delta CM/CM) - (\Delta W/W)$$

Accordingly, relative strength increases as CM specified in the formulation increases. Likewise, relative strength increases as W specified in the formulation decreases.

In accordance with well-known statistical principles, the variance (VAR) of the strength measure can be expressed as follows:

$$VAR(\Delta S/S) = VAR(\Delta CM/CM) + VAR(\Delta W/W) = (SDrCM)^2 + (SDrW)^2$$

Now if SDrWCM is the standard deviation of the measured ratio W/CM in a batch actually produced relative to the value of W/CM specified in the formulation, the SDrWCM can be expressed as follows:

$$(SDrWCM) = [(SDrCM)^2 + (SDrW)^2]^{1/2}$$

Hence:

$$SDrS = (SDrWCM),$$

where SDrS is the standard deviation of relative strength resulting from the variability of the batching process. The term "relative strength" as used herein means the difference in strength in all batches actually produced at a given production facility relative to the strength baseline specified in the formulation, due to the batching variabilities of CM and W, expressed as a ratio with respect to the strength baseline specified in the formulation.

It follows that:

$$SD(\Delta S) = S \times (SDrWCM)$$

In accordance with an embodiment, the closed loop production management system described herein provides, in real time, to a producer and/or a customer, the statistical values SDrCM and SDrW, and SD($\Delta S$). SD($\Delta S$) is a direct measure of concrete strength performance quality related to the quality of the production batching process, both of which are characterized by the applicable SD values. Low batching quality is reflected by a high SD value; high batching quality is reflected by a low SD. Thus as the batching quality deteriorates, the strength quality also decreases proportionally.

Accordingly, when the batching quality decreases, it may be necessary to adjust the applicable formulation by using an extra batching driven increment in the SDT standard deviation factor. This is done using the ACI 318 Eqs. [1]-[3] and the equation above in the following form:

$$\Delta F'cr = 1.34 \times S \times (SDrWCM) \qquad [1a]$$

$$\Delta F'cr = 2.33 \times S \times (SDrWCM) \qquad [2a]$$

$$\Delta F'cr = 2.33 \times S \times (SDrWCM) \qquad [3a]$$

where $\Delta F'cr$ is an added mix design strength increment resulting from the batching variability SDrWCM, for each of the three ACI equations. Since Equations [2a] and [3a] are identical, the three ACI statistical criteria are in fact reduced to two for these batching increment cases.

Because F'cr is the theoretical strength associated with the specified formulation, an increase in F'cr is associated with an increase in the CM content at constant W, resulting in an increase in the cost of the CM cost in the mixture. The cost of CM in a mixture can be expressed as follows:

$\Phi$=CM efficiency factor in PSI/(LB·CYD)

$K$=CM cost per LB $\$CM$=CM cost per $cyd = (K/\Phi) \times F'cr$

Figure 18:
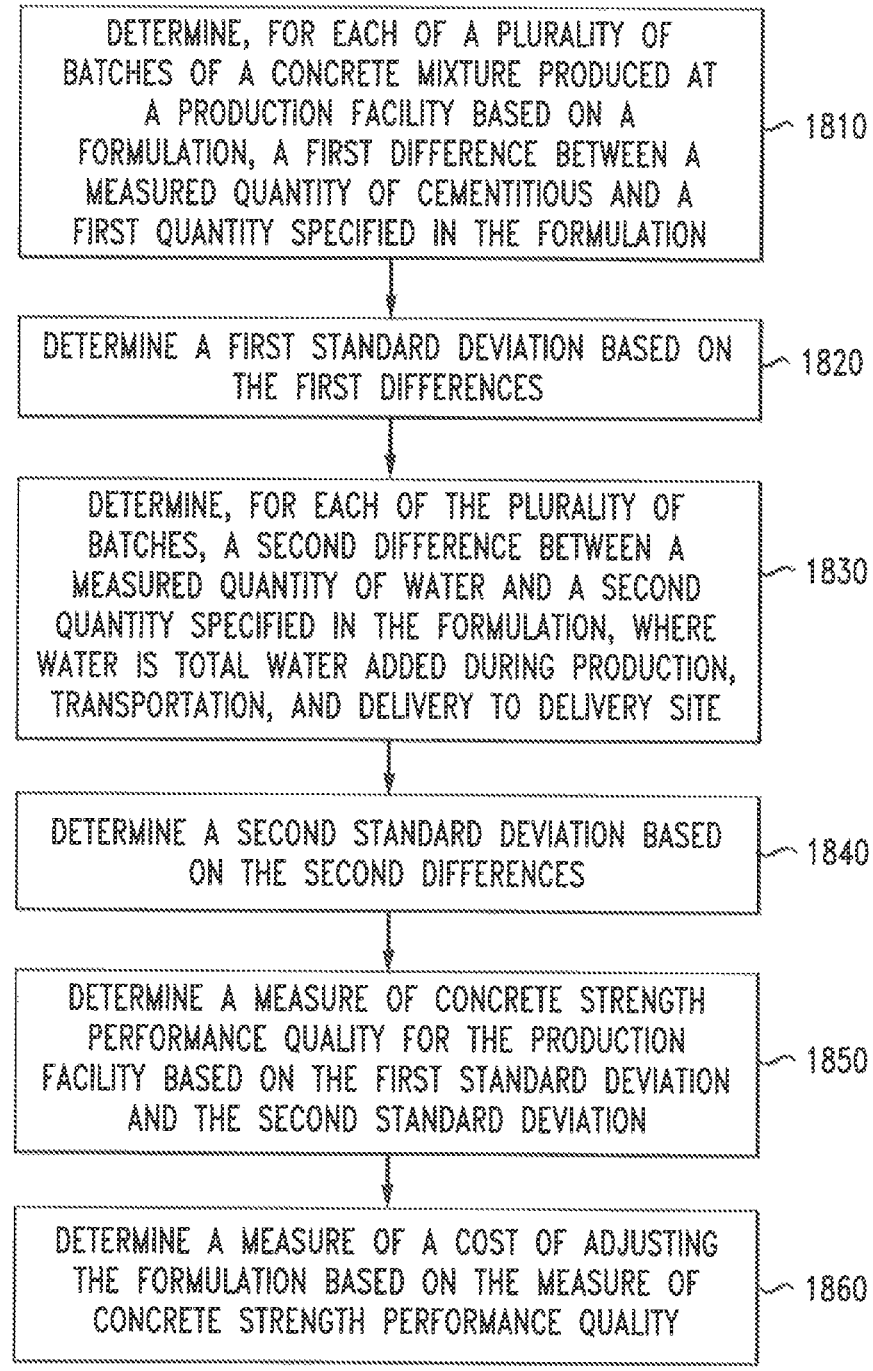
FIG. 18 is a flowchart of a method of determining a measure of concrete strength performance quality for concrete produced at a production facility in accordance with an embodiment.

It follows from the equation above and Equations [1a-1b] that:

$\Delta \$CMB$=increase in CM cost due to batching SD $\Delta \$CMB = 1.34 \times (K/\Phi) \times S \times SDrWCM$ $\Delta CSTB = 2.33 \times (K/\Phi) \times S \times SDrWCM$ Accordingly, in accordance with an embodiment, standard deviations are determined in according with the principles described above, and are used to determine a measure of concrete strength performance quality for a plurality of batches produced at a production facility. FIG. 18 is a flowchart of a method of determining a measure of concrete strength performance quality for concrete produced at a production facility in accordance with an embodiment.

At step 1810, a first difference between a measured quantity of cementitious and a first quantity specified in a formulation is determined, for each of a plurality of batches of concrete produced at a production facility. As described above, for each batch, the batched CM is measured, and information indicating the batched CM is provided to master database module 11. Comparison module 1520 then determines the difference ΔCM between the batched CM and the CM amount specified in the formulation.

At step 1820, a first standard deviation is determined based on the first differences. In the illustrative embodiment, comparison module 1520 calculates the Standard Deviation SDrCM of the difference of batched CM versus design specification (formulation) CM over all batches produced in the production facility.

At step 1830, a second difference between a measured quantity of water and a second quantity specified in the formulation is determined for each of the plurality of batches, where water is the total water added during production, transportation, and delivery to the delivery site. As described above, for each batch, the batched W is measured, and information indicating the batched W is provided to master database module 11. Comparison module 1520 determines the difference ΔW between the batched W and the W amount in the formulation.

At step 1840, a second standard deviation is determined based on the second differences. Comparison module 1520 calculates the Standard Deviation SDrW of the difference of batched W versus the design specification (formulation) W over all batches produced in the production facility.

At step 1850, a measure of concrete strength performance quality is determined for the production facility based on the first standard deviation and the second standard deviation. In the manner described above, comparison module 1520 determines SD(ΔS) based on SDrCM and SDrW.

At step 1860, a measure of a cost of adjusting the formulation is determined based on the measure of concrete strength performance quality. Comparison module 1520 calculates the potential impact on costs of adjusting the design specification (formulation). For example, as described above, increasing F'cr may result in an increase in costs due to an increase in the cost of CM in the mixture. The increase in CM cost Δ$CMB may be calculated using equations discussed above.

In accordance with another embodiment, statistical data is provided to a producer and/or a customer, for example, via a web page displayed on a user device. Suppose, for example, that a producer who owns and/or manages a plurality of production facilities wishes to compare the performance of the various production facilities. Statistical performance measures of the respective performance facilities are provided. For example, in the illustrative embodiment of FIG. 15, the producer may employ user device 1540 to access a web page and view the statistical data.

Figure 19A:
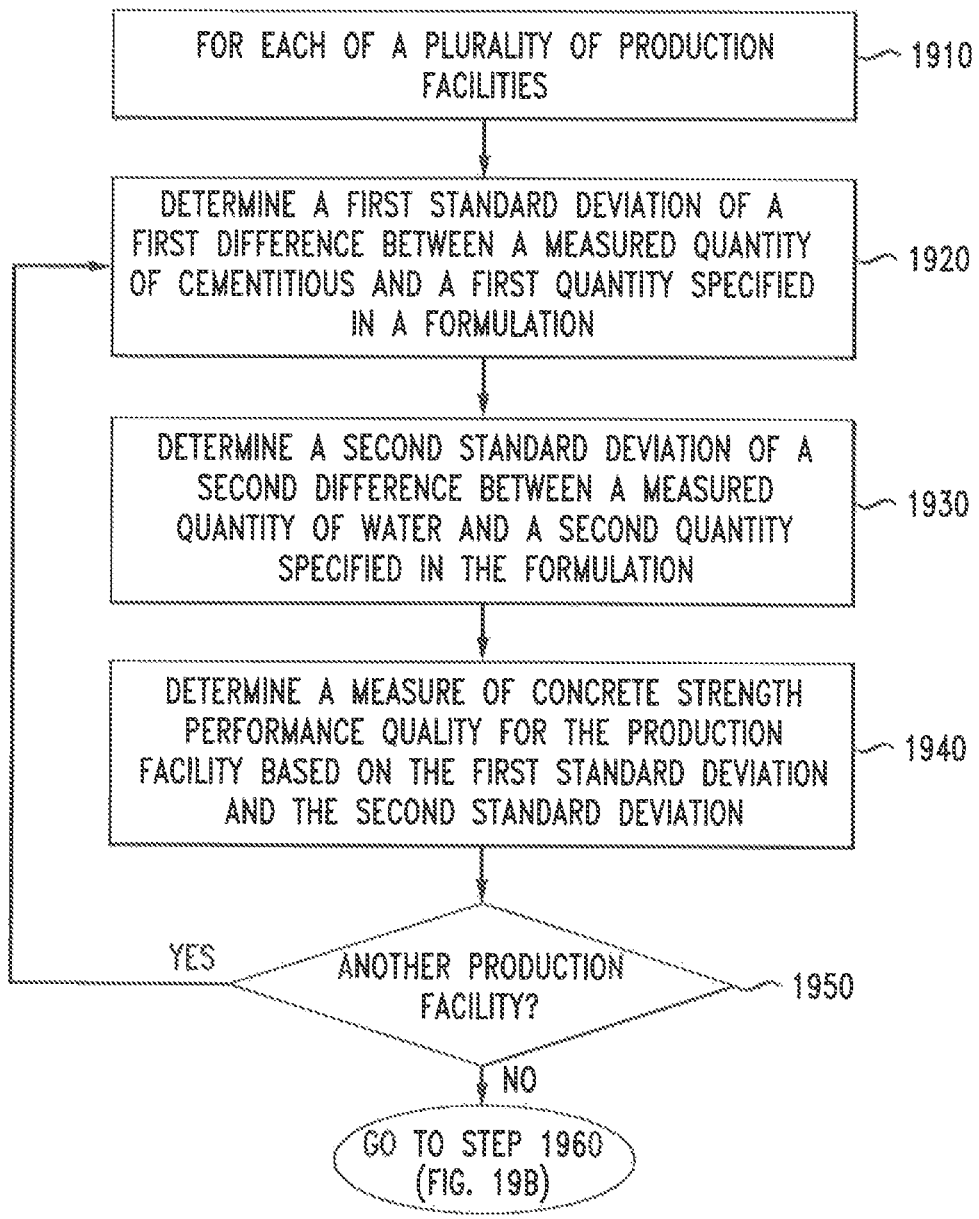
FIGS. 19A-19B comprise a flowchart of a method of providing comparative statistical information relating to a plurality of production facilities in accordance with an embodiment.
Figure 19B:
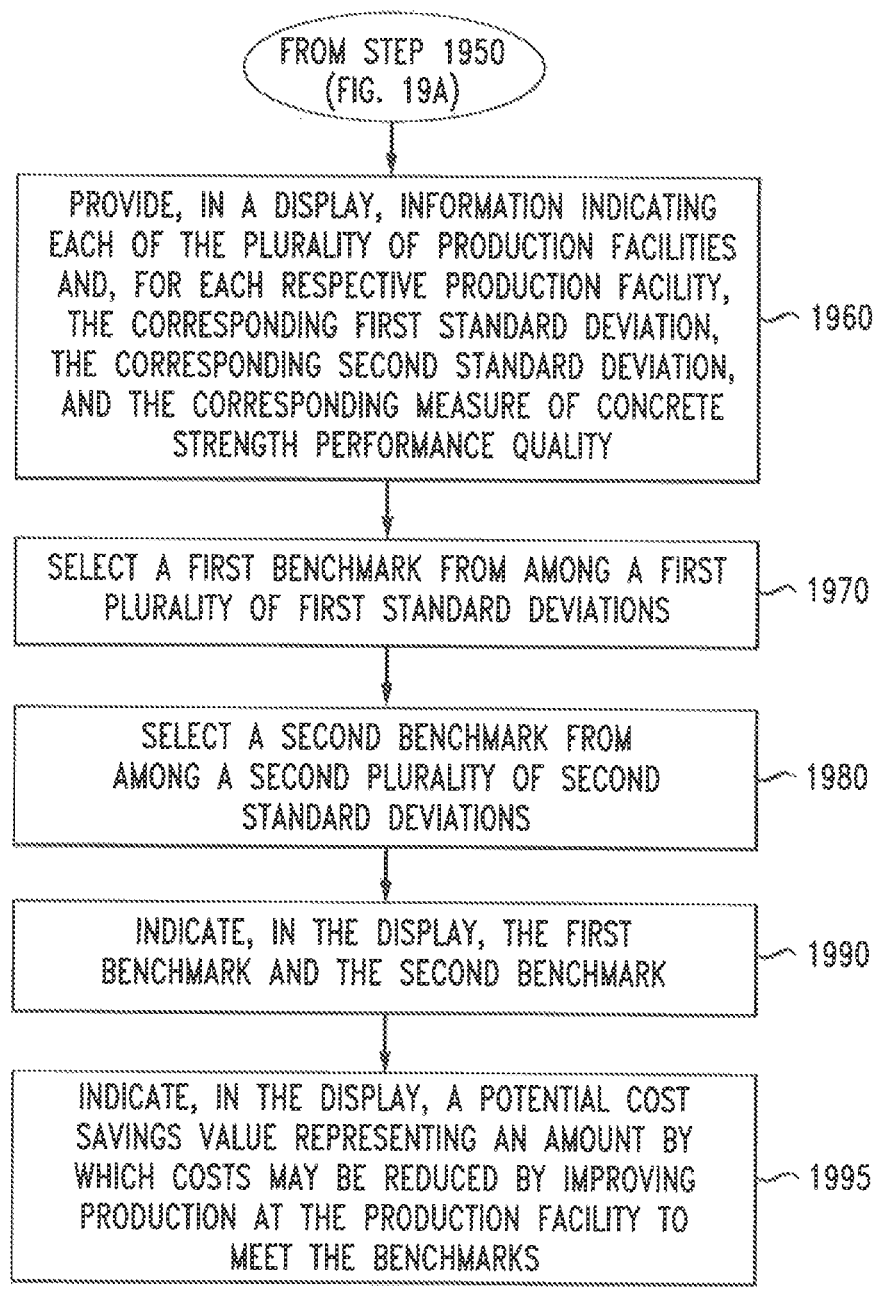

FIGS. 19A-19B comprise a flowchart of a method of providing comparative statistical information relating to a plurality of production facilities in accordance with an embodiment. Referring to block 1910, for each of a plurality of production facilities, a series of actions is performed as described below.

For a selected production facility (such as Production Facility A(841)), the following steps are performed. At step 1920, a first standard deviation of a first difference between a measured quantity of cementitious and a first quantity specified in a design specification is determined. Comparison module 1520 computes the first standard deviation SDrCM of the difference of batched CM versus design specification (formulation) CM over all batches produced in the production facility, as described above in steps 1810-1820.

At step 1930, a second standard deviation of a second difference between a measured quantity of water and a second quantity specified in the design specification is determined. Comparison module 1520 computes the second standard deviation SDrW of the difference of batched W versus the design specification (formulation) W over all batches produced in the production facility, as described above in steps 1830-1840.

At step 1940, a measure of concrete strength performance quality for the production facility is determined based on the first standard deviation and the second standard deviation. Comparison module 1520 computes SD(ΔS) based on SDrCM and SDrW, as described above in step 1850.

Referring to block 1950, the method may return to step 1920 and statistics for another production facility may be generated in a similar manner. Preferably, statistical information is generated for a plurality of production facilities. Otherwise, the method proceeds to step 1960 of FIG. 19B.

At step 1960, information indicating each of the plurality of production facilities and, for each respective production facility, the corresponding first standard deviation, the corresponding second standard deviation, and the corresponding measure of concrete strength performance quality, is provided in a display. In one embodiment, the statistical information computed by comparison module 1520 may be displayed on a web page such as that shown in FIG. 20. Web page 2001 includes a statistics table 2010 which includes six columns 2011, 2012, 2013, 2014, 2015, and 2016. Production facility identifier column 2011 includes identifiers for a plurality of production facilities. Columns 2012, 2013, 2014, and 2015 store values for SDrCM, SDrW, SDrWCM, and SD(ΔS), respectively, for each respective production facility listed. For example, referring to record 2021, the production facility identified as PF-1 has the following statistics: sdrcm-1; sdrw-1; sdrwcm-1; sd-1. Column 2016 displays a potential cost savings for each production facility listed.

At step 1970, a first benchmark is selected from among a first plurality of first standard deviations. For example, in the illustrative embodiment, comparison module 1520 may determine that the standard deviation associated with the best performance among those displayed in SDrCM column 2012 is sdrcm-2 (shown in record 2022).

At step 1980, a second benchmark is selected from among a second plurality of second standard deviations. For example, comparison module 1520 may determine that the standard deviation associated with the best performance among those displayed in SDrW column 2013 is sdrw-4 (shown in record 2024).

At step 1990, the first benchmark and the second benchmark are indicated in the display. In the illustrative embodiment, the benchmark standard deviations are displayed, respectively, in a Benchmark (SDrCM) field 2031 and a Benchmark (SDrW) field 2032. The two benchmark values are also highlighted in columns 2012, 2013. In other embodiments, the benchmark values may be indicated in a different manner. In another embodiment, a benchmark standard deviation of strength (PSI) is determined based on the benchmark values from fields 2031, 2032, and/or the values in column 2014. A benchmark consistency value may be determined as well. The benchmark standard deviation of strength value and benchmark consistency value may be displayed on web page 2001.

At step 1995, a potential cost savings value representing an amount that may be saved by improving production at the production facility to the benchmark is displayed in the display. For example, comparison module 1520 determines, for each production facility listed, how much savings may be achieved by improving the production process at the facility to meet the first and second benchmarks. In the illustrative embodiment of FIG. 20, the cost savings information is displayed in column 2016.

In another embodiment, a single generalized benchmark is determined based on the first benchmark and the second benchmark. A potential cost savings value is determined based on the generalized benchmark.

These and other aspects of the present Invention may be more fully understood by the following Examples.

Example

Illustration of the Impact of Concrete SD on its CM Cost

As shown in Table 1, concrete variability impacts its CM (cementitious cost) cost very significantly. The analysis is performed for a concrete of structural grade 4,000 psi, and using the referenced equations previously derived in this document. The example analysis assumes a CM efficiency factor, $\Phi=8$ psi/(LB·cyd), and a CM cost, K=$0.045/Lb. Starting at a SD of 200 psi, the SD is increased in 100 psi increments in column 2, the mix design strength computed in columns 3 & 4 per two different ACI formulae, with the higher value always governing. The mix CM cost is computed in column 5. The cost of quality variability is well illustrated in columns 6 & 7; column 6 shows that per each 100 psi increase in standard deviation of strength, the CM cost will increase between $0.75 to $1.31 per cyd. Column 7 shows that the CM cost relative to very high quality concrete (represented by row 1) can increase dramatically by more than $8/cyd. Noting that the concrete industry on average generates a net profit of on the order of $0.5 to $2 per cyd, this example (using realistic numbers) illustrates the tremendous importance of maintaining low variability.

An important factor for maintaining low strength performance variability is the consistency of the batching process.

TABLE 1

| | | | | | | | |
|---|---|---|---|---|---|---|---|
| | | | Ref# | | | | |
| | 1 Eng Design Strength | 2 SD, | 3 Mix Design Strength: F'cr, psi | 4 | 5 $CM/CYD | 6 $CM per | 7 Relative cost of Variance |
| Ref# | F'c, psi | psi | Eq [1] | Eq [2] | Eq [9] | 100 psi SD | DEL_$CM/cyd |
| 1 | 4,000 | 200 | 4,268 | 3,966 | $24.01 | $0.00 | $0.00 |
| 2 | 4,000 | 300 | 4,402 | 4,199 | $24.76 | $0.75 | $0.75 |
| 3 | 4,000 | 400 | 4,536 | 4,432 | $25.52 | $0.75 | $1.51 |
| 4 | 4,000 | 500 | 4,670 | 4,665 | $26.27 | $0.75 | $2.26 |
| 5 | 4,000 | 600 | 4,804 | 4,898 | $27.55 | $1.28 | $3.54 |
| 6 | 4,000 | 700 | 4,938 | 5,131 | $28.86 | $1.31 | $4.85 |
| 7 | 4,000 | 800 | 5,072 | 5,364 | $30.17 | $1.31 | $6.17 |
| 8 | 4,000 | 900 | 5,206 | 5,597 | $31.48 | $1.31 | $7.48 |
| 9 | 4,000 | 1,000 | 5,340 | 5,830 | $32.79 | $1.31 | $8.79 |

Set forth below is a discussion of real-time batch data variability with respect to mixture design factors (as specified in a formulation, for example). Hypothetical data are used to illustrate a quantification of the cost of strength performance variably as driven by batching variability.

Example

Quantification of Batching Data Variability

Table 2 sets forth a set of real time data in columns 1-5. Column 6 shows the computed standard deviation W/CM using the raw data from columns 3 and 5.

In the example of Table 2, production facility (plant) #141, represented by row 9, is designated as the benchmark production facility (plant) because it shows the least vaiability.

TABLE 2

Example Quantification of Strength Standard Deviation due to Batching Variability, and the Resulting Cost

| | | | | | | | | |
|---|---|---|---|---|---|---|---|---|
| | | | | Ref# | | | | |
| | | 1 | 2 | 3 | 4 | 5 | | 6 |
| | | | Measured from CLI batch analysis | | | | | Eq [6] - data |
| | | Period | Del_CM % FROM MIX | | Del_WATER % FROM MIX | | | [A] & [B] STDEV |
| | Table [1] | Volume, | AVG | [A] | AVG | [B] | | W/CM [C] |
| Ref # | PLANT | cyds | DELTA | SDrCM | DELTA | SDrW | | SDrWCM |
| 1 | 121 | 5,500 | 0.10% | 0.50% | −22.00% | 3.60% | | 3.6% |
| 2 | 122 | 3,000 | 0.11% | 0.68% | −3.60% | 5.40% | | 5.4% |
| 3 | 124 | 6,800 | −22.30% | 8.20% | −14.00% | 8.00% | | 11.5% |

TABLE 2-continued

Example Quantification of Strength Standard Deviation
due to Batching Variability, and the Resulting Cost

| Table [1] | | | Ref# | | | | |
|---|---|---|---|---|---|---|---|
| | | 1 | 2 | 3 | 4 | 5 | 6 |
| | | | Measured from CLI batch analysis | | | | Eq [6] - data |
| | | Period | Del_CM % FROM MIX | | Del_WATER % FROM MIX | | [A] & [B] STDEV |
| | | Volume, | AVG | [A] | AVG | [B] | W/CM [C] |
| Ref # | PLANT | cyds | DELTA | SDrCM | DELTA | SDrW | SDrWCM |
| 4 | 128 | 2,000 | 0.85% | 1.58% | −10.00% | 4.50% | 4.8% |
| 5 | 131 | 8,990 | −0.49% | 0.33% | −13.70% | 6.00% | 6.0% |
| 6 | 135 | 6,000 | −0.33% | 0.59% | −7.40% | 2.10% | 2.2% |
| 7 | 138 | 2,500 | −0.08% | 0.56% | −11.00% | 5.30% | 5.3% |
| 8 | 140 | 9,850 | −0.33% | 0.40% | −8.70% | 11.60% | 11.6% |
| 9 | 141 | 6,780 | −0.16% | 0.70% | −12.40% | 2.00% | 2.1% |
| 10 | 142 | 4,560 | −0.09% | 0.23% | −9.60% | 3.60% | 3.6% |
| 11 | 143 | 7,860 | 0.34% | 0.71% | −20.20% | 6.00% | 6.0% |
| 12 | 146 | 3,450 | 1.26% | 4.08% | −13.80% | 6.60% | 7.8% |
| 13 | 147 | 5,450 | 2.20% | 1.82% | −14.60% | 2.10% | 2.8% |
| 14 | 150 | 9,540 | 0.41% | 1.71% | −11.00% | 9.20% | 9.4% |

Assuming an average concrete mix design strength of 4,000 psi, Table 3 shows the strength SD (Column 3) computed from the SD of W/Cm; the strength SD varies by more than a factor of 5 from 85 psi for the benchmark plant to 458 psi in plant #124 (row 3). If this batching strength SD were reduced to the benchmark value, then significant CM costs would be saved as shown in column 4; this cost factor varies from $0.02 per cyd to $2.85 due to the varying batching qualities of the production facilities.

Supposing that the mix designs (formulations) developed for the benchmark plant (production facility) are used across all the production facilities, this could lead to a very costly situation, since probability analysis shows that for each 100 psi increase in strength SD from its assumed mix design value, the failure rate will increase by more than 4%, which translates to a potential remedial cost of around $2/cyd per 100 psi of SD increase.

TABLE 3

Closed Loop W/CM Ratio & Batching Strength
Standard Deviations From Real Time Data

| Table [2] | | | Ref# | | |
|---|---|---|---|---|---|
| | | 1 | 2 | 3 | 4 |
| | | | | | Computed from batch |
| | | | Computed per | | data for avg strength of 4,000 psi |
| | | Period | Table [1] STDEV W/CM [C] | Batching Strength SD [D] | Bench Mark Savings |
| Ref # | PLANT | Volume, cyds | SDrWCM | SD(Del_S) | [E] |
| 1 | 121 | 5,500 | 3.6% | 145 | $0.45 |
| 2 | 122 | 3,000 | 5.4% | 218 | $1.00 |
| 3 | 124 | 6,800 | 11.5% | 458 | $2.80 |
| 4 | 128 | 2,000 | 4.8% | 191 | $0.80 |
| 5 | 131 | 8,990 | 6.0% | 240 | $1.17 |
| 6 | 135 | 6,000 | 2.2% | 87 | $0.02 |
| 7 | 138 | 2,500 | 5.3% | 213 | $0.96 |
| 8 | 140 | 9,850 | 11.6% | 464 | $2.85 |
| 9 | 141 | 6,780 | 2.1% | 85 | $0.00 |
| 10 | 142 | 4,560 | 3.6% | 144 | $0.45 |

TABLE 3-continued

Closed Loop W/CM Ratio & Batching Strength
Standard Deviations From Real Time Data

| Table [2] | | | Ref# | | |
|---|---|---|---|---|---|
| | | 1 | 2 | 3 | 4 |
| | | | | | Computed from batch |
| | | | Computed per | | data for avg strength of 4,000 psi |
| | | Period | Table [1] STDEV W/CM [C] | Batching Strength SD [D] | Bench Mark Savings |
| Ref # | PLANT | Volume, cyds | SDrWCM | SD(Del_S) | [E] |
| 11 | 143 | 7,860 | 6.0% | 242 | $1.18 |
| 12 | 146 | 3,450 | 7.8% | 310 | $1.69 |
| 13 | 147 | 5,450 | 2.8% | 111 | $0.20 |
| 14 | 150 | 9,540 | 9.4% | 374 | $2.17 |
| | | | | AVG/YCD | $1.21 |

In accordance with another embodiment, information relating to a characteristic of a mixture carried in a vehicle is provided to the driver of the vehicle. For example, if water is added to a concrete mixture carried in a vehicle, information indicating how the added water impacts the concrete's water content, strength, slump, etc., is provided to the driver. Such information is displayed, for example, on a screen of a laptop computer (or other processing device) held by the driver.

In current concrete production and delivery systems, water is added to a concrete mixture at various stages of production and delivery. In particular, water may be added to a concrete mixture being carried in a mixer truck at various stages as described below.

At the production facility, most of the quantity of water specified in the formulation is added; however, a certain amount (usually between 10% and 20%) is held back to allow for in-truck additions of water. This quantity of water that is held back is referred to as trim water. The trim amount is typically 1 to 5 gal/cyd, with the mix design water ranging on average from 30 to 40 gal/cyd. After the truck is under the batch plant hopper at the production facility, the truck is driven under an apparatus referred to as a slump rack. At this stage, the driver, by watching the drum rotation hydraulic pressure gauge, and observing it visually, adds enough water to bring the batch up to a slump value under the specified formulation slump value. The driver leaves the slump value below the formulation value to allow for in-truck additions of water. The driver typically adds the remaining water to the mixture while the mixture is being transported, to bring the slump up to the formulation value.

In accordance with an embodiment, an alert is transmitted to master database module 11 to report each addition of water at the production facility, and an alert is transmitted to master database module 11 to report each addition of water during transport. Master database module 11 stores the data received in each alert.

Disadvantageously, the manual measuring and adjusting of water content required by current concrete production and delivery systems as described above is prone to human error and therefore can be unreliable. This unreliability is a significant source of concrete variance and its associated cost. Water quantity variability is a main source of concrete W/CM ratio variance, which in turn results in strength variance. For example, a 10% StDev of W/CM of batched values versus formulation values, for a 5,000 psi concrete mixture directly results in a strength StDev 500 psi, which in turn can be shown to increase the concrete cost by 3% to 5%. Disadvantageously, such variability can have a negative impact on a producer's profitability.

Figure 21:
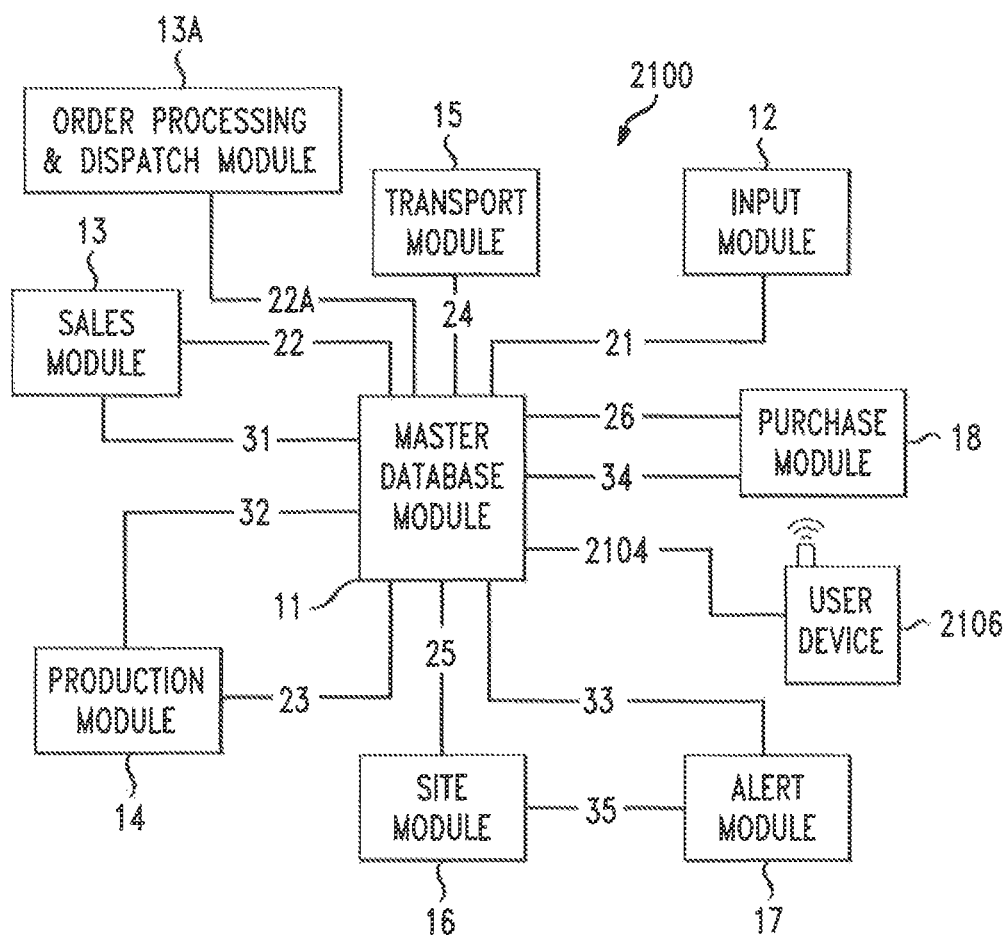
FIG. 21 shows a production management system in accordance with another embodiment.

FIG. 21 shows a production and delivery management system in accordance with an embodiment. Similar to certain embodiments described above, product management system 2100 includes a master database module 11, an input module 12, a sales module 13, an order & dispatch module 13A, a production module 14, a transport module 15, a site module 16, an alert module 17, a purchase module 18, and a localization module 19. Production management system 2100 also includes a user device 2106. User device 2106 communicates with master database module 11 via connection 2104, which may include, for example, a wireless connection via a wireless network and/or a connection via the Internet.

Figure 22:
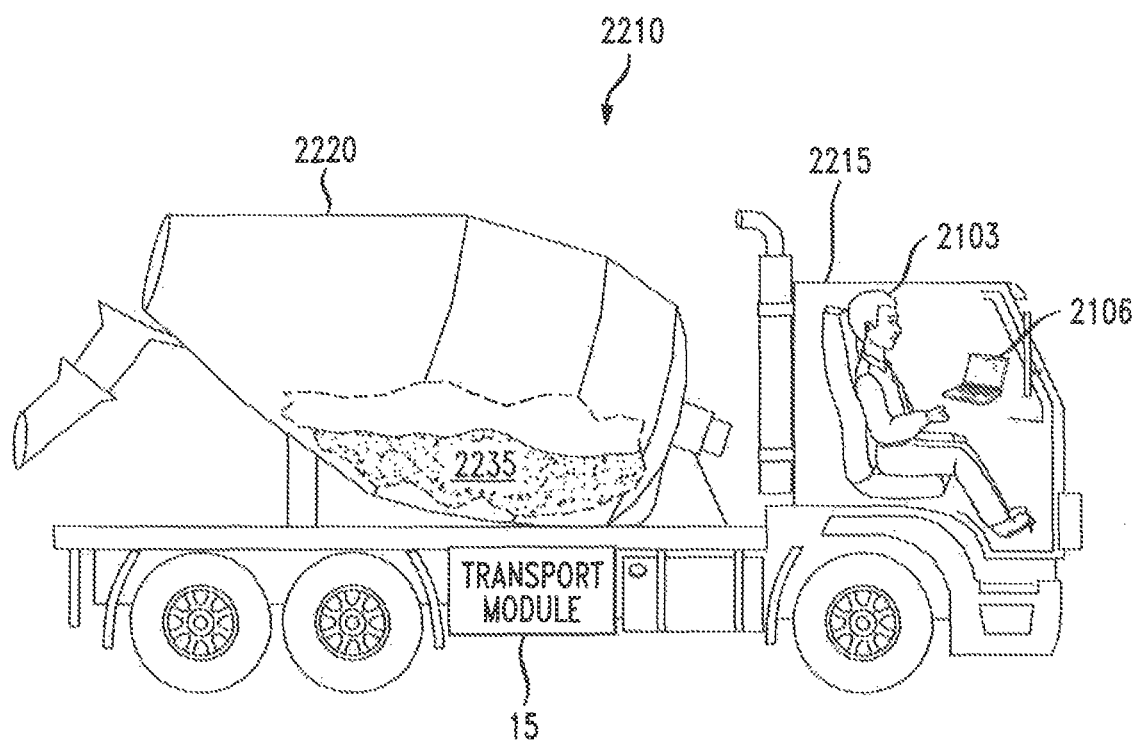
FIG. 22 shows a vehicle carrying a mixture in accordance with an embodiment.

FIG. 22 shows a concrete mixer truck 2210 carrying a concrete mixture 2235 in a mixer 2220. Mixture 2235 is a concrete mixture prepared based on a formulation. Truck 2210 includes transport module 15. Transport module 15 obtains information relating to truck 2210, such as its location, and information relating to mixture 2235, such as information indicating any additions of water and/or chemicals made to mixture 2235 during transport, and transmits such information to master database module 11. Transport module 15 may comprise a processing device having wireless communication capabilities, for example. For example, transport module 15 may communicate with master database module 11 via connection 24, which may be a connection over a wireless network and/or another network such as the Internet.

A driver 2103 located in a cab 2215 of truck 2210 holds user device 2106. In accordance with an embodiment, the driver may receive, via user device 2106, information relating to mixture 2235.

In one embodiment, real-time communication between user device 2106 and master database module 11 is achieved via the GPS data stream of vehicle 2210.

Figure 23:
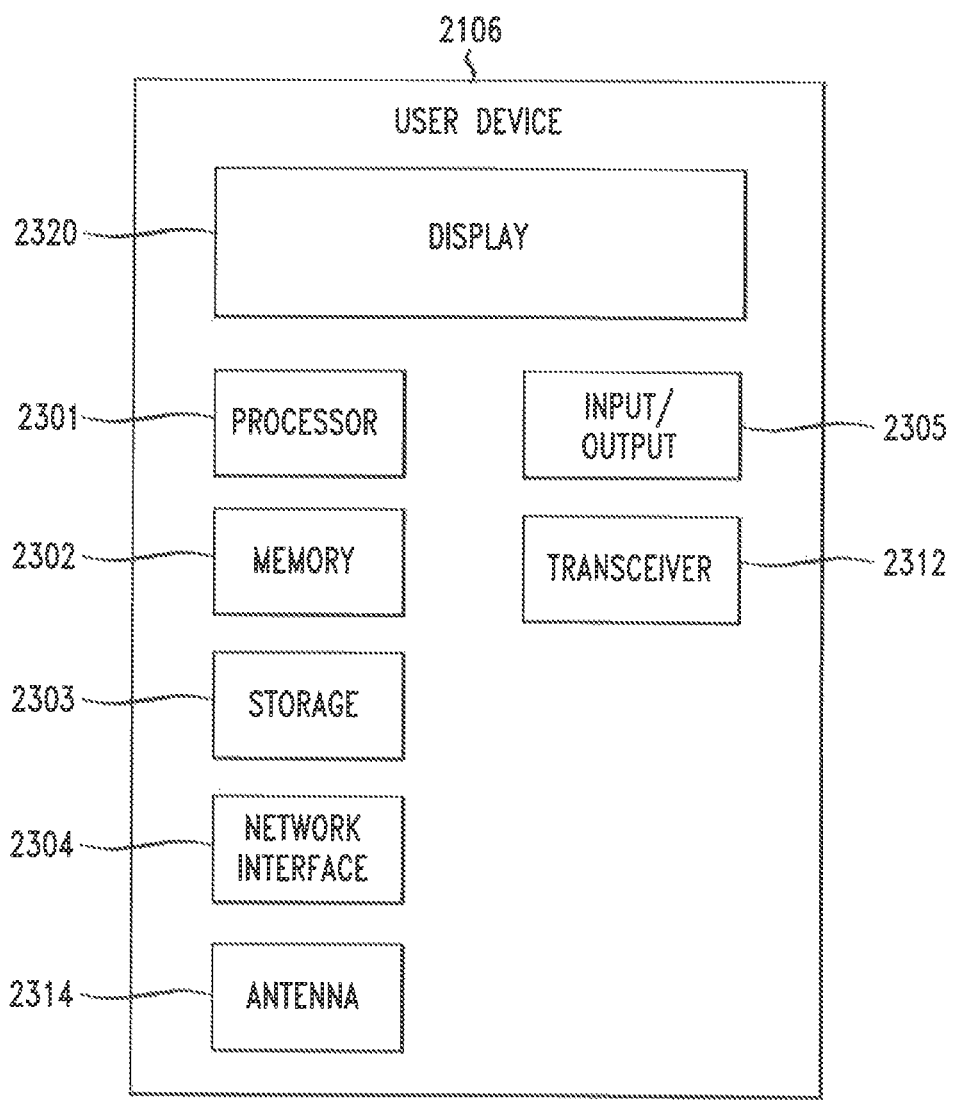
FIG. 23 shows components of a user device in accordance with an embodiment.

FIG. 23 shows components of user device 2106. User device 2106 comprises a processor 2301, a memory 2302, a storage 2303, a network interface 2304, one or more input/output devices 2305, a transceiver 2312, an antenna 2314, and a display 2320. Processor 2301 orchestrates the operations of one or more components of user device 2106. Memory 2302 and storage 2303 are used by other components of user device 2106 to store various types of data. Network interface 2304 enables user device 2106 to communicate via a network such as the Internet, a wireless communication network, or another type of network. Input/output devices 2305 allow a user to provide data to, and receive information from, user device 2106. Input/output devices 2305 may include, for example, a keyboard, a computer mouse, a microphone, etc. Antenna 2314 receives various types of signals propagating via electromagnetic waves. Transceiver 2312 transmits and receives signals via antenna 2314.

User device 2106 may be any suitable type of processing device. For example, user device 2106 may be a personal computer, a laptop computer, a tablet device, a wireless telephone, a personal digital assistant, a media player, a processing device built into the dashboard of a vehicle, etc.

In accordance with an embodiment, a real-time gauge is displayed on user device 2106 for the purpose of tracking and displaying the impact of any additions of water and/or chemicals on the mixture 2235 in truck 2210. The impact of any addition of water and/or chemicals on one of a variety of characteristics of the mixture may be displayed on the gauge as a difference from a respective formulation value. For example, when water is added to the mixture, the addition is recorded by master database module 11. Master database module 11 then determines the expected impact of the added water on the water content of the mixture, on concrete strength, on slump, and/or on other characteristics of the mixture. For example, the expected impact may be computed relative to the design value (the theoretical value computed based on the formulation) of water content, strength, slump, etc. The expected impact may be displayed in the form of an indicator on a gauge shown on user device 2106; the gauge may also display acceptable tolerances and whether the expected value of a particular characteristic after the addition is within the specified tolerances. In the illustrative embodiment, the driver of truck 2210 carries user device 2106 in the cab of the truck, to monitor the status of the mixture.

Figure 24:
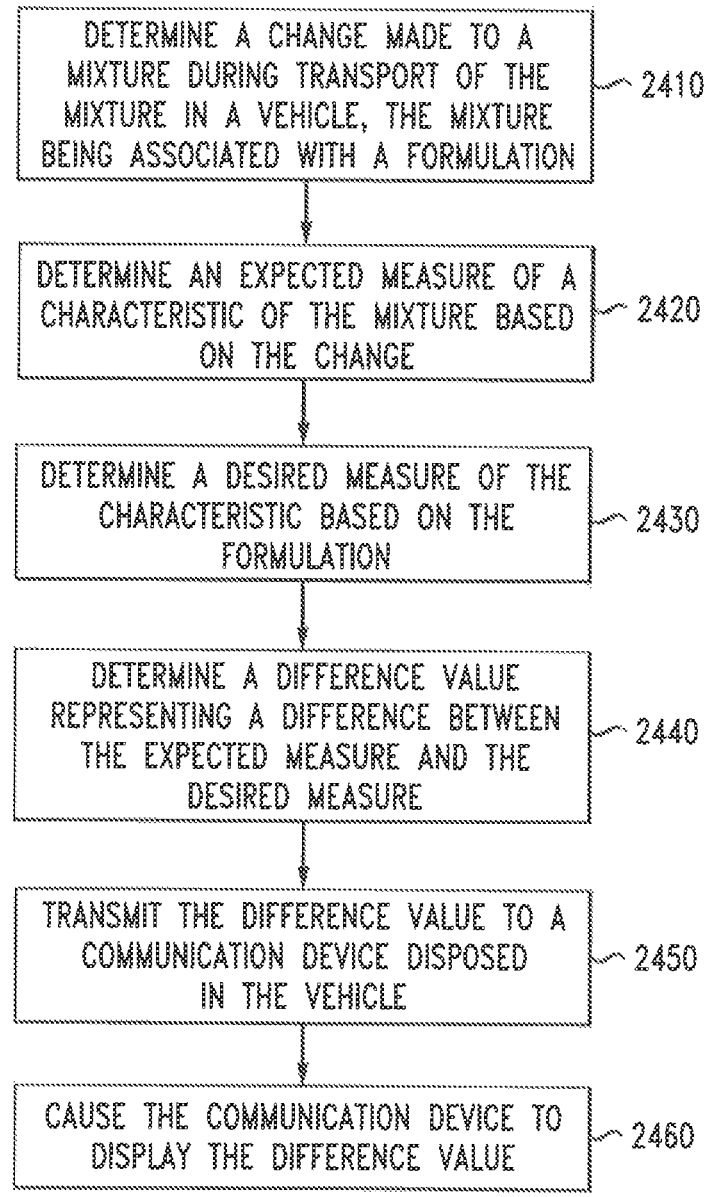
FIG. 24 is a flowchart of a method of managing information in accordance with an embodiment.

FIG. 24 is a flowchart of a method of providing information relating to a mixture carried in a vehicle to the driver of the vehicle in accordance with an embodiment. Referring to the illustrative embodiments of FIGS. 21 and 22, suppose that truck 2210 obtains mixture 2235 at a production facility. As the truck pulls under the production facility (no water has yet been added), master database module 11 provides to user device 2106 a web page or an App display such as that shown in FIG. 25. Web page 2500 (or an App display) includes a gauge 2510 showing the quantity of water in the mixture, represented as the difference between the expected quantity of water in the mixture and the design quantity determined based on the formulation. Gauge 2510 comprises a plurality of markings 2540 representing possible values (e.g., −2 gal/cyd, +2 gal/cyd, etc.) for the difference between the expected quantity and the design quantity. The difference is indicated by an arrow 2523. Gauge 2510 also displays a shaded region 2536 representing a range of acceptable tolerances for the quantity of water in the mixture. Thus, in the illustrative embodiment, the acceptable tolerances for water include quantities between −1 gal/cyd relative to the design quantity and +1 gal/cyd relative to the design quantity. Master database module 11 may cause user device 2106 to display web page 2500 (or an App display) on display 2320 (shown in FIG. 23), for example.

Figure 25:
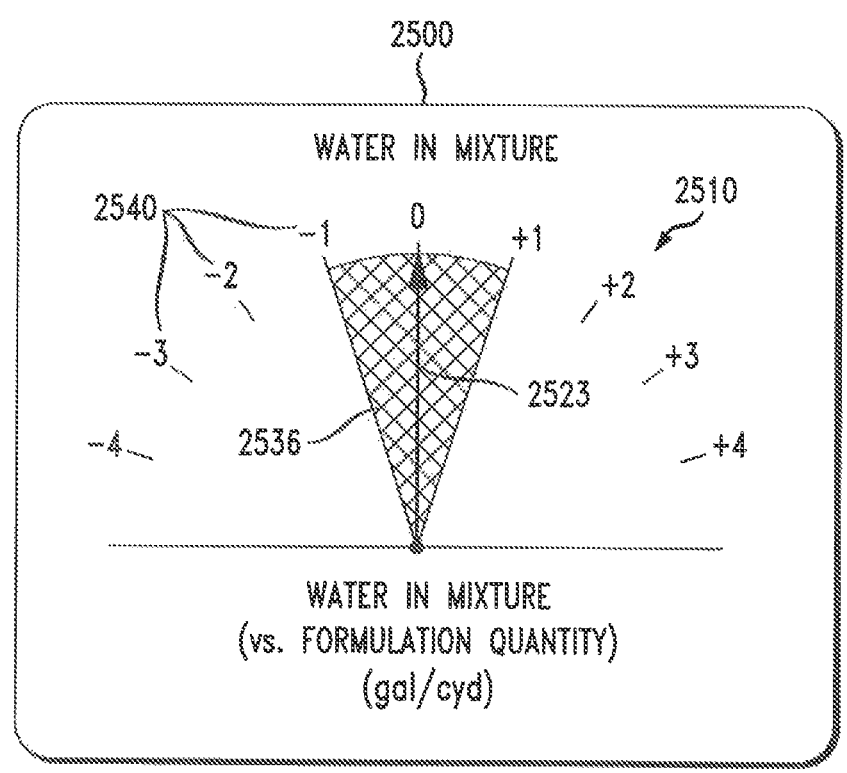
FIGS. 25-29 show web pages or Apps displaying gauges which show information related to a mixture in accordance with various embodiments.

Before any water is added, arrow 2523 indicates a difference of zero (0), as shown in FIG. 25.

In the illustrative embodiment, water is added to mixture 2235 at the production facility; however, the trim amount is 3 gal/cyd; this amount is not added to the mixture, as is common practice in the concrete industry. Production module 14 communicates to master database module 11 the amount of water added and the trim amount. Master database module 11 stores the information.

Figure 26:
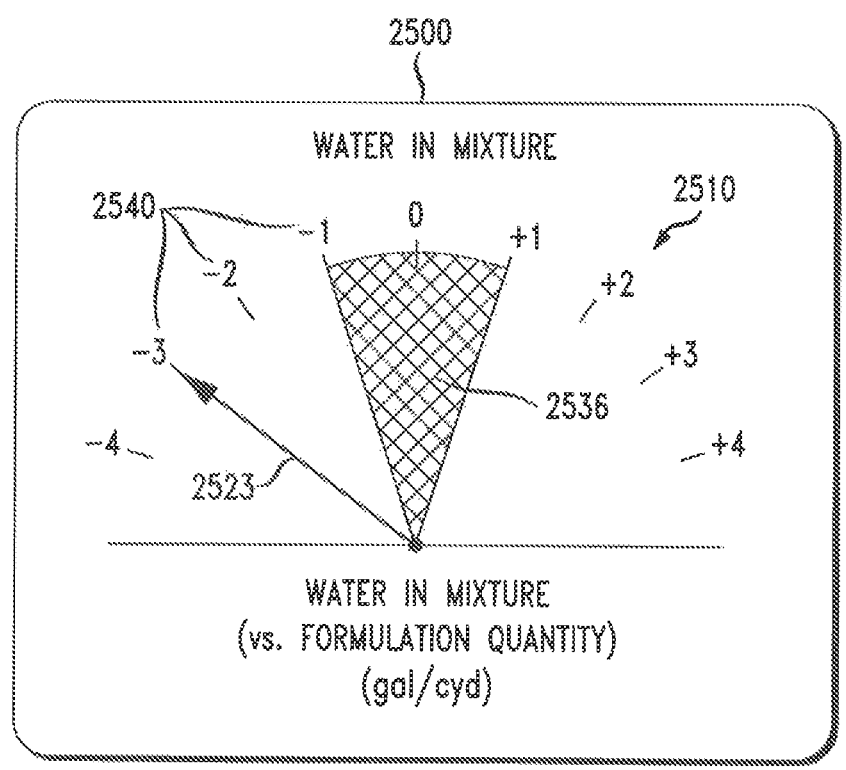

Master database module 11 again determines an expected quantity of water in the mixture, based on the addition of water (without the trim). Master database module 11 also determines a theoretical (design) quantity that the mixture should have at this stage in production, based on the formulation. Referring to FIG. 26, arrow 2523 now indicates −3 gal/cyd, due to the 3 gal/cyd of trim water that was held back. Accordingly, the driver may add up to 4 gal/cyd of water during transport and still be within acceptable tolerances.

Truck 2220 now begins to transport the mixture to a specified delivery site. Production module 14 (operating at the production facility) transmits an alert to master database module 11 that the truck has left the facility and is en route to the delivery site. Master database module 11 receives the information concerning the status of truck 2220 and stores the information.

During transport, the driver may add water to the mixture, as is common practice in the concrete industry. As discussed above, in the illustrative embodiment, the driver may add up to 4 gal/cyd of water to mixture 2235 during transport and still be within acceptable tolerances. When water is added during transport, transport module 15 detects the addition of water and transmits an alert to master database module 11 indicating how much water was added. Referring to FIG. 24, at step 2410, a change made to a mixture during transport of the mixture in a vehicle is determined, wherein the mixture is associated with a formulation. Supposing that the driver adds 2.5 gal/cyd during transport, master database module 11 receives the information from transport module 15 concerning the addition of water and stores the information.

At step 2420, an expected measure of a characteristic of the mixture is determined based on the change. Master database module 11 examines the addition of water made to mixture 2235 during transport, and examines previous additions of water to the mixture, and determines an expected quantity of water for mixture 2235. Master database module 11 may consider historical data concerning other, prior mixtures in determining an expected quantity of water for mixture 2235. For example, master database module 11 may also consider factors such as type of cementitious temperature, distance traveled, etc. to determine an expected quantity of water.

At step 2430, a desired measure of the characteristic is determined based on the formulation. Master database module 11 examines the formulation from which mixture 2235 was made and determines a theoretical (design) quantity of water that the mixture should contain.

Figure 27:
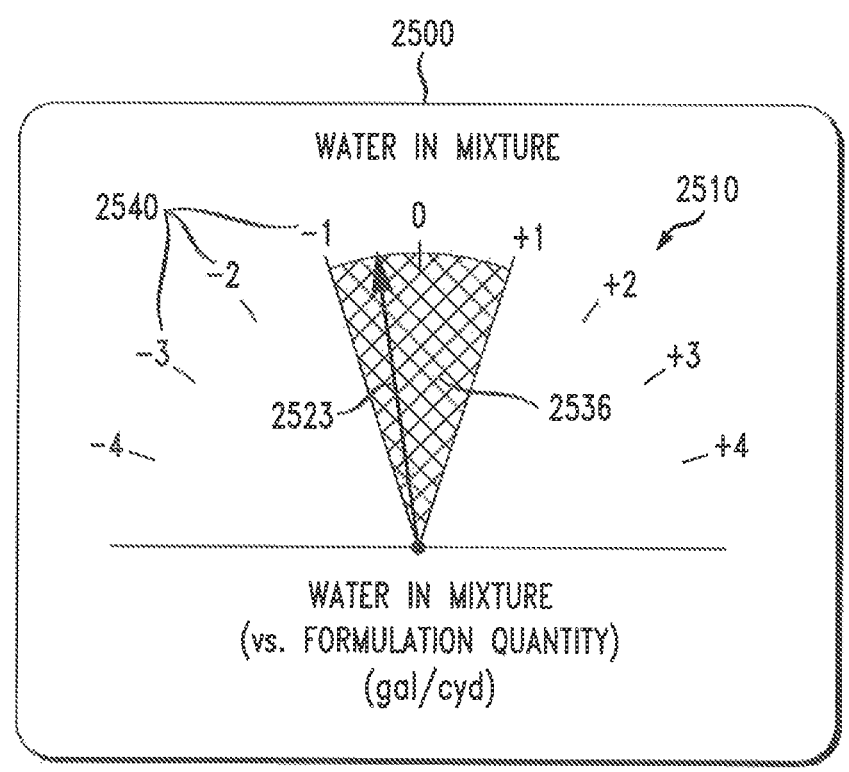

At step 2440, a difference value representing a difference between the expected measure and the desired measure is determined. Master database module 11 computes a difference between the theoretical (design) quantity of water formulation determined using the formulation and the expected quantity of water. At step 2450, the difference value is transmitted to a communication device disposed in the vehicle. Master database module 11 transmits to user device 2106 information indicating the difference between the design quantity and the expected quantity of water. At step 2460, master database module 11 causes the communication device to display the difference value. Master database module 11 presents a web page (or App display) showing the difference value on a gauge. Returning to the illustrative embodiment described above, after the driver adds 2.5 gal/cyd of water during transport, master database module 11 causes gauge 2510 to appear as shown in FIG. 27. Gauge 2510 now indicates that the expected quantity of water relative to the design quantity is approximately −0.5, which is within shaded region 2536 and therefore within acceptable tolerances.

The systems and methods for providing information to the driver of a truck transporting a mixture, as described herein, advantageously empowers the driver with a real-time, quantitative management tool. In addition, the systems and methods described herein facilitate operational management transparency in real-time across a large number of trucks.

While in the illustrative embodiment described above, the method described in FIG. 24 is used to determine and display information concerning the impact of a change in the quantity of water on the expected quantity of water in a mixture, in other embodiments, similar methods may be used to determine the impact of a change made to a mixture on other characteristics, including, without limitation, a strength of the mixture, a slump of the mixture, a standard deviation of strength, a standard deviation of slump, a quantity of cementitious in the mixture, a cost measure associated with the mixture, etc.

Figure 28:
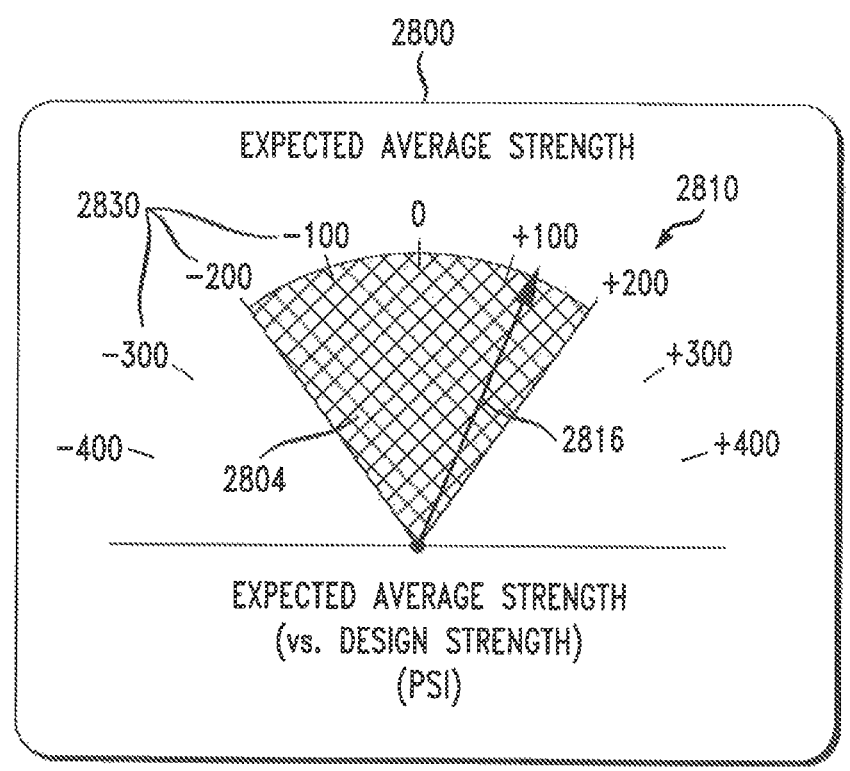

For example, in accordance with another embodiment, master database module 11 determines the impact of an addition of a quantity of water to a concrete mixture carried in vehicle 2210 on the expected strength of the concrete mixture. Master database module 11 causes user device 2106 to display a difference between the expected strength value and a theoretical (design) strength value determined based on the formulation. Using associated strength test data with the given formulation, and real-time regression of such data using Abrams' W/CM law and utilization of actual W and CM values, master database module 11 computes the influence of the added quantity of water (delta_water) on the strength of the mixture. The difference between expected strength and design strength may be displayed on a web page (or App display) such as that shown in FIG. 28. Web page 2800 includes a gauge 2810 that comprises a plurality of markings 2830 representing possible differences between expected strength and design strength. The sensitivity may be, for example, on the order of 100 psi to more than 200 psi per 1 gal/cyd of water depending on the strength grade of formulation. Gauge 2810 includes an arrow 2816 that indicates the difference. Gauge 2810 also includes a shaded region 2804 representing a region of acceptable tolerances.

Thus, for example, if the driver holds back 1 gal/cyd of water and the design strength is 4,000 psi, the gauge will show around +150 psi, indicating that the expected average strength will be around 4,150 psi. In the illustrative embodiment of FIG. 28, arrow 2816 indicates that the difference between expected strength and design strength is approximately +150 psi.

In another embodiment, a gauge showing strength StDev for a given formulation from data stored in a master database, calculated based on historical data, may be displayed.

In accordance with another embodiment, master database module 11 determines the impact of an addition of a quantity of water to a concrete mixture carried in vehicle 2210 on the expected slump of the concrete mixture. Master database module 11 causes user device 2106 to display a difference between the expected slump value and a theoretical (design) slump value determined based on the formulation. Using associated slump test data with the given formulation, and real-time regression of such data, master database module 11 computes the influence of the added quantity of water (delta_water) on the slump of the mixture. The difference between expected slump and design slump may be displayed on a web page (or App display) such as that shown in FIG. 29. Web page 2900 includes a gauge 2910 that comprises a plurality of markings 2930 representing possible differences between expected slump and design slump. The sensitivity may be, for example, on the order of 1 inch to 2 inches slump per gal/cyd of added water. Gauge 2910 includes an arrow 2916 that indicates the difference. Gauge 2910 also includes a shaded region 2904 representing a region of acceptable tolerances.

Figure 29:
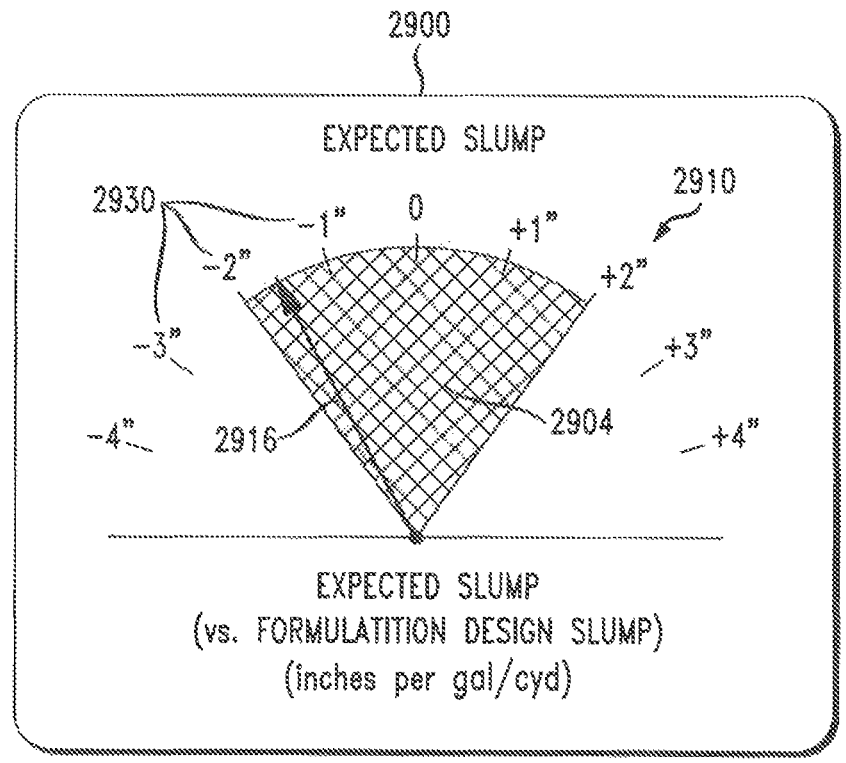

In an illustrative embodiment, supposing the formulation design slump is 4 inches, and the driver holds back 1 gal/cyd of water, gauge 2910 may show between −1 inch and −2 inches, as shown in FIG. 29.

In accordance with an embodiment, the effect of the slump retention rate can be determined using the principles set forth below. It is noted that current technology in concrete mixer trucks typically includes functionality for measuring and wirelessly transmitting data indicating the temperature inside the truck's drum.

The rate of slump loss is a function of both temperature T (in degrees absolute) and time t, determined using the algorithm described below.

1. $SLP(t,T) = (SLP_{initial})(Exp[(-a)(t/T)])$, where SLP=slump, $SLP_{initial}$=slump when batched, and "a" is an experimentally/empirically determined constant. $SLP_{initial}$ may be estimated based on methods described above.
2. The function described in (1) above is used to compute SLUMP retention during transport and delivery. Accordingly, the slump gauge continually auto-updates every few minutes. For example, if the gauge indicates a delta-slump of zero at the production facility, at a location half-way to the delivery site, the gauge may show −2 inches.
3. When water is added incrementally, the computation is readjusted for each new incremental addition of water, and superimposed on the previously existing retention profiles.
4. Thus, the slump gauge may show decreased slump over time, where the decrease may be higher when the temperature is higher.
5. However, when water is added, there is a discrete slump increase followed by a time and temperature dependent decline.

In another embodiment, a gauge showing StDev of slump for a given formulation from data stored in a master database, calculated based on historical data, may be displayed.

Figure 30:
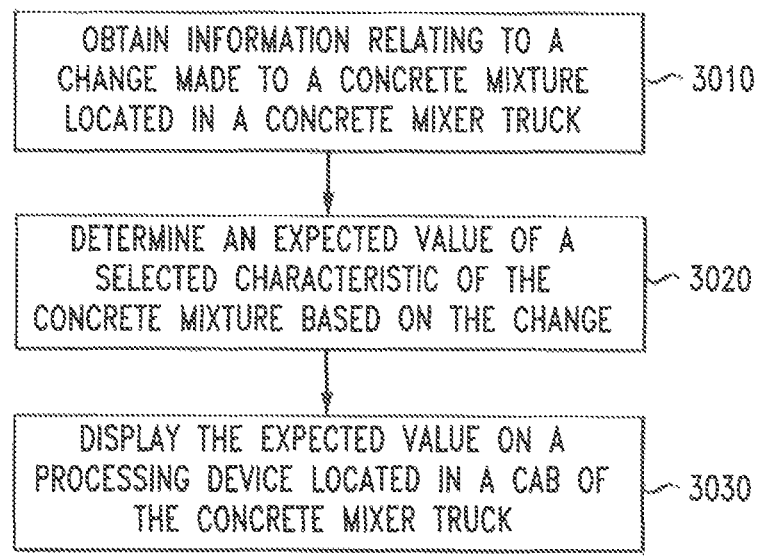
FIG. 30 is a flowchart of a method of managing information in accordance with an embodiment.

FIG. 30 is a flowchart of a method of providing information relating to a concrete mixture in accordance with an embodiment. At step 3010, information relating to a change made to a concrete mixture in a concrete mixer truck is obtained. At step 3020, an expected value of a selected characteristic of the concrete mixture is determined based on the change. At step 3030, the expected value is displayed on a processing device located in a cab of the concrete mixer truck.

In accordance with another embodiment, master database module 11 determines an impact of an addition of a particular component to a mixture, on a characteristic of the mixture. The component may be water, a chemical, or any other component of the mixture. For example, an expected value of a selected characteristic of a concrete mixture may be determined based on an added quantity of a chemical. A difference between the expected value and a design (formulation) value for the characteristic is determined, and the difference is displayed to the driver of the transport vehicle, in the form of a gauge.

The impact of chemicals may be more complicated than that of water. Thus, methods and systems similar to those described above may be used; however, the test data used to drive the gauge algorithms may be based on tests performed on concrete mixtures including the particular chemicals of interest.

In another embodiment, a gauge such as any of those shown in FIGS. 25-29 may be color coded to assist the driver in comprehending the effect that any addition of water (or other component) may have on the mixture. For example, referring to gauge 2510 shown in FIGS. 25-27, a left-hand portion of shaded region 2536 may be colored green, indicating that any additions of water to the concrete mixture made while arrow 2523 is in this (green) zone have a positive effect on the concrete's strength; a right-hand portion of shaded region 2536 may be colored red, indicating that additions of water while arrow 2523 is in this (red) region have a negative effect on the concrete's strength. Other regions of a gauge may be colored differently to convey other information.

In another embodiment, a user or operations manager may optionally switch a gauge between an analog mode (shown in the figures) to a digital mode, in which delta and limit values are shown digitally. Data shown in digital form may be color-coded as appropriate.

In another embodiment, a gauge may be switched to SI units or to percentage values.

The methods and systems described herein are not to be construed as limiting. While these methods and systems are described as being used to display information relating to water content, strength, slump, etc., in other embodiments, a gauge showing other characteristics of a mixture may be provided and displayed on user device 2106.

Figure 31:
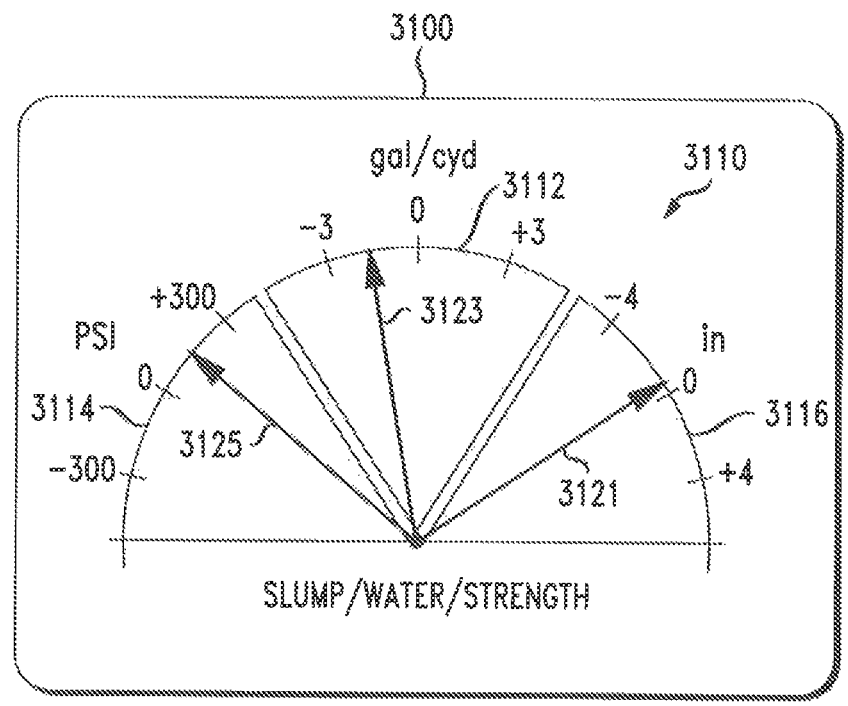
FIG. 31 shows a web page or App displaying a gauge which shows information related to a mixture in accordance with an embodiment.

In accordance with another embodiment, a combined gauge displaying multiple characteristics, e.g., data related to water in mixture 2235, data related to the slump of mixture 2235, and data related to the strength of mixture 2235, may be displayed on user device 2106. FIG. 31 shows a web page displaying a combined gauge showing water data, slump data, and strength data in accordance with an embodiment. Gauge 3110 includes a first region 3114 in which a first arrow 3125 indicates a difference in expected slump of mixture 2235 relative to design slump. Gauge 3110 includes a second region 3112 in which a second arrow 3123 indicates a difference in water in mixture 2235 relative to a design quantity of water. Gauge 3110 includes a third region 3116 in which a third arrow 3121 indicates a difference in the strength of mixture 2235 relative to design strength.

In another embodiment, some or all of the functions described herein as being performed by master database module 11 with respect to determining data to be displayed on a gauge, and causing a user device to display the gauge, are performed by user device 2106. Thus, for example, user device 2106 (located in the cab of truck 2210) may obtain information relating to a change made to a concrete mixture located in the truck, determine an expected value of a selected characteristic of the concrete mixture based on the change, determine a difference between the expected value and a design value, and display the difference value on a display such as display 2320 (shown in FIG. 23). User device 2106 may display such information in the form of a gauge.

In certain embodiments, communications between master database module 11, user device 2106, and other components are conducted in real time. Thus, data relating to changes made in components of mixture 2235 are communicated to master database module 11 in accordance with predetermined time constraints. Similarly, data relating to expected quantities of water, expected strength, expected slump, etc., and difference values, are transmitted by master database module 11 to user device 2106 in accordance with predetermined time constraints.

In various embodiments, the method steps described herein, including the method steps described in FIGS. 2, 3, 4, 5, 6, 9, 12, 13A-13B, 16A-16B, 17, 18, 19A-19B, 24, and/or 30, may be performed in an order different from the particular order described or shown. In other embodiments, other steps may be provided, or steps may be eliminated, from the described methods.

Systems, apparatus, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be used within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc.

Systems, apparatus, and methods described herein may be implemented using a computer program product tangibly embodied in an information carrier, e.g., in a non-transitory machine-readable storage device, for execution by a programmable processor; and the method steps described herein, including one or more of the steps of FIGS. 2, 3, 4, 5, 6, 9, 12, 13A-13B, 16A-16B, 17, 18, 19A-19B, 24 and/or 30, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 32:
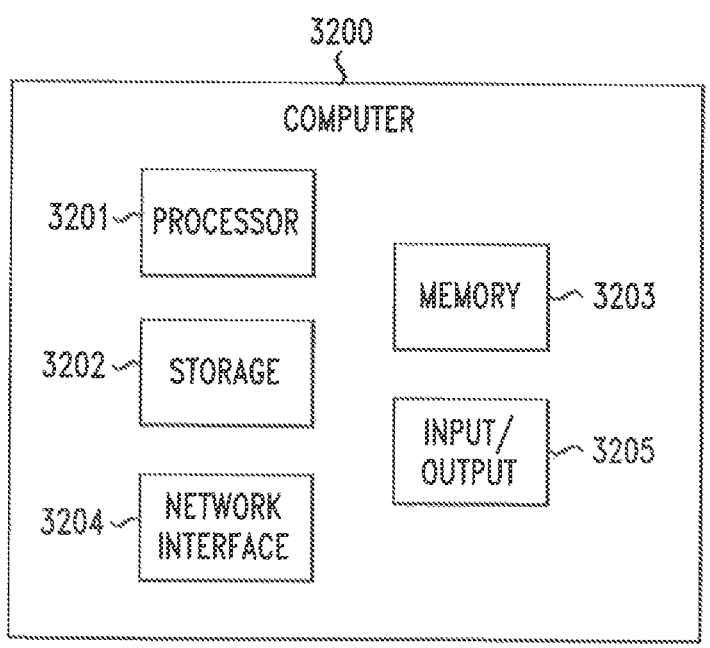
FIG. 32 is a high-level block diagram of an exemplary computer that may be used to implement certain embodiments.

A high-level block diagram of an exemplary computer that may be used to implement systems, apparatus and methods described herein is illustrated in FIG. 32. Computer 3200 includes a processor 3201 operatively coupled to a data storage device 3202 and a memory 3203. Processor 3201 controls the overall operation of computer 3200 by executing computer program instructions that define such operations. The computer program instructions may be stored in data storage device 3202, or other computer readable medium, and loaded into memory 3203 when execution of the computer program instructions is desired. Thus, the method steps of FIGS. 2, 3, 4, 5, 6, 9, 12, 13A-13B, 16A-16B, 17, 18, 19A-19B, 24 and/or 30 can be defined by the computer program instructions stored in memory 3203 and/or data storage device 3202 and controlled by the processor 3201 executing the computer program instructions. For example, the computer program instructions can be implemented as computer executable code programmed by one skilled in the art to perform an algorithm defined by the method steps of FIGS. 2, 3, 4, 5, 6, 9, 12, 13A-13B, 16A-16B, 17, 18, 19A-19B, 24 and/or 30. Accordingly, by executing the computer program instructions, the processor 3201 executes an algorithm defined by the method steps of FIGS. 2, 3, 4, 5, 6, 9, 12, 13A-13B, 16A-16B, 17, 18, 19A-19B, 24 and/or 30. Computer 3200 also includes one or more network interfaces 3204 for communicating with other devices via a network. Computer 3200 also includes one or more input/output devices 3205 that enable user interaction with computer 3200 (e.g., display, keyboard, mouse, speakers, buttons, etc.).

Processor 3201 may include both general and special purpose microprocessors, and may be the sole processor or one of multiple processors of computer 3200. Processor 3201 may include one or more central processing units (CPUs), for example. Processor 3201, data storage device 3202, and/or memory 3203 may include, be supplemented by, or incorporated in, one or more application-specific integrated circuits (ASICs) and/or one or more field programmable gate arrays (FPGAs).

Data storage device 3202 and memory 3203 each include a tangible non-transitory computer readable storage medium. Data storage device 3202, and memory 3203, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 3205 may include peripherals, such as a printer, scanner, display screen, etc. For example, input/output devices 3205 may include a display device such as a cathode ray tube (CRT) or liquid crystal display (LCD) monitor for displaying information to the user, a keyboard, and a pointing device such as a mouse or a trackball by which the user can provide input to computer 3200.

Any or all of the systems and apparatus discussed herein, including master database module 11, input module 12, sales module 13, production module 14, transport module 15, site module 16, alert module 17, purchase module 18, localization module 19, comparison module 1520, cloud database 1530, user device 1540, and user device 2106, and components thereof, including mixture database 801 and local factors database 802, for example, may be implemented using a computer such as computer 3200.

One skilled in the art will recognize that an implementation of an actual computer or computer system may have other structures and may contain other components as well, and that FIG. 32 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A system comprising:
    at least one memory storing computer program instructions; and
    at least one processor configured to execute the computer program instructions which, when executed on the at least one processor, cause the at least one processor to perform operations comprising:
        obtaining, from a device in a vehicle, information relating to a change made to a mixture while the mixture is being transported in the vehicle;
        determining an expected value of a selected characteristic of the mixture based on the change; and
        causing a communication device to display a web page that includes a representation of the expected value.

2. The system of claim 1, wherein the change comprises an addition of a chemical to the mixture.

3. The system of claim 1, wherein the mixture is produced based on a formulation,
    the operations further comprising:
        causing the communication device to display a graphical representation of a gauge, wherein an indicator of the gauge indicates a difference between the expected value and a second value of the characteristic determined based on the formulation.

4. The system of claim 3, wherein the graphical representation of a gauge includes an indication of whether or not the difference is within a predetermined tolerance.

5. The system of claim 1, wherein:
    the mixture is a concrete mixture; and
    the vehicle is a concrete mixing truck.

6. A method of managing information, the method comprising:
    determining a change made to a mixture during transport of the mixture in a vehicle;
    determining an expected measure of a characteristic of the mixture based on the change;
    determining a difference value representing a difference between the expected measure and a desired measure of the characteristic; and
    causing a communication device to display a web page that includes the difference value.

7. The method of claim 6, wherein the change comprises an addition of a substance to the mixture.

8. The method of claim 7, wherein the substance is one of water and a chemical.

9. The method of claim 8, wherein the change comprises a first addition of a first quantity of the substance to the mixture;
    the method further comprising:
        receiving information relating to a second addition of a second quantity of the substance to the mixture; and
        determining the expected measure of the characteristic of the mixture based on the change and the second addition of the substance.

10. The method of claim 9, wherein determining an expected measure of a characteristic of the mixture based on the change comprises examining historical data relating to the effect of the change on the characteristic.

11. The method of claim 9, further comprising:
    causing the communication device to display a graphical representation of a gauge, wherein an indicator of the gauge indicates the difference value.

12. The method of claim 11, further comprising:
    causing the communication device to display a shaded region on the gauge, the shaded region representing a range of difference values within acceptable tolerances.

13. A system comprising:
    a storage adapted to store:
        data relating to one or more changes made to a mixture; and
    at least one processor adapted to:
        determine a change made to a mixture during transport of the mixture in a vehicle;
        determine an expected measure of a characteristic of the mixture based on the change;
        determine a difference value representing a difference between the expected measure and a desired measure of the characteristic; and
        cause a communication device to display a web page that includes the difference value.

14. The system of claim 13, wherein:
    the mixture comprises a concrete mixture; and
    the vehicle comprises a concrete mixer truck.

15. The system of claim 13, wherein the change comprises an addition of a substance to the mixture.

16. The system of claim 15, wherein the change comprises one of an addition of water and an addition of a chemical.

17. The system of claim 16, wherein the change comprises a first addition of a first quantity of water to the mixture;
    the at least one processor being further adapted to:
        receive information relating to a second addition of a second quantity of water to the mixture; and
        determine the expected measure of the characteristic of the mixture based on the change and the second addition of water.

18. The system of claim 13, wherein the at least one processor is further adapted to:
    determine an expected measure of a characteristic of the mixture based on the change by examining historical data relating to the effect of the change on the characteristic.

19. The system of claim 13, wherein the at least one processor is further adapted to:
    cause the communication device to display a graphical representation of a gauge, wherein an indicator of the gauge indicates the difference value.

20. The system of claim 19, wherein the at least one processor is further adapted to:
    cause the communication device to display a shaded region on the gauge, the shaded region representing a range of difference values within acceptable tolerances.

* * * * *